(12) United States Patent
Longo et al.

(10) Patent No.: US 10,015,980 B2
(45) Date of Patent: Jul. 10, 2018

(54) METHODS AND FORMULATIONS PROMOTING TISSUE/ORGAN REGENERATION, LONGEVITY AND HEALTHSPAN

(71) Applicant: University of Southern California, Los Angeles, CA (US)

(72) Inventors: Valter D. Longo, Playa del Rey, CA (US); Chia-Wei Cheng, Los Angeles, CA (US); Sebastian Brandhorst, Redondo Beach, CA (US); Min Wei, West Covina, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 495 days.

(21) Appl. No.: 14/060,494

(22) Filed: Oct. 22, 2013

(65) Prior Publication Data

US 2014/0112909 A1    Apr. 24, 2014

Related U.S. Application Data

(60) Provisional application No. 61/746,787, filed on Dec. 28, 2012, provisional application No. 61/736,308, filed on Dec. 12, 2012, provisional application No. 61/716,676, filed on Oct. 22, 2012.

(51) Int. Cl.

| | | |
|---|---|---|
| *A61K 39/395* | (2006.01) | |
| *A61K 48/00* | (2006.01) | |
| *A23L 33/00* | (2016.01) | |
| *A61K 45/00* | (2006.01) | |
| *A23L 29/30* | (2016.01) | |
| *A23L 33/115* | (2016.01) | |
| *A23L 33/175* | (2016.01) | |
| *A23L 33/17* | (2016.01) | |
| *A23L 33/16* | (2016.01) | |
| *A23L 33/15* | (2016.01) | |
| *A23L 33/155* | (2016.01) | |

(52) U.S. Cl.
CPC .............. *A23L 33/40* (2016.08); *A23L 29/37* (2016.08); *A23L 33/115* (2016.08); *A23L 33/15* (2016.08); *A23L 33/155* (2016.08); *A23L 33/16* (2016.08); *A23L 33/17* (2016.08); *A23L 33/175* (2016.08); *A23L 33/30* (2016.08); *A61K 45/00* (2013.01); *A23V 2002/00* (2013.01)

(58) Field of Classification Search
None
See application file for complete search history.

(56) References Cited

U.S. PATENT DOCUMENTS

| | | |
|---|---|---|
| 8,211,700 B2 | 7/2012 | Longo |
| 8,728,815 B2 | 5/2014 | Longo |
| 8,865,646 B2 | 10/2014 | Longo |
| 2006/0063827 A1* | 3/2006 | Yu .................. A61K 31/198 514/423 |
| 2007/0116802 A1 | 5/2007 | Germano |
| 2008/0038367 A1 | 2/2008 | Saloum |
| 2011/0118528 A1 | 5/2011 | Longo et al. |
| 2013/0045215 A1 | 2/2013 | Longo et al. |
| 2013/0316948 A1 | 11/2013 | Longo |
| 2014/0328863 A1 | 11/2014 | Longo |
| 2015/0133370 A1 | 5/2015 | Longo |

FOREIGN PATENT DOCUMENTS

| | | |
|---|---|---|
| GB | 1356252 A | 6/1974 |
| WO | 2009-070378 A1 | 6/2009 |
| WO | WO 2011050302 A2 * | 4/2011 |
| WO | 2012-109353 A2 | 8/2012 |
| WO | 2012/113415 A1 | 8/2012 |
| WO | 2014/127000 A2 | 8/2014 |

OTHER PUBLICATIONS

Gerald et al. Alzheimer's disease market: hope deferred . Nature Reviews Drug Discovery, 2013; 12:19-20.*
Rubey. Could lysine supplementation prevent Alzheimer's dementia? A novel hypothesis. Neuropsychiatric Disease and Treatment, 2010; 6:707-710.*
Patel et al. Caloric restriction attenuates AB-deposition in Alzheimer transgenic models. Neurobiology of Aging. 2005; 26:995-1000.*
Trommelmans, L., "The challenge of regenerative medicine", Hastings Center Report, 2010, pp. 24-26, vol. 40, No. 6.
Yamamizu, K. et al., "PKA/CREB Signaling Triggers Initiation of Endothelial and Hematopoietic Cell Differentiation via Etv2 Induction", Stem Cells, 2012, pp. 687-696.
Yamamoto, H. et al., "Enzymatic conversion of IGF-I to des(1-3)IGF-I in rat serum and tissues: a further potential site of growth hormone regulation of IGF-I action", Journal of Endocrinology, 1995, pp. 141-148.
Yilmaz, O. H. et al., "mTORC1 in the Paneth cell niche couples intestinal stem cell function to calorie intake", Nature, 2012, pp. 1-16.
Young, S. N., "Behavioral Effects of Dietary Neurotransmitter Precursors: Basic and Clinical Aspects", Neuroscience and Biobehavioral Reviews, 1996, pp. 313-323, vol. 20 No. 2.
Zaman, S. et al., "How *Saccharomyces* Responds to Nutrients", 2008, pp. 27-81.

(Continued)

*Primary Examiner* — Vanessa L. Ford
*Assistant Examiner* — Sandra E Dillahunt
(74) *Attorney, Agent, or Firm* — Brooks Kushman P.C.

(57) ABSTRACT

A method includes a step of identifying a subject in need of diet modification; and administering a first diet to the subject for a first time period. The first diet provides 4.5 to 7 kilocalories per pound of subject for a first day and 3 to 5 kilocalories per pound of subject per day for a second to fifth day of the first diet. The first diet includes less than 30 g of sugar on the first day; less than 20 g of sugar on the second to fifth days; less than 28 g of proteins on the first day; less than 18 g of proteins on days the second to fifth days; 20 to 30 grams of monounsaturated fats on the first day; 10 to 15 grams of monounsaturated fats on the second to fifth days; and between 6 and 10 grams of polyunsaturated fats on the first day.

2 Claims, 23 Drawing Sheets

(56) References Cited

OTHER PUBLICATIONS

Zhang, S. et al., "CD200-CD200R Dysfunction exacerbates microglial activation and dopaminergic neurodegeneration in a rat model of Parkinson's disease", Journal of Neuroinflammation, 2011, pp. 1-12.
Adam, G. B. et al., "Therapeutic targeting of a stem cell niche", Nature Biotechnology, 2007, pp. 238-243, vol. 25 No. 2.
Bartke, A. et al., "Somatotropic Signaling: Trade-Offs Between Growth, Reproductive Development, and Longevity", Physiol Rev 93, 2013, pp. 571-598.
Bedford, P. et al., "The Level of DNA Interstrand Crosslinking in Bone Marrow Parallels the Extent of Myelosuppression in Mice Treated with Four Chloroethylnitrosoureas", Journal of Cancer Research and Clinical Oncology 108, 1984, pp. 141-147.
Bokov, A. F. et al., "Does Reduced IGF-1R Signaling in Igf1r +/− Mice Alter Aging?", PLoS One, 2011, 10 pgs.
Bondolfi, L. et al., "Impact of Age and Caloric Restriction on Neurogenesis in the Dentate Gyrus of C57BL/6 Mice", Neurobiology of Aging, 2004, pp. 333-340.
Brown-Borg, H. M. et al., "Dwarf Mice and the Ageing Process", Nature, Nov. 7, 1996, p. 33.
Carro E., et al., "Circulating Insulin-Like Growth Factor I Mediates Effects of Exercise on the Brain", The Journal of Neuroscience, Apr. 15, 2000, pp. 2926-2933.
Carro E., et al., "Insulin-like growth factor I and Alzheimer's disease: therapeutic prospects?", Expert Rev. Neurotherapeutics, 2004, pp. 79-86.
Carro E., et al., "Serum Insulin-like growth factor I regulates brain amyloid-levels", Nature Medicine, Dec. 2002, pp. 1390-1397, vol. 8 No. 12.
Carroll, J.C. et al., "Continuous and Cyclic Progesterone Differentially Interact with Estradiol in the Regulation of Alzheimer-Like Pathology in Female 3×Transgenic-Alzheimer's Disease Mice", Endocrinology, Jun. 2010, pp. 2713-2722.
Chen, J. et al., "Hematopoietic senescence is postponed and hematopoietic stem cell function is enhanced by dietary restriction", Experimental Hematology, 2003, pp. 1097-1103.
Cohen, E. et al., "Reduced IGF-1 Signaling Delays Age-associated Proteotoxicity in Mice", 2009, pp. 1-23.
De Coppi, P. et al., "Isolation of amniotic stem cell lines with potential for therapy", Nature Biotechnology, 2007, pp. 100-106.
De Leon, M.J. et al., "Longitudinal CSF and MRI biomarkers improve the diagnosis of mild cognitive impairment", 2006, pp. 394-401.
Ditadi, A. et al., "Human and murine amniotic fluid c-Kit+Lin-cells display hematopoietic activity", Blood, Apr. 23, 2009, pp. 3953-3960, vol. 113, No. 17.
Ertl, R. P. et al., "Effects of dietary restriction on hematopoietic stem-cell aging are genetically regulated", Blood, Feb. 1, 2008, pp. 1709-1716, vol. 111, No. 3.
Fabrizio, P. et al., "Regulation of Longevity and Stress Resistance by Sch9 in Yeast", Science, Apr. 13, 2001, pp. 288-290, vol. 292.
Fabrizio, P. et al., "SOD2 Functions Downstream of Sch9 to Extend Longevity in Yeast", Genetics, Jan. 2003, pp. 35-46.
Faherty, S. et al., "Self-renewal and differentiation of mouse embryonic stem cells as measured by Oct4 expressions: the role of the cAMP/PKA pathway", 2007, pp. 37-47.
Fontan-Lozano, A et al., "Molecular Bases of Caloric Restriction Regulation of Neuronal Synaptic Plasticity", 2008, pp. 167-177.
Fontana, L. et al., "Extending Healthy Life Span—From Yeast to Humans", 2010, pp. 321-326.
Fontana, L. et al., "Long-term effects of calorie or protein restriction on serum IGF-1 and IGFBP-3 concentration in humans", Oct. 2008, pp. 1-14.
Gietzen, D. W. et al., "Mechanisms of Food Intake Repression in Indispensable Amino Acid Deficiency", 2007, pp. 63-78.

Goedert, M. et al., "Monoclonal antibody AT8 recognises tau protein phosphorylated at both serine 202 and threonine 205", Neuroscience Letters 189, 1995, pp. 167-170.
Gonzalez, G. A. et al., "Cyclic AMP Stimulates Somatostatin Gene Transcription by Phosphorylation of CREB at Serine 133", Cell, Nov. 17, 1989, pp. 675-680, vol. 59.
Guevara-Aguirre, J. et al., Growth Hormone Receptor Deficiency Is Associated with a Major Reduction in ProAging Signaling, 2011, pp. 1-9.
Gulinello, M. et al., "Validation of a 2-day water maze protocol in mice", Jan. 23, 2009, pp. 220-227.
Hofmeister, C.C. et al., "Ex vivo expansion of umbilical cord blood stem cells for transplantation: growing knowledge from the hematopoietic niche", 2007, pp. 11-23.
Holzenberger, M. et al., "IGF-1 receptor regulates lifespan and resistance to oxidative stress in mice", Nature, Jan. 9, 2003, pp. 182-187, vol. 421.
Hwang, D. L. et al., "Quantitative Ontogeny of Murine Insulin-Like Growth Factor (IGF)-I, IGF-binding Protein-3 and the IGF-related Acid-labile Subunit", Feb. 2008, pp. 65-74.
Ikeno, Y. et al., "Reduced Incidence and Delayed Occurrence of Fatal Neoplastic Diseases in Growth Hormone Receptor/Binding Protein Knockout Mice", 2009, pp. 522-529, vol. 64A, No. 5.
Ito, K. et al., "Reactive oxygen species act through p38 MAPK to limit the lifespan of hematopoietic stem cells", 2006, pp. 446-451.
Kenyon, C., "A Conserved Regulatory System for Aging", Cell, 2001, pp. 165-168, vol. 105.
Ketelslegers, J. M. et al., "Nutritional Regulation of Insulin-Like Growth Factor-I", Metabolism, 1995, pp. 50-57, vol. 44 No. 10.
Kim, S. Y. et al., "PAGE: Parametric Analysis of Gene Set Enrichment", 2005, pp. 1-12.
Kinney, B. A. et al., "Evidence that age-induced decline in memory retention is delayed in growth hormone resistant GH-R-KO (Laron) mice", Physiology & Behavior, 2001, pp. 653-660.
Kirschner, L. S. et al., "Mouse models of altered protein kinase A signaling", Endocrine-Related Cancer, 2009, pp. 773-793.
Kitazawa, M. et al., "Lipopolysaccharide-Induced Inflammation Exacerbates Tau Pathology by a Cyclin-Dependent Kinase 5-Mediated Pathway in a Transgenic Model of Alzheimer's Disease", The Journal of Neuroscience, Sep. 28, 2005, pp. 8843-8853.
Kofman, A. E. et al., "Rapamycin increases oxidative stress response gene expression in adult stem cells", Aging, 2012, pp. 279-289.
Kolosova, N. G. et al., "Prevention of Age-Related Macular Degeneration-Like Retinopathy by Rapamycin in Rats", The American Journal of Pathology, Aug. 2012, pp. 472-477, vol. 181, No. 2.
Kucia, M. J. et al., "Evidence That Very Small Embryonic-Like Stem Cells Are Mobilized into Peripheral Blood", Stem Cells, 2008, pp. 2083-2092.
Halagappa, V. K. et al., "Intermittent fasting and caloric restriction ameliorate age-related behavioral deficits in the triple-transgenic mouse model of Alzheimer's disease", Neurobiology of Disease, 2007, pp. 212-220.
Kuret, J. et al., "Mutagenesis of the Regulatory Subunit of Yeast cAMP-dependent Protein Kinase", Jul. 5, 1988, pp. 9149-9154.
Lee, C. et al., "Fasting Cycles Retard Growth of Tumors and Sensitize a Range of Cancer Cell Types to Chemotherapy", Feb. 8, 2012, pp. 1-16.
Lee, C. et al., "Fasting vs dietary restriction in cellular protection and cancer treatment: from model organisms to patients", Oncogene, 2011, pp. 3305-3316.
Lee, C. et al., "Reduced Levels of IGF-I Mediate Differential Protection of Normal and Cancer Cells in Response to Fasting and Improve Chemotherapeutic Index", Jan. 11, 2012, pp. 1564-1572.
Kenyon, C., "The Plasticity of Aging: Insights from Long-Lived Mutants", Cell, 2005, pp. 449-460, vol. 120.
Longo, V. D. et al., "Evolutionary Medicine: From Dwarf Model Systems to Healthy Centenarians", Science, 2003, pp. 1342-1346.
Longo, et al., "Human Bcl-2 Reverses Survival Defects in Yeast Lacking Superoxide Dismutase and Delays Death of Wild-Type Yeast", The Journal of Cell Biology, Jun. 30, 1997, pp. 1581-1588, vol. 137 No. 7.

(56) References Cited

OTHER PUBLICATIONS

Luchsinger, J. A. et al., "Caloric Intake and the Risk of Alzheimer Disease", Arch Neurol, Aug. 2002, pp. 1258-1263, vol. 59.
Mackall, C. L. et al., "Lymphocyte Depletion During Treatment With Intensive Chemotherapy for Cancer", Blood, Oct. 1, 1994, pp. 2221-2228, vol. 84 No. 7.
Martin, B. et al., "Caloric restriction and intermittent fasting: Two potential diets for successful brain aging", Aug. 2006, pp. 332-353.
Masternak, M. M. et al., "Insulin Sensitivity as a Key Mediator of Growth Hormone Actions on Longevity", 2009, pp. 516-521, vol. 64A No. 5.
Matsumoto, K. et al., "Stepwise Development of Hematopoietic Stem Cells from Embryonic Stem Cells", Mar. 2009, pp. 1-10, vol. 4 Issue 3.
Mattson, M. P. et al., "Energy Intake, Meal Frequency, and Health: A Neurobiological Perspective", 2005, pp. 237-260.
Mauch, P. et al., "Hematopoietic Stem Cell Compartment: Acute and Late Effects of Radiation Therapy and Chemotherapy", 1995, pp. 1319-1339, vol. 31 No. 5.
Mouton, P. R. et al., "Caloric restriction attenuates amyloid deposition in middle-ages APP/ PS1 mice", Oct. 30, 2009, pp. 184-187.
Nimeth, K. T. et al., Stem Cell Dynamics During Growth, Feeding, and Starvation in the Basal Flatworm *Macrostomum* sp. (Platyhelminthes), Developmental Dynamics, 2004, pp. 91-99.
Oddo, S. et al., "Amyloid deposition precedes tangle formation in a triple transgenic model of Alzheimer's disease", Neurobiology of Aging, 2003, pp. 1063-1070.
Otis, M. et al., "Angiotensin II Stimulates Protein Synthesis and Inhibits Proliferation in Primary Cultures of Rat Adrenal Glomerulosa Cells", The Endocrine Society, 2005, pp. 633-642.
Pang, Q., "HSCs: stressing out over ROS", blood, Sep. 15, 2011, pp. 2932-2934, vol. 118, No. 11.
Parrella, E. et al., "Insulin/IGF-I and Related Signaling Pathways Regulate Aging in Nondividing Cells: from Yeast to the Mammalian Brain", TheScientificWorld, 2010, pp. 161-177.
Patel, N. V. et al., "Caloric restriction attenuates AB-deposition in Alzheimer transgenic models", Neurobiology of Aging, 2005, pp. 995-1000.
Polak, D. J., "Regenerative medicine. Opportunities and challenges: a brief overview", J.R. Soc. Interface, 2010, pp. S777-S781, 7 Suppl. 6.
Rafalski, V. A. et al., "Energy metabolism in adult neural stem cell fate", Progress in Neurobiology, 2011, pp. 182-203.
Raffaghello, L. et al., "Starvation-dependent differential stress resistance protects normal but not cancer cells against high-dose chemotherapy", Jun. 17, 2008, pp. 8215-8220, vol. 105 No. 24.
Ramos, F. J. et al., "Rapamycin Reverses Elevated mTORC1 signaling in Lamin A/C-Deficient Mice, Rescued Cardiac and Skeletal Muscle Function, and Extends Survival", Sci Transl Med., 2012, pp. 1-25.
Rando, T. A. et al., "Aging, Rejuvenation, and Epigenetic Reprogramming: Resetting the Aging Clock", Cell, 2012, pp. 46-57.
Ratajczak, J. et al., "Adult Murine Bone Marrow-Derived Very Small Embryonic-Like Stem Cells (VSELs) Differentiate Into the Hematopoietic Lineage After Co-Culture Over OP9 Stromal Cells", 2011, pp. 225-237.
Ratajczak, J. et al., "Hematopoietic Differentiation of Umbilical Cord Blood-Derived Very Small Embryonic/Epiblast-Like Stem Cells", Leukemia, 2011, pp. 1278-1285.
Ratajczak, J. et al., "Higher number of stem cells in bone marrow of circulating Igf-1 level low Laron dwarf mice—novel view on Igf-1, stem cells and aging", Leukemia, 2011, pp. 729-733.
Ratajczak, M. Z. et al., "A novel insight into aging: are there pluripotent very small embryonic-like stem cells (VSELs) in adult tissues overtime depleted in an Igf-1-dependent manner?", Aging, Nov. 2010, pp. 875-883, vol. 2 No. 11.
Ratajczak, M. Z. et al., "Very Small Embryonic-Like (VSEL) Stem Cells: Purification from Adult Organs, Characterization, and Biological Significance" Stem Cell Rev., 2008, pp. 89-99.

Kucia, M. et al., "A population of very small embryonic-like (VSEL) CXCR4+SSEA-1+Oct-4+ stem cells identified in adult bone marrow", Leukemia, 2006, pp. 857-869.
Rinaldi, J. et al., "Structure of Yeast Regulatory Subunit: A Glimpse into the Evolution of PKA Signaling", Structure, Nov. 10, 2010, pp. 1471-1482.
Roberson, E. D. et al., "Reducing Endogenous Tau Ameliorates Amyloid B-Induced Deficits in an Alzheimer's Disease Mouse Model", Science, May 4, 2007, pp. 750-754, vol. 316.
Rosario, E. R. et al., "Androgens Regulate the Development of Neuropathology in a Triple Transgenic Mouse Model of Alzheimer's Disease", The Journal of Neuroscience, Dec. 20, 2006, pp. 13384-13389.
Rybtsov, S. et al., "Hierarchical organization and early hematopoietic specification of the developing HSC lineage in the AGM region", The Journal of Experimental Medicine, 2011, pp. 1305-1315, vol. 208 No. 6.
Safdie, F. M. et al., "Fasting and cancer treatment in humans: A case series report", Aging, Dec. 2009, pp. 1-20, vol. 1 No. 12.
Sagar, J. et al., "Role of stem cells in cancer therapy and cancer stem cells: a review", Cancer Cell International, 2007, pp. 1-11.
Salmon, A. B. et al., "Fibroblast cell lines from young adult mice of long-lived mutant strains are resistant to multiple forms of stress", 2005, pp. E23-E29.
Sanghera, K. P. et al., "The PI3K/Akt/mTOR pathway mediates retinal progenitor cell survival under hypoxic and superoxide stress", Molecular and Cellular Neuroscience, 2011, pp. 145-153.
Schrag, M. et al., "Hippocampus of Ames Dwarf Mice Is Resistant to B-Amyloid-Induced Tau Hyperphosphorylation and Changes in Apoptosis-Regulatory Protein Levels", 2008, pp. 239-244.
Sharma, S. et al., "NMDA and kainate receptor expression, long-term potentiation, and neurogenesis in the hippocampus of long-lived Ames dwarf mice", Age, 2012, pp. 609-620.
Shrama, S. et al., "Spatial memory is enhanced in long-living Ames dwarf mice and maintained following kainic acid induced neurodegeneration", Jun. 2010, pp. 422-435.
Sonntag, W. E. et al., "Pleiotropic Effects of Growth Hormone and Insulin-like Growth Factor (IGF)-1 on Biological Aging: Inferences From Moderate Caloric-Restricted Animals", Journal of Gerontology, 1999, pp. B521-B538, vol. 54A No. 12.
Suh, Y. et al., "Functionally significant insulin-like growth factor I receptor mutations in centenarians", Mar. 4, 2008, pp. 3438-3442, vol. 105 No. 9.
Talbot, K. et al., "Demonstrated brain insulin resistance in Alzheimer's disease patients is associated with IGF-1 resistance, IRS-1 dysregulation, and cognitive decline", The Journal of Clinical Investigation, Apr. 2012, pp. 1317-1338, vol. 122 No. 4.
Tommelmans, L., "Regenerative medicine. Opportunities and Challenges: a brief overview", 2010, pp. 24-26, vol. 40 No. 6.
van Tilburg, C. M. et al., "Immune reconstitution in children following chemotherapy for haematological malignancies: a long-term follow-up", 2010, pp. 201-210.
Vardy, E. R. et al., "Increased Circulating Insulin-like Growth Factor-1 in Late-onset Alzheimer's Disease, Journal of Alzheimer's Disease", 2007, pp. 285-290.
Vieira, F. A. et al., "Skin healing and scale regeneration in fed and unfed sea bream, *Sparus auratus*", 2011, pp. 1-19.
Wang, J. et al., "Caloric restriction attenuates B-amyloid neuropathology in a mouse model of Alzheimer's disease", The FASEB Journal, 2005, pp. 1-18.
Wei, M. et al., "Tor1/Sch9-Regulated Carbon Source Substitution is as Effective as Calorie Restriction in Life Span Extension", May 2009, pp. 1-15, vol. 5 Issue 5.
Williams, M. D. et al., "Hospitalized cancer patients with severe sepsis: analysis of incidence, mortality, and associated costs of care", 2004, pp. R291-R298.
Wu, P. et al., "Calorie restriction ameliorates neurodegenerative phenotypes in forebrain-specific presenilin-1 and presenilin-2 double knockout mice", Neurobiology of Aging, 2007, pp. 1502-1511.
Yahata, T. et al., "Accumulation of oxidative DNA damage restricts the self-renewal capacity of human hematopoietic stem cells", Blood, Sep. 15, 2011, pp. 2941-2950, vol. 118 No. 11.

(56) References Cited

OTHER PUBLICATIONS

Longo, V.D. et al., "Calorie Restriction and Cancer Prevention: Metabolic and Molecular Mechanisms," Trends in Pharmacological Sciences, v. 31, n. 2, 2010, pp. 89-98.

* cited by examiner

| Mouse | Marker | Control (16.5 months) | | FMD (16.5 months, 1st cycle) | | FMD-refed (17 months) |
|---|---|---|---|---|---|---|
| | | | *Effect* | | *Effect* | |
| | Body Weight (g) | 36.62 ± 1.22 | → | 30.04 ± 0.62 *** | - | 36.31 ± 0.71 |
| | Food Intake (kcal) | 14.25 ± 0.45 | → | 2.60 *** | - | 15.68 ± 0.68 |
| | Total Body Fat (rel. volume) *(28 months, 33 cycles)* | 2292 ± 521 | | n.a. | | 808 ± 287 |
| | Subcutan Body Fat (rel. volume) *(28 months, 23 cycles)* | 566 ± 149 | | n.a. | | 369 ± 86 |
| | Visceral Body Fat (rel. volume) *(28 months, 23 cycles)* | 1727 ± 403 | | n.a. | → | 404 ± 187 * |
| Human | Marker | Baseline | | Cycle #1 | | Cycle #3 |
| | | | *Effect* | | *Effect* | |
| | Body Weight (%, compared to Baseline) | 100 | → | 95.69 ± 0.38 *** | → | 94.38 ± 0.35 *** |
| | Trunk Fat (%, compared to Baseline) | 100 | | n.a. | - | 96.89 ± 3.70 |

Table 9. Effects of fasting mimicking diet (FMD) on body composition in mice and humans.

*Fig. 1*

| Mouse | Marker | Control | Effect | FMD | Effect | FMD-refed |
|---|---|---|---|---|---|---|
| | Cancer Incidence (%) | 66.7 | | 0.0 | | 39.3 *** |
| | Onset of Cancer (age in month) | 25.3 ± 0.7 | | n.a | | 28.8 ± 0.7 ** |
| | Glucose (mg/dL) (18 months 3 cycles) | 180.6 ± 4.2 | ↓ | 101.4 ± 8.1 *** | | 170.2 ± 11.4 |
| | IGF-1 (ng/ml) (20.5 months 8 cycles) | 321.8 ± 22.7 | ↓ | 205.8 ± 25.3 *** | | 323.3 ± 28.6 |
| | IGFBP-1 (ng/ml) (20.5 months 8 cycles) | 5.2 ± 0.9 | ↑ | 46.0 ± 2.9 *** | | 5.2 ± 0.6 |

| Human | Marker | Baseline | Effect | Cycle #1 | Effect | Cycle #3 |
|---|---|---|---|---|---|---|
| | Glucose (mg/dL) | 90.6 ± 2.7 | - | 86.5 ± 3.7 | - | 88.3 ± 1.2 |
| | Cortisol (% compared to Baseline) | 100 | - | 203.9 ± 63.3 | - | 134.7 ± 40.4 |
| | IGF-1 (ng/ml) | 145.3 ± 22.7 | ↓ | 104.4 ± 24.1 * | ↓ | 122.7 ± 17.2 * |
| | IGFBP-1 (ng/ml) | 24.8 ± 4.3 | ↑ | 58.3 ± 17.0 * | - | 46.6 ± 16.5 |

Table 10. Effects of fasting mimicking diet (FMD) on blood biomarkers.

*Fig. 2*

| Mouse Marker | Control | FMD-refed Effect |
|---|---|---|
| Inflammation Incidence (%) | 20.0 | ↓ 7.1 * |
| Dermatitis Incidence (%) | 19.6 | ↓ 10.3 * |

Table 11. A fasting mimicking diet reduces inflammation in rodents.

Fig. 3

| Mouse | Tissue | Marker | Middle Age (12 mo) | | Old (28 mo) | | FMD-refed (28 mo, 24 cycles) | |
|---|---|---|---|---|---|---|---|---|
| | | | | Effect | | Effect | | Effect |
| Bone | (Femur) | Mineral Density (mgHA/cm³) | 1995 ± 6 | | 1834 ± 22 ^^^ | ↓ | 1923 ± 9 ^^^, * | ↓ |

Table 12. Effect of fasting mimicking diet (FMD) on bone mineral density.

Fig. 4

Table 13. Effect of fasting mimicking diet (FMD) on liver.

Table 14. Cycles of short-term starvation (STS) or a fasting mimicking diet (FMD) stimulate stem/progenitor cells in mice and human subjects.

| Mouse (after 8 cycles) | Baseline | Chemotherapy | | Fasting + Chemo | |
|---|---|---|---|---|---|
| | | Effect | | Effect | |
| WBC (10⁹/L) | 10.26 ± 4.27 | ↓ | 5.26 ± 1.95 | - | 10.32 ± 5.23 |
| Lymphocytes (10⁹/L) | 7.89 ± 2.09 | ↓ | 2.05 ± 1.22 | - | 7.84 ± 3.17 |
| L/M | 2.65 ± 0.50 | ↓ | 1.36 ± 0.12 | - | 2.11 ± 0.60 |
| Human (after 2 cycles) | Baseline | Chemotherapy | | Fasting + Chemo | |
| | | Effect | | Effect | |
| WBC (10⁹/L) | 6.90 ± 3.69 | ↓ | 3.85 ± 0.72 | - | 6.04 ± 3.31 |
| Lymphocytes (10⁹/L) | 1.96 ± 0.71 | ↓ | 0.94 ± 0.41 | - | 1.98 ± 0.38 |
| L/M | 0.55 ± 0.19 | ↓ | 0.38 ± 0.26 | - | 0.70 ± 0.51 |

Table 15. Cycles of fasting improve the hematopoietic regeneration in mice and human subjects after chemotherapy induced myelo-suppression.

Fig. 7

| Mouse (12-20 cycles of FMD) | | | | |
|---|---|---|---|---|
| Age (month) | Control | | FMD | |
| | Effect | L/M | Effect | L/M |
| 4 | | 2.96 ± 1.14 | | |
| 16 | ↓ | 0.55 ± 0.28 | - | 1.27 ± 0.76 |
| 20 | ↓ | 0.51 ± 0.13 | - | 2.63 ± 3.27 |
| Human (1 complete cycle of FMD) | | | | |
| Age (years) | Control | | FMD | |
| | Effect | L/M | Effect | L/M |
| <20 | | 0.52 ± 0.22 | | - |
| 20-40 | ↓ | 0.41 ± 0.13 | - | 0.46 ± 0.13 |
| 40-60 | ↓ | 0.39 ± 0.11 | - | 0.50 ± 0.13 |
| >60 | ↓ | 0.33 ± 0.04 | | not measured |

Table 16. Cycles of a fasting mimicking diet (FMD) improve the hematopoietic regeneration in mice and human subjects and delay age-dependent myelo-depression.

Fig. 8

Table 17. Effect of fasting mimicking diet (FMD) on the brain and cognitive functions

| Body Weight | Day1 | Day2 | Day3 | Day4 | Day5 | Δ5-day[1] | Δ5-day[2] |
|---|---|---|---|---|---|---|---|
| | kcal/day | | | | | | |
| ≥200 lbs | 1170 | 828 | 768 | 810 | 833 | -5591 | -9591 |
| 151-200 lbs | 1134 | 790 | 737 | 774 | 795 | -5772 | -7772 |
| ≤150 lbs | 1098 | 751 | 706 | 738 | 756 | -5952 | -5952 |
| | kcal/lb | | | | | | |
| 250 lbs | 4.7 | 3.3 | 3.1 | 3.2 | 3.3 | | |
| 200 lbs | 5.7 | 3.9 | 3.7 | 3.9 | 4.0 | | |
| 150 lbs | 7.3 | 5.0 | 4.7 | 4.9 | 5.0 | | |
| | kcal/kg | | | | | | |
| 113 kg | 10.3 | 7.3 | 6.8 | 7.1 | 7.3 | | |
| 91 kg | 12.5 | 8.7 | 8.1 | 8.5 | 8.8 | | |
| 68 kg | 16.1 | 11.0 | 10.4 | 10.8 | 11.1 | | |

[1] based on a 2,000 calorie per day diet
[2] based on 2,800, 2,400, and 2,000 calorie diets for person's weight ≥200, 150-200, and ≤150 lbs, respectively.

Table 18. The fasting mimicking diet (FMD). Prolon, was developed by the L-Nutra to induce a fasting-like response while maximizing nourishment.

*Fig. 12*

|  | Day 1 | Day 2,3,4,5 |
|---|---|---|
| Total Calorie | 1152 | 809 |
| Fat | 56% | 46% |
| Carbohydrate | 34% | 46% |
| Sugar | 10% | 9% |
| Protein | 10% | 9% |

*Table 19. The macronutrient content for each day of the 5 day FMD regimen based on an average 180- 200 lbs person.*

*Fig. 13*

|  | Unit | Day 1 | % DV* | Day 2,3,4,5 | % DV* | Ave % DV* |
|---|---|---|---|---|---|---|
| Protein | g | 29 |  | 18 |  |  |
| Fat | g | 72 |  | 41 |  |  |
| Carb (by diff) | g | 98 |  | 91 |  |  |
| From Sugars | g | 29 |  | 17.6 |  |  |
| Dietary Fiber | g | 22 | 86% | 14 | 56% | 62% |
| Calcium | mg | 604 | 60% | 426 | 43% | 46% |
| Iron | mg | 13 | 77% | 10 | 55% | 60% |
| Magnesium | mg | 387 | 97% | 230 | 58% | 65% |
| Phosphorus | mg | 390 | 39% | 276 | 28% | 30% |
| Potassium (K) | mg | 2519 | 72% | 1795 | 51% | 55% |
| Sodium (Na) | mg | 2427 | 101% | 1750 | 73% | 79% |
| Zinc | mg | 7 | 46% | 4.2 | 28% | 32% |
| Copper | mg | 1.5 | 76% | 1.2 | 59% | 63% |
| Manganese | mg | 3 | 148% | 1.9 | 95% | 105% |
| Selenium | mcg | 7 | 10% | 5.3 | 8% | 8% |
| Vit A | IU | 39254 | 785% | 27549 | 561% | 598% |
| Vit C | mcg | 236 | 393% | 137 | 229% | 261% |
| Vit B1 Thiamin | mg | 4 | 209% | 2.2 | 113% | 132% |
| Vit B2 Riboflavin B2 | mg | 3.8 | 191% | 2 | 109% | 126% |
| Vit B3 Niacin | mg | 28.5 | 143% | 18 | 92% | 102% |
| Vit B5 Pantothenic Acid | mg | 1.2 | 12% | 1.0 | 10% | 10% |
| Vit B6 Pyridoxal phosphate | mg | 4.0 | 200% | 2.2 | 111% | 129% |
| Vit B9 Folate | mg | 479 | 120% | 317 | 79% | 87% |
| B12 Cobalamin | mcg | 18 | 227% | 16 | 227% | 227% |
| Vit D | IU | 952 | 238% | 952 | 238% | 238% |
| Vit E | mcg | 25 | 127% | 16 | 80% | 89% |
| Vit K | mg | 1795 | 2243% | 1110 | 1387% | 1559% |

Table 20. The micronutrient content for each day of the 5 day FMD regimen based on an average 180-200 lbs person.

*Fig. 14*

METHODS AND FORMULATIONS PROMOTING TISSUE/ORGAN REGENERATION, LONGEVITY AND HEALTHSPAN

CROSS-REFERENCE TO RELATED APPLICATIONS

This application claims the benefit of U.S. provisional application Ser. No. 61/716,676 filed Oct. 22, 2012, Ser. No. 61/736,308 filed Dec. 12, 2012, and Ser. No. 61/746,787 filed Dec. 28, 2012, the disclosures of which are incorporated in their entirety by reference herein.

STATEMENT REGARDING FEDERALLY SPONSORED RESEARCH OR DEVELOPMENT

The invention was made with Government support under Contract Nos. PO1AG034906, P01 AG 034906-01, and PO1AG020642. The Government has certain rights to the invention.

TECHNICAL FIELD

The present invention relates to a method of promoting tissue and/or organ regeneration.

BACKGROUND

Regenerative therapies may be used in the replenishment of damaged tissues/organs caused by chemotherapy or radiotherapy, associated with degenerative diseases or aging.

Conventional regenerative therapies commonly rely on the introduction of donor-derived regenerative cells and/or the administration of biologically active molecules that stimulate regeneration. Besides ethical issues, technical and safety challenges in stem cell isolation, maintenance, expansion, donor-recipient matching and transplantation persist and limit the usefulness and practicability of existing conventional regenerative therapies. Conventional therapies typically have not utilized dietary protocol has effective treatments for patients in need of tissue regeneration. Although diet has been known to provide tissue protection in various circumstances. The major limitation of conventional therapies is the lack of a coordinated regenerative process that is reminiscent of the developmental process leading to tissue generation in the embryo. The formulations and methods described in this application can overcome these limitations.

Caloric Restriction (CR) without malnutrition is effective in protecting the brain against aging and oxidative stress (Martin et al. 2006). Several studies support a beneficial role for this dietary intervention in protecting against age dependent decay in cognitive performance in rodents (Fontan-Lozano et al. 2008). In addition CR shows remarkable neuroprotective properties against neurodegenerative diseases including stroke, Parkinson's disease (PD), Huntington's disease (HD) and Alzheimer's Disease (AD) in several animal models (Mattson 2005; Patel et al. 2005).

Recent studies in different AD mouse models reported that reducing food intake can diminish AD-related neuropathologies and cognitive dysfunction. For example, CR reduces the progression of β amyloid (Aβ) deposition in the hippocampus and cerebral cortex of AD mice carrying mutations for FAD (Wang et al. 2005), APP (amyloid precursor protein) and APP+PS-1 (presenilin 1) (Patel et al. 2005; Mouton et al. 2009). CR ameliorates neurodegenerative phenotypes assessed by object recognition and contextual fear conditioning tests in cDKO (conditional double knockout) AD mice (Wu et al. 2008). Mattson and coworkers have shown that CR can also ameliorate age-related memory impairment and decrease Aβ and phosphorylated tau accumulation in a triple transgenic mouse (3×Tg-AD) that overexpress mutations linked to AD (PS-1, APP) and frontotemporal dementia (tau) (Halagappa et al. 2007). Also studies in human populations suggest that diet plays an important role in AD and reduced food intake may protect against this pathology. For example, an epidemiological study by Luchsinger and colleagues provided evidence that individuals with a low calorie intake have a reduced risk of developing AD (Luchsinger et al. 2002).

Among the large number of metabolic and physiological changes caused by CR, reduction of growth hormone (GH)/insulin-like factor (IGF-1) signaling axis may be important for its protective effects (Fontana et al. 2010). Circulating IGF-1 is a hormone produced primarily by the liver that regulates energy metabolism, cell proliferation, cell differentiation, body size and longevity. IGF-1 levels are regulated by calorie and/or protein availability and long-term CR decreases serum IGF-1 concentration by approximately 30-40% in rodents (Thissen et al. 1994) but not in humans unless protein intake is also reduced (Fontana et al. 2008). Mutations that decrease the activity of the growth hormone receptor (GHR)/IGF-1 signaling pathways, similarly to CR, can extend longevity and enhance stress resistance in a wide range of organisms and tissues (Kenyon 2005) including mammalian central nervous system (CNS) (Parrella & Longo 2010). Although the overlap between the pathways altered by these nutritional and genetic interventions seems to be only partial, it has been proposed that the decline in IGF-1 levels can mediate part of the beneficial effects produced by CR (Sonntag et al. 1999). In support of this theory, recently it has been shown that reducing IGF-1 signaling in an AD mouse carrying APP and PS-1 mutations protects against Alzheimer's-like disease symptoms including cognitive deficits and neuroinflammation (Cohen et al. 2009). Notably, GH receptor-deficient (GHRD) mice and humans are protected from major diseases (Guevara-Aguirre et al. 2011; Ikeno et al. 2009; Masternak et al. 2009) and GHRD mice consistently live 40% longer (Coschigano et al. 2000). Moreover, a study carried out on a cohort of Ashkenazi Jewish centenarians identified genetic alterations on human IGF-1 receptor (IGF-1R) that result in reduced IGF-1 signaling among the centenarians compared to controls (Suh et al. 2008). On the other hand the effect of IGF-1 or IGF-1R deficiency on lifespan is inconsistent (Bokov et al. 2011), suggesting that reduced IGF-1 may be only one of the mediators of the anti-aging effects of GHR deficiency.

Protein and amino acid (AA) availability is fundamental in regulating IGF-1 gene expression. Moreover, protein restriction not only decreases IGF-1 production rate, but also accelerates its clearance, regulates IGF-1 interaction with IGF binding proteins (IGFBPs) and attenuates IGF-1 biological actions (Ketelslegers et al. 1995). Because CR is very difficult to maintain, and is unavoidably associated with weight loss, loss of sex drive, hunger, feeling cold at normal room temperature and possible immune system side effects.

Accordingly, there is a need for dietary protocols to alleviate symptoms of Alzheimer's disease and/or other degenerative diseases and to promote tissue regeneration.

SUMMARY OF THE INVENTION

The present invention solves one or more problems of the prior art by providing in at least one embodiment a method of treating a subject in need of diet modification. The method includes steps of identifying a subject in need of diet modification and administering a first diet to the subject for a first time period. The first diet provides 4.5 to 7 kilocalories per pound of subject for a first day and 3 to 5 kilocalories per pound of subject per day for a second to fifth day of the first diet. The first diet includes less than 30 g of sugar on the first day; less than 20 g of sugar on the second to fifth days; less than 28 g of proteins on the first day; less than 18 g of proteins on days the second to fifth days; 20 to 30 grams of monounsaturated fats on the first day; 10 to 15 grams of monounsaturated fats on the second to fifth days; between 6 and 10 grams of polyunsaturated fats on the first day; 3 to 5 grams of polyunsaturated fats on the second to fifth days; less than 12 g of saturated fats on the first day; less than 6 grams of saturated fats on the second to fifth days; and 12 to 25 grams of glycerol per day on the second to fifth days.

In another embodiment, a diet package implementing the diet protocol set forth above is provided. The diet package includes a first set of rations for a first diet to be administered for a first time period to a subject, the first diet providing from 4.5 to 7 kilocalories per pound of subject for a first day and 3 to 5 kilocalories per pound of subject per day for a second to fifth day of the first diet. The diet package includes rations that provide less than 30 g of sugar on the first day; less than 20 g of sugar on the second to fifth days; less than 28 g of proteins on the first day; less than 18 g of proteins on days the second to fifth days; 20 to 30 grams of monounsaturated fats on the first day; 10 to 15 grams of monounsaturated fats on the second to fifth days; between 6 and 10 grams of polyunsaturated fats on the first day; 3 to 5 grams of polyunsaturated fats on the second to fifth days; less than 12 g of saturated fats on the first day; less than 6 grams of saturated fats on the second to fifth days; and 12 to 25 grams of glycerol per day on the second to fifth days.

In another embodiment, a method of increasing the number of stem cells and/or progenitor cells in a subject is provided. In accordance with the method, a subject requiring increased numbers of stem cells and/or progenitor cells is identified and a reduction in protein kinase A (PKA) activity is induced.

In another embodiment, a method of alleviating a symptom in an immuno-compromised subject or boosting the immune status of a subject is provided. The method includes a step of identifying an immuno-compromised subject or a subject desiring an improved immune status and then inducing reduction in PKA activity in the immuno-compromised subject.

In yet another embodiment, a method of transferring cell hematopoietic stem/progenitor cells to a subject is provided. The method includes a step of identifying an immuno-compromised subject. A reduction in protein kinase A activity and/or IGF-I receptor level is induced in bone marrow or stem cells of a donor. After the treatment, the cells are then grafted into the immuno-compromised or other subject in need of regeneration.

In still another embodiment, a method of promoting growth of regenerative cells is provided. The method includes a step of administering a diet protocol to a subject for a first time period and a second time period. During the first time period, a reduced caloric diet is provided to the subject with at least 50 percent calories derived from fat. During the second time period, a second reduced caloric diet of at most 900 kcal/day is provided to the subject. Optionally, the regenerative cells are isolated from the subject and transferred to a recipient.

In still another embodiment, a method of alleviating a symptom of Alzheimer's Disease is provided. The method includes a step of administering an amino acid specific diet having certain amino acids. In this embodiment, a long-term alternation of cycles of a normal and a protein restricted diet (protein restriction cycles, PRC) is found to reduce GHR/IGF-1 levels/signaling and ameliorate the AD-like symptoms in a 3×Tg-AD mouse that accumulates both Aβ and tau pathologies.

BRIEF DESCRIPTION OF THE DRAWINGS

FIG. 1 provides Table 9 showing effects of a fasting mimicking diet (FMD) on body composition in mice and humans. In 16.5 months old female BALB/c mice the body weight was routinely measured. One cycle of FMD significantly reduced the bodyweight by 18% compared to ad lib fed controls. After re-feeding, no significant difference in weight remained, indicating that all mice recovered from the dietary regime after completion of the first cycle. The decrease in weight can be attributed to the relatively low calorie intake during the FMD cycle which was reduced by ~80% when considering all 4 days of the cycle. No difference in calorie intake was observed between diet and control groups, since mice compensated after FMD feeding by a slight over-consumption during re-feeding; thus normalizing the calorie intake. The long-term effects of the FMD regimen on total body fat as well as the subcategorized fat deposits (subcutan and visceral) were evaluated by X-ray computed tomography (CT) scans. At 28 months of age and after completion of 23 FMD cycles, total and visceral body fat, which is closely related to pathologies associated with obesity, were reduced in the FMD mice. Only a minor effect on subcutaneous fat deposits was measurable. In humans, after one and three cycles of a fasting-mimicking diet, body weight (as % compared to the baseline values prior to the start of the FMD) were significantly reduced and have thus similar effects as seen in the preclinical experiments. The relative trunk fat percentage of human subjects upon the completion of three cycles of FMD was evaluated by "Dual-energy X-ray absorptiometry" (DEXA). All data presented as mean±SEM. *p<0.05, p<0.01, *p<0.001 compared to Control or Baseline;

FIG. 2 provides Table 10 showing effects of a fasting mimicking diet on blood biomarkers in mice and humans. Compared to ad lib fed control animals, mice maintained on the FMD diet starting at 16.5 months of age had a significantly reduced cancer incidence over their lifespan. In addition, the cancer development was significantly delayed in the FMD fed mice. Considering the maximal lifespan of the C57BL/6 mouse strain of about 33 months (data not shown), the FMD diet delayed the onset of cancer development by 3.5 months or 10%. Glucose and IGF-1, which we and others had shown to promote tumor development and progression, were significantly reduced during the FMD regimen. IGFBP-1, which binds and reduces the bioavailability of IGF-1, was increased; thereby further reducing IGF-1 signaling. In humans, no data for cancer incidence or development is available. Similarly to the preclinical data, IGF-1 was reduced after the first and third FMD cycle. IGFBP-1 levels were increased. All data presented as mean±SEM. *p<0.05, p<0.01, * p<0.001 compared to Control or Baseline;

FIG. 3 provides Table 11 illustrating that a fasting mimicking diet reduces inflammation in rodents. Compared to ad lib fed control animals, mice maintained on the FMD diet starting at 16.5 months of age had a significantly reduced incidence of inflamed tissues detected at necroscopy. Inflamed tissues included among others the liver and reproductive tract of female mice (not shown). C57BL/6 mice (both genders) are particularly prone to developing a progressively worsening ulcerating dermatitis. Female mice fed with the FMD diet displayed a 50% reduction in dermatitis incidence over their lifespan compared to the ad lib fed control animals (10.3% vs. 19.6%, respectively). *$p<0.05$ compared to Control;

FIG. 4 provides Table 12 showing the effect of a fasting mimicking diet on bone mineral density. Bone mineral density [in mg Hydroxyapatite (HA)/cm3] of the femoral bone was analyzed by X-ray computed tomography (CT)-scans in control-fed animals at 12 and 28 months of age, as well as 7 days after the re-feeding of mice in the FMD cohort in vivo at 28 month of age (FMD-refed). A reduction in bone mineral density was observed in C57BL/6 mice from 12 to 28 months of age. However, mice fed with the FMD diet starting at 16.5 month of age showed a significantly reduced loss of bone mineral density when compared to their ad lib fed and age-matched counterparts. All data presented as mean±SEM. ^^^ $p<0.001$ compared to middle age group. *$p<0.05$ compared to Old;

FIG. 7 provides Table 15 showing cycles of fasting improve the hematopoietic regeneration in mice and human subjects after chemotherapy induced myelosuppression. The hematological profile of mice and human subjects after cycles of chemotherapy treatments with or without pre-chemo fasting is shown. Absolute white blood cell (WBC) counts and lymphocyte counts were measured with an automated hemato-analyzer. The lymphoid-myeloid ratio (L/M), an indicator of immune system homeostasis, was calculated as the total number of lymphocytes/number of myeloid cells per individual. In mice and humans chemotherapy treatment reduced the number of WBCs, lymphocytes and the L/M ratio. The combination of fasting prior to chemotherapy ameliorated these effects and maintained all measured parameters at normal levels. All data presented as mean±SEM.;

FIG. 8 provides Table 16 showing cycles of a fasting mimicking diet improve the hematopoietic regeneration in mice and human subjects and delay age-dependent myelodepression. The lymphoid-myeloid ratio (L/M), an indicator of immune system homeostasis, decreases with age in mice and human subjects. In mice, starting FMD feeding at an age of 10 months delayed the myelo-depressing effects and no significant age-dependent reduction could be measured. In humans, one cycle of FMD re-established the L/M ratio in various age groups. The reference L/M ratio for young animals and humans is shown in bold red. All data were presented as mean±SEM;

FIG. 12 provides Table 18 showing the Calorie overview of the fasting mimicking diet adjusted to human subjects. The fasting mimicking diet (FMD), Prolon, induces a fasting-like response while maximizing nourishment. The consumed calories for each one of the 5 days of the diet are shown, as well as the adjusted kcal per pound and kilogram of body weight. The reduction in calories consumed during the 5 day dietary regimen (Δ5-day) is shown as either 1) based on a 2,000 calorie per day diet, or 2) based on 2,800, 2,400, and 2,000 calorie diets for person's weight≥200, 150-200, and ≤150 lbs, respectively.;

FIG. 13 provides Table 19 showing the defined macronutrient content for each diet day adjusted to a 180-200 lbs human subject. The macronutrient content for each day of the 5 day FMD regimen based on an average 180-200 lbs person. Caloric intake on day 1 of the diet is less reduced compared to the following days (2-5) to allow the body to adjust to the low calorie consumption. % of calories contributed by fat, carbohydrate (by sugar in detail) and protein for each day of the Prolon regimen is presented;

FIG. 14 provides Table 20 showing the defined micronutrient content for each diet day adjusted to a 180-200 lbs human subject in a variation of the invention. The micronutrient content for each day of the 5 day FMD regimen based on an average 180-200 lbs person. Percent of the daily value (% DV) is calculated based on a 2,000 calorie diet. * for some of the micronutrients, DV is not defined; values shown are based on the reference daily intake (RDI);

DETAILED DESCRIPTION

Figure 5:
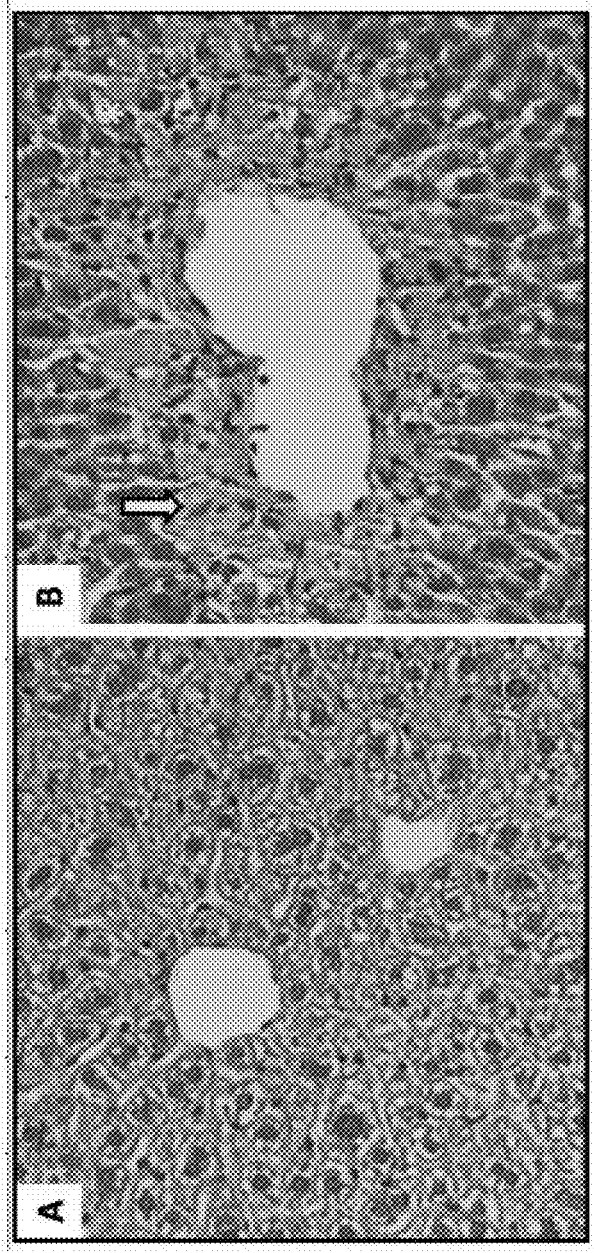
FIG. 5 provides Table 13 and pictures showing the effect of a fasting mimicking diet on liver regeneration. In comparison to 20-22.5 months old mice from ad lib fed control, animals fed with the experimental FMD diet starting at 16.5 months of age (=7-11 FMD cycles) had significantly reduced liver weight and lose about 35% of the original liver mass at the end of the FMD regimen. Alanine aminotransferase (ALT) level, a clinical diagnostic marker for the evaluation of hepatocellular injury and liver health, was elevated at the end of the FMD regimen but returned to normal levels within 7 days of refeeding. The increase in ALT is consistent with the observation that FMD caused hepatocytes to become atrophic (B, asterisks). However, upon refeeding the liver weight returns to, and even exceeds (+10%), normal weight. Liver H&E staining of the control (A) and the FMD group 24 h after refeeding (B) showed the infiltration of unorganized cells (arrow) around the vein indicating liver regeneration and repopulation with "young" hepatocytes immediately after refeeding. All data presented as mean±SEM. **$p<0.01$ compared to Control.

Reference will now be made in detail to presently preferred compositions, embodiments and methods of the present invention. The Figures are not necessarily to scale. The disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

This invention is not limited to the specific embodiments and methods described below, as specific components and/or conditions may, of course, vary. Furthermore, the terminology used herein is used only for the purpose of describing particular embodiments of the present invention and is not intended to be limiting in any way.

As used in the specification and the appended claims, the singular form "a," "an," and "the" comprise plural referents unless the context clearly indicates otherwise. For example, reference to a component in the singular is intended to comprise a plurality of components.

The term "essential amino acid" refers to amino acids that cannot be synthesized by an organism. In humans, essential amino acids include isoleucine, leucine, lysine, methionine, phenylalanine, threonine, tryptophan, valine. In addition, the following amino acids are also essential in humans under certain conditions—histidine, tyrosine, and selenocysteine.

The terms "kilocalorie" (kcal) and "Calorie" refer to the food calorie. The term "calorie" refers to the so-called small calorie.

The term "subject" refers to a human or animal, including all mammals such as primates (particularly higher primates), sheep, dog, rodents (e.g., mouse or rat), guinea pig, goat, pig, cat, rabbit, and cow.

Embodiments of the present invention relate to methods for tissue and/or organ regeneration, and, in particular, to stem cell-based regeneration. As will be detailed herein below, and without wanting to be limited to any particular theory, it is believed that the present invention in one or more embodiments may enhance the availability and functionality of regenerative cells including stem cells and progenitor cells and promotes tissue/organ regeneration and reconstitution, and in particular, hematopoietic stem/progenitor cells and other immune cells. In a variation, the regenerative cells include brain cells, muscle cells, liver cells, and cells derived therefrom. Inhibition of growth hormone receptor (GHR), Insulin-like growth factor 1 (IGF-I), insulin-like growth factor 1 (IGF-1) receptor (IGF-IR), and protein kinase A (PKA) enhances the availability and functionality of regenerative cells in mammals. Such inhibition is achieved by gene silencing, pharmaceutical inhibition, and administering of low calorie dietary protocols as set forth below. This tissue and/or regeneration is applicable to both residential regeneration, wherein the donor to and the recipient of the regenerative cells are the same individual, and transplant regeneration, where the donor to and the recipient of the regenerative cells are two different individuals. In this regard, the present invention is particularly advantageous in effectuating the residential regeneration in a relatively less offensive approach, which can be more cost effective and reduce the occurrences of certain issues including donor-recipient matching difficulties.

In an embodiment, a method for modifying a subject's diet is provided. The method includes a step of identifying a subject in need of diet modification. A first diet is administered for a first time period to the subject. As used herein, sometimes the first diet of this embodiment is referred to as a fasting mimicking diet (FMD). In a refinement, the first diet provides from 4.5 to 7 kilocalories per pound of subject for a first day (day 1) and then 3 to 5 kilocalories per pound of subject per day for a second to fifth day (days 2-5) of the first diet. A second diet is administered to the subject for a second time period. In a refinement, the second diet provides an overall calorie consumption that is within 20 percent of a subject's normal calorie consumption for 25 to 26 days (e.g., immediately) following the first diet. In one refinement, the subject is in need of weight loss with method resulting in weight loss. In another refinement, the subject is in need of tissue regeneration with the method resulting is such tissue regeneration. Characteristically, it is observed that the level of IGF-I decreases and the level of IGFBP1 increases. In a refinement, the method of this embodiment is repeated from 1 to 5 times. In another refinement, the method of this embodiment is repeated from 2 to 3 times. In still another refinement, the method of this embodiment is repeated for a period of years or throughout the subject's entire life. In another refinement, the combination of the first diet and the second diet provide the subject with a total number of calories within 10 percent of the subject's normal caloric intake. In another refinement, the combination of the first diet and the second diet provides the subject with a total number of calories within 5 percent of the subject's normal caloric intake. In still another refinement, the combination of the first diet and the second diet provides the subject with a total number of calories within 1 percent of the subject's normal caloric intake.

In the context of the present embodiment, a subject in need of diet modification includes subject requiring weight reduction. In other variations, a subject in need of diet modification includes subjects in need of stem cell, progenitor cell and embryonic-like stem cell regeneration; subjects in need of WBC regeneration and a balanced lymphoid/myeloid ratio; subjects in need of reversal of immunosuppression, immunodeficiency and immunodepression; subjects in need of neurogenesis and improvement of cognitive performance both related to short-term memory, long-term memory and motor coordination in both young and old mammals; subjects in need of reversal of cognitive decline; subjects having cancer; subjects having an inflammatory disease (e.g., skin dermatitis); subjects having loss of bone density (e.g., osteoporosis); and subjects having liver damage. Examples of such symptoms of Alzheimer's Disease include, but are not limited to, impairment of learning and memory, speech difficulties, agnosia, apraxia, paraphasias, short term memory loss, and the like. Examples of such symptoms of immunosuppression, immunodeficiency and immunodepression include, but are not limited to, susceptibility to infections and susceptibility to cancer. Examples of such symptoms of inflammatory disease include, but are not limited to, inflammation, swelling, redness, pain, calor, and loss of function. Examples of such symptoms of liver damage include, but are not limited to, elevation of ALT, elevation of ALP, bilirubin, itching, jaundice, neoplasm, hepatocellular necrosis, zonal necrosis, and the like.

In a refinement, the method reduces the risk for loss of bone density or reduces a symptom of bone loss. In still another example, the method reduces the risk of liver damage or alleviates a symptom of liver damage. In a further refinement, the method with respect to assessing liver damage further includes a step of monitoring the levels of liver markers. In particular, the levels of aminotransferase (ALT) and aspartate aminotransferase (AST) are measured in a blood test as is known to one skilled in the art.

In another refinement, the subject requires stem cell, progenitor cell or embryonic-like stem cell regeneration. In still another refinement, the subject requires white blood cell (WBC) regeneration and/or a balanced lymphoid/myeloid ratio analogous to that observed in young and healthy mammals/humans. In still another refinement, the subject is at a risk for immunosuppression, immunodeficiency and immunodepression or the subject has one of these conditions and the method alleviates at least one symptom thereof.

In yet another refinement, the subject is in need of neurogenesis and improvement of cognitive performance both related to short-term memory, long-term memory and motor coordination in both young and old mammals. Subject in this category include those in need of reversal of cognitive decline. Examples of such cognitive conditions include, but are not limited to Alzheimer's Disease and related conditions.

In a variation, the fasting mimicking diet (FMD) program involves completely substituting a subject's diet for 5 days. During this 5 day period, subjects consume plenty of water. For healthy subjects of normal weight (Body Mass Index or BMI between 18.5-25), the diet is consumed once a month (5 days on the diet and 25-26 days on their normal diet) for the first 3 months and every 3 months thereafter (5 days every 3 months). The weight of the subject is measured and the subject must regain at least 95% of the weight lost during the diet before the next cycle is begun. Subjects with BMI of less than 18.5 should not undertake the FMD unless recommended and supervised by a physician. The same regimen (once every month for 3 months followed by once every 3 months thereafter) can be adopted for the treatment, or in support of the treatment, of all of the conditions presented in the patent applications.

A refinement of the FMD for overweight subjects (BMI: 25-30), entails following the diet once/month or as frequently as twice/month until the ideal weight is reached, while under medical supervision. In a further refinement of the FMD for obese subjects (BMI>30), physicians recommend consumption of the diet as frequently as once a week (5 days on the diet, 2 days off) with the appropriate medical supervision.

The consumption guidelines for the FMD include Nutrition Facts relative to calories, macronutrients and micronutrients. Calories are consumed according to the user's body weight. Total calorie consumption is 4.5-7 calorie per pound (or 10-16 calorie per kilogram) for day 1 and 3-5 calorie per pound (or 7-11 calorie per kilogram) for day 2 to 5. FIGS. 12-14 provides listings of the nutrients for day one through day five. In addition to the macronutrients, the diet should contain less than 30 g of sugar on day 1 and less than 20 g of sugar on days 2-5. The diet should contain less than 28 g of proteins on day 1 and less than 18 g of proteins on days 2-5. The diet should contain between 20 and 30 grams of monounsaturated fats on day 1 and 10-15 grams of monounsaturated fats on days 2-5. The diet should contain between 6 and 10 grams of polyunsaturated fats on day 1 and 3-5 grams of polyunsaturated fats on days 2-5. The diet should contain less than 12 g of saturated fats on day 1 and less than 6 grams of saturated fats on days 2-5. Typically, the fats on all days are derived from a combination of the following: Almonds, Macadamia Nuts, Pecans, Coconut, Coconut oil, Olive Oil and Flaxseed. In a refinement, the FMD diet includes over 50% of the recommended daily value of dietary fiber on all days. In the further refinement, the amount of dietary fiber is greater than 15 grams per day on all five days. The diet should contain 12-25 grams of glycerol per day on days 2-5. In a refinement, glycerol is provided at 0.1 grams per pound body weight/day.

In a variation, the FMD includes the following micronutrients (at least 95% non-animal based): over 5,000 IU of vitamin A per day (days 1-5); 60-240 mg of vitamin C per day (days 1-5); 400-800 mg of Calcium per day (days 1-5); 7.2-14.4 mg of Iron per day (days 1-5); 200-400 mg of Magnesium per day (days 1-5); 1-2 mg of copper per day (days 1-5); 1-2 mg of Manganese per day (days 1-5); 3.5-7 mcg of Selenium per day (days 1-5); 2-4 mg of Vitamin B1 per day (days 1-5); 2-4 mg of Vitamin B2 per day (days 1-5); 20-30 mg of Vitamin B3 per day (days 1-5); 1-1.5 mg of Vitamin B5 per day (days 1-5); 2-4 mg of Vitamin B6 per day (days 1-5); 240-480 mcg of Vitamin B9 per day (days 1-5); 600-1000 IU of Vitamin D per day (days 1-5); 14-30 mg of Vitamin E per day (days 1-5); over 80 mcg of Vitamin K per day (days 1-5); 16-25 mcg Vitamin B12 are provided during the entire 5-day period; 600 mg of Docosahexaenoic acid (DHA, algae-derived) are provided during the entire 5-day period. The FMD diet provides high micronutrient content mostly (i.e., greater than 50 percent by weight) from natural sources including: Kale, Cashews, Yellow Bell Pepper, Onion, Lemon Juice, Yeast, Turmeric. Mushroom, Carrot, Olive Oil, Beet Juice, Spinach, Tomato, Collard, Nettle, Thyme, Salt, Pepper, Vitamin B12 (Cyanocobalamin), Beets, Butternut Squash, Collard, Tomato, Oregano, Tomato Juice, Orange Juice, Celery, Romaine Lettuce, Spinach, Cumin, Orange Rind, Citric Acid, Nutmeg, Cloves, and combinations thereof. Table 1 provides an example of additional micronutrient supplementation that can be provided in the FMD diet:

TABLE 1

Micronutrient Supplementation

| | Supplement | Formula | Amount | Amount Range | Unit |
|---|---|---|---|---|---|
| Vit A | | | 1250 IU | 900-1600 | IU |
| Vit C | Ascorbic Acid | $C_6H_8O_6$ | 15.0000 | 10-20 | mg |
| Ca | Calcium Carbonate | $CaCO_3$ | 80.0000 | 60-100 | mg |
| Fe | Ferrous Fumarate | $C_4H_2FeO_4$ | 4.5000 | 3-6 | mg |
| Vit D3 | Cholecalciferol | $C_{27}H_{44}O$ | 0.0025 | 0.001-0.005 | mg |
| Vit E | dl-Alpha Tocopheryl Acetate | $C_{29}H_{50}O_2$ | 5.0000 | 3-7 | mg |
| Vit K | Phytonadione | | 0.0200 | 0.1-0.04 | mg |
| Vit B1 | Thiamine Mononitrate | $C_{12}H_{17}N_5O_4S$ | 0.3750 | 0.15-0.5 | mg |
| Vit B2 | Riboflavin E101 | $C_{17}H_{20}N_4O_6$ | 0.4250 | 0.2-0.6 | mg |
| Vit B3 | Niacinamide | $C_6H_6N_2O$ | 5.0000 | 3-7 | mg |
| Vit B5 | Calcium Pantothenate | $C_{18}H_{32}CaN_2O_{10}$ | 2.5000 | 1.5-4.0 | mg |
| Vit B6 | Pyridoxine Hydrochloride | $C_8H_{11}NO_3 \cdot HCl$ | 0.5000 | 0.3-0.7 | mg |
| Vit B7 | Biotin | $C_{10}H_{16}N_2O_3S$ | 0.0150 | 0.01-0.02 | mg |
| Vit B9 | Folic Acid | $C_{19}H_{19}N_7O_6$ | 0.1000 | 0.07-0.14 | mg |
| Vit B12 | Cyanocobalamin | $C_{63}H_{88}CoN_{14}O_{14}P$ | 0.0015 | 0.001-0.002 | mg |
| Cr | Chromium Picolinate | $Cr(C6H4NO2)3$ | 0.0174 | 0.014-0.022 | mg |
| Cu | Cupric Sulfate | $CuSO4$ | 0.2500 | 0.18-0.32 | mg |
| I | Potassium Iodide | KI | 0.0375 | 0.03-0.045 | mg |
| Mg | Magnesium Oxide | MgO | 26.0000 | 20-32 | mg |
| Mn | Manganese Sulfate | $MnSO_4$ | 0.5000 | 0.3-0.7 | mg |
| Mo | Sodium Molybdate | $Na_2MoO_4$ | 0.0188 | 0.014-0.023 | mg |
| Se | Sodium Selenate | $Na_2O_4Se$ | 0.0175 | 0.014-0.023 | mg |
| Zn | Zinc Oxide | ZnO | 3.7500 | 3-5 | mg |

In another embodiment, a diet package for implemented the diet protocol set forth above is provided. The diet package includes a first set of rations for a first diet to be administered for a first time period to a subject, the first diet providing from 4.5 to 7 kilocalories per pound of subject for a first day and 3 to 5 kilocalories per pound of subject per day for a second to fifth day of the first diet. The diet package includes rations that provide less than 30 g of sugar on the first day; less than 20 g of sugar on the second to fifth days; less than 28 g of proteins on the first day; less than 18 g of proteins on days the second to fifth days; 20 to 30 grams of monounsaturated fats on the first day; 10 to 15 grams of monounsaturated fats on the second to fifth days; between 6 and 10 grams of polyunsaturated fats on the first day; 3 to 5 grams of polyunsaturated fats on the second to fifth days; less than 12 g of saturated fats on the first day; less than 6 grams of saturated fats on the second to fifth days; and 12 to 25 grams of glycerol per day on the second to fifth days. In a refinement, the diet package further includes sufficient rations to provide the micronutrients set forth above. In a further refinement, the diet package provides instructions providing details of the methods set forth above.

In another embodiment, a method for inhibiting GHR, IGF-I, IGF-IR or PKA is provided. The method of this embodiment includes a step of identifying a subject in need of inhibition of GHR, IGF-I, IGF-IR or PKA and then inhibiting at least one of GHR, IGF-I, IGF-IR or PKA. In a refinement, at least two of GHR, IGF-I, IGF-IR or PKA are inhibited. In another refinement, at least three of GHR, IGF-I, IGF-IR or PKA are inhibited. In still another embodiment, all of GHR, IGF-I, IGF-IR or PKA are inhibited.

In the context of the present embodiment, a subject in need of inhibition of GHR, IGF-I, IGF-IR or PKA includes subjects in need of diet modification or weight reduction. Indeed, the diet protocols set forth above accomplishes inhibition of GHR, IGF-I, IGF-IR or PKA. In other variations, a subject in need of GHR, IGF-I, IGF-IR or PKA inhibition includes subjects in need of stem cell, progenitor cell and embryonic-like stem cell regeneration; subjects in need of WBC regeneration and a balanced lymphoid/myeloid ratio; subjects in need of reversal of immunosuppression, immunodeficiency and immunodepression; subjects in need of neurogenesis and improvement of cognitive performance both related to short-term memory, long-term memory and motor coordination in both young and old mammals; subjects in need of reversal of cognitive decline; subjects having cancer; subjects having an inflammatory disease (e.g., skin dermatitis); subjects having loss of bone density (e.g., osteoporosis); and subjects having liver damage. Examples of such symptoms of Alzheimer's Disease include, but are not limited to, impairment of learning and memory, speech difficulties, agnosia, apraxia, paraphasias, short term memory loss, and the like. Examples of such symptoms of immunosuppression, immunodeficiency and immunodepression include, but are not limited to, susceptibility to infections and susceptibility to cancer. Examples of such symptoms of inflammatory disease include, but are not limited to, inflammation, swelling, redness, pain, calor, and loss of function. Examples of such symptoms of liver damage include, but are not limited to, elevation of ALT, elevation of ALP, bilirubin, itching, jaundice, neoplasm, hepatocellular necrosis, zonal necrosis, and the like.

In a variation of the present embodiment, the step of inhibiting GHR, IGF-I, IGF-IR or PKA includes administering a small drug, antagonist, inhibitory RNA or DNA or antibody to the subject. In a refinement, the step of inhibiting GHR, IGF-I, IGF-IR and/or PKA includes administering a GH/IGF-1 Axis inhibitory composition to the subject. Examples of suitable GH/IGF-1 Axis inhibitory compositions include growth hormone receptor antagonists, an IGF-I receptor antagonists, GH-releasing hormone (GHRH) receptor antagonists, and combinations thereof.

In another embodiment, a method of alleviating a symptom in an immuno-compromised subject is provided. The method includes a step of identifying a subject that is immuno-compromised or a subject that desires an improvement in immune status. A reduction in protein kinase A (PKA) activity and/or IGF-I levels is induced in the subject. Optionally, progress of the subject is monitored by measuring the PKA activity and/or IGF level to verify that at target level of each is achieved. In one refinement, the reduction in protein kinase A (PKA) activity and/or IGF-I levels are reduced by administering a low calorie diet protocol as set forth below. A particularly useful diet protocol is provided by WIPO Pub. No. WO2011/050302, the entire disclosure of which is hereby incorporated by reference. In another refinement, the reduction in protein kinase A (PKA) activity and/or IGF-I levels are reduced by administering a low calorie diet protocol as set forth below.

In another embodiment, a method of transferring hematopoietic stem/progenitor cells to a subject is provided. The method includes a step of identifying an immuno-compromised subject. A reduction in protein kinase A activity and/or IGF-I level is induced in a donor as set forth above. Optionally, regenerative hematopoietic stem/regenerator cells are isolated from the donor and then grafted into the immuno-compromised subject.

In still another embodiment, a method of promoting growth of regenerative cells is provided. The method includes a step of administering a dietary protocol to a subject for a first time period and a second time period. During the first time period, a reduced caloric diet is provided to the subject with at least 50 percent calories derived from fat. During the second time period, a second reduced caloric diet of at most 900 kcal/day is provided to the subject. A particularly useful diet protocol is provided by WIPO Pub. No. WO2011/050302 as set forth above. Optionally, the regenerative cells are isolated from the subject and transferred to a recipient.

In still another embodiment, a method of promoting tissue regeneration in a subject is provided. The method may include the steps of isolating a population of regenerative cells from a donor, the donor having a target PKA level or activity in the tissue in which regeneration is desired. The donor is pretreated to lower PKA activity to reach the target PKA activity. In a refinement, the population of regenerative cells is delivered into a part of the subject where tissue regeneration is desirable. In another refinement, the subject and the donor are the same individual. In these instances, the population of regenerative cells can be isolated from a first body part of the subject and later deposited to a second body part of the subject different from the first body part. Without wanting to be limited to any particular theory, it is believed that resident regeneration with the regenerative cells isolated from and deposited to the same individual provides relief to certain issues such as donor-recipient matching issues mentioned herein elsewhere. In another refinement, the donor and the subject are different individuals. The population of regenerative cells that are isolated include at least one of a stem cell and a progenitor cell. Examples of regenerative cells are obtained from bone marrow, brain, liver, and the like. To obtain the target PKA activity, the donor may have been pretreated with a pharmaceutical composition to reduce PKA activity to be within the pre-determined value range. Alternatively, the donor may have been pretreated with a dietary protocol with components provided from a diet package to reduce PKA activity to be within a pre-determined value range as adapted from WIPO Pub. No. WO2011/050302. In the instances where the diet package is used, the diet package includes components for a first diet and a second diet. The first diet is administered to the donor at a first time period and the second diet for a second time period. Characteristically, the first diet is different in composition than the second diet. In a refinement, the diet package may include components for a third diet administered to the donor for a third time period. Typically, a body weight of the donor is measured prior to the second diet. The second diet may not be administered until the body weight of the donor is within a pre-determined weight range. Typically, the body weight of the donor is measured prior to administration of the third diet. The third diet may not be administered until the body weight of the donor is within a pre-determined weight range. The pre-determined weight range may be 70 to 99 percent of a body weight of the donor/subject prior to the first diet. The first time period may be of between 20 to 120 hours, 20 to 100 hours, 20 to 80 hours, 20 to 70 hours, 20 to 60 hours, 20 to 50 hours, 20 to 40 hours, or 20 to 30 hours. In certain instances, the first time period is 20 to 28 hours. The second time period may be of between 20 to 120 hours, 30 to 110 hours, 40 to 100 hours, 50 to 90 hours, or 60 to 80 hours. In certain instances, the second time period is 68 to 76 hours. The time difference between the start of the first diet and the start of the second diet is typically from 1 to 4 weeks. The first diet may be administered to provide the donor/subject with at most 50% of the subject's normal caloric intake wherein at least 50% of the kilocalories are derived from fat. The first diet may be administered to the donor/subject with from 700 to 1200 kcal/day. The second diet may be administered to provide the donor/subject with a calorie input of at most 500 kcal/day, 400 kcal/day, 300 kcal/day, or 200 kcal/day. The third diet may be administered to provide the donor/subject with greater than 50% of the donor's normal caloric intake. The third diet may be administered to provide the donor/subject with one or more essential amino acids. In a refinement, the third time period may be greater than 120 hours.

As set forth above, embodiments of the invention seek to decrease PKA activity. A decrease in PKA activity and/or a decrease in IGF-I level are achieved by administering a diet protocol of complete food deprivation (i.e. fasting or starvation) or the FMD diet set forth above. Intensive but brief form of calorie restriction, can effectively (48 hrs in mice and 120 hrs in human) reach the essential physiological conditions (e.g. reduction of blood glucose and circulating IGF-I level and reduction of IGF-I signaling) which may be important for promoting the regenerative effects and an increase in stems and/or progenitor cells. The fasting condition induced several stem cell populations with documented therapeutic applications, including the multipotent adult tissue-specific stem/progenitor cells and the rare pluripotent fetal/embryonic like stem cells. The fasting conditions reverse the decline of stem cell number and correct occurred regenerative disorder with no special requirements for initial conditions (e.g., age) and without compromising the long-term regenerative capacity. This high efficiency, broad effects on classes of stem cells, low initial requirements and long-term safety/benefits allow this invention to be practically incorporated with various types of therapy, including chemotherapy and radiotherapy. With no need of invasive approach, it can benefit the conventional regenerative approach in the way that directly stimulates the resident stem cells and/or may indirectly change the microenvironments for promoting the regeneration of the transplanted stem cells in the recipients.

In another variation, a substitution diet is provided to a subject in order to decrease PKA activity and or IGF-I levels. The present variation is particularly useful in that a 120-hr fasting may be difficult for human subjects to achieve due to low compliance and the side-effects of malnutrition. The substitution diet of the present variation maximizes micronutrients without interfering with the beneficial effect of fasting condition in promoting regeneration. The fasting conditions promoting stem cell-based regeneration have been achieved by in vivo fasting/fasting cycles and partially by ii) in vivo substitution diets and ex vivo inhibition of IGF-I or PKA signaling. For human subjects, the substitution diets set forth below mimic the condition achieved by human subjects fasting for 72 to 120 hours, while minimizing malnutrition. Moreover, the diet consists of ingredients which are Generally Regarded As Safe (GRAS). A particularly useful diet protocol is provided by WIPO Pub. No. WO2011/050302 as set forth above. It should be appreciated that substitution diets for subjects other than humans are analogous to those described herein for humans. Such diets are adjusted by taking into consideration the weight and normal food intake of the non-human subjects.

In refinement of the embodiments set forth above, a 5-day supply of diet includes: soups/broths, soft drinks, nut bars and supplements. The diet is administered as follows: 1) on the first day a 1000-1200 kcal diet with high micronutrient nourishment is provided; 2) for the next 4 days a daily diet of 650-800 kcal plus a drink containing a glucose substitution carbon source providing between 60-120 kcal are provided. The substitution carbon source does not interfere with the effect of fasting on stem cell activation.

In another refinement of the embodiments set forth above, a 6-day low-protein diet protocol includes: soups/broths, soft drinks, nut bars, and supplements. The diet is administered as follows: 1) on the first day a 1000-1200 kcal diet plus with high micronutrient nourishment is provided; 2) for the next 3 days a daily diet of less than 200 kcal plus a drink containing a glucose substitution carbon source providing between 60 and 120 kcal. This substitution carbon source does not interfere with the effect of fasting on stem cell activation; 3) on the 5th day the subject consumes a normal diet; and 4) on day 6 an additional replenishment foods consisting of a high fat source of 300 kcal and a micronutrient nourishment mix on day 6 replenishment foods consisting of a high fat source of 300 kcal and a micronutrient nourishment mix are provided in addition to normal diet.

In still another refinement, a diet protocol includes: 6-day supply of low-protein diet includes: soups/broths, soft drinks, nut bars, and supplements. 1) on the first day a 1000-1200 kcal diet with high micronutrient nourishment is provided; 2) for the next 3 days a daily diet of 600 to 800 kcal which contains less than 10 grams of protein and less than 200 kcal from sugars; 3) on the 5th day the subject receives a normal diet; and 4) on day 6 an additional replenishment foods consisting of a high fat source of 300 kcal and a micronutrient nourishment mix on day 6 replenishment foods consisting of a high fat source of 300 kcal and a micronutrient nourishment mix are provided in addition to normal diet.

The present invention, in one or more embodiments, provides nutritional formulations and methods for tissue and organ regeneration. Specific embodiments of methods and compositions that achieve this goal are set forth below. Although the operation of the present invention is not limited to any particular mechanism, the protection observed in various embodiments of the present invention is due in part to modulation of the PKA pathway. The foundation for the protective effect of fasting appears to be based on the ability to reallocate energy to protection/maintenance from reproduction/growth when nutrients are scarce or absent. It should be pointed out, long-term dietary restriction causes a much more modest reduction in IGF-I and glucose compared to fasting. Moreover, unlike fasting, long-term dietary restriction is not feasible for the great majority of the population since it causes chronic weight loss and is very difficult to maintain. Instead, an average of about 62 hours of fasting prior to and 24 hours post-treatment can be well tolerated by subjects receiving treatments.

The embodiments and variations of the present invention achieve a reduction in PKA activity and/or IGF-I levels in a subject by administration of a dietary protocol. As set forth above, a particularly useful diet protocol and dietary packages are provided by WIPO Pub. No. WO2011/050302 and the dietary protocols herein. In particular, subjects are provided with a first diet for a first time period, a second diet for a second time period, and an optional third diet for a third time period. The first diet provides the subject with at most 50% of the subject's normal caloric intake with at least 50% of the kilocalories being derived from fat, preferably monounsaturated fats. The subject's normal caloric intake is the number of kcal that the subject consumes to maintain his/her weight. The subject's normal caloric intake may be estimated by interviewing the subject or by consideration of a subject's weight. As a rough guide, subject's normal caloric intake is on average 2600 kcal/day for men and 1850 kcal/day for women. In certain instances, the first diet provides the subject with from 700 to 1200 kcal/day. In a particularly useful refinement, the first diet provides the male subject of average weight with about 1100 kcal/day and the female subject of average weight with 900 kcal/day. Typically, the first predetermined period of time is from about 1 to 5 days. In certain instances, the first predetermined period of time is 1 day. In order to put the level of fat in the first diet in perspective, the U.S. Food and Drug Administration recommends the following nutritional breakdown for a typical 2000 kilocalorie a day diet: 65 gram fat (about 585 kilocalories), 50 grams protein (about 200 kilocalories), 300 grams total carbohydrates (about 1200 kilocalories). Therefore, in one version of the first diet, a majority of the calories from carbohydrates and proteins are eliminated.

Although the first diet encompasses virtually any source of fat, sources high in unsaturated fat, including monounsaturated and polyunsaturated fat sources, are particularly useful (e.g., omega-3/6 essential fatty acids). Suitable examples of monounsaturated food sources include, but are not limited to, peanut butter, olives, nuts (e.g., almonds, pecans, pistachios, cashews), avocado, seeds (e.g., sesame), oils (e.g., olive, sesame, peanut, canola), etc. Suitable examples of polyunsaturated food sources include, but are not limited to, walnuts, seeds (e.g., pumpkin, sunflower), flaxseed, fish (e.g., salmon, tuna, mackerel), oils (e.g., safflower, soybean, corn). The first diet also includes a component selected from the group consisting of vegetable extracts, minerals, omega-3/6 essential fatty acids, and combinations thereof. In one refinement, such a vegetable extract provides the equivalent of 5 recommended daily servings of vegetables. Suitable sources for the vegetable extract include, but are not limited to, bokchoy, kale, lettuce, asparagus, carrot, butternut squash, alfalfa, green peas, tomato, cabbage, cauliflower, beets. Suitable sources for the omega-3/6 essential fatty acids include fish such as salmon, tuna, mackerel, bluefish, swordfish, and the like.

The subject is then provided the second diet for a second time period. The second diet provides the subject with at most 900 kcal/day. In certain instances, the second diet provides the subject with at most 200 kcal/day. Typically, the second predetermined period of time is from about 2 to 7 days. In certain particular instances, the second predetermined period of time is 3 days. In still another refinement, the second diet includes a component selected from the group consisting of vegetable extracts, minerals, omega-3/6 essential fatty acids, and combinations thereof. In one refinement, such a vegetable extract provides the equivalent of 5 recommended daily servings of vegetable. Suitable sources for the vegetable extract include, but are not limited to, bokchoy, kale, lettuce, asparagus, carrot, butternut squash, alfalfa, green peas, tomato, cabbage, cauliflower, beets. Suitable sources for the omega-3/6 essential fatty acids include fish oils from salmon, tuna, mackerel, bluefish, swordfish, and the like.

The effectiveness of the dietary protocols herein is monitored by measurement of a number of subject parameters. For example, it is desirable that the subject's serum concentration of IGF-I be reduced by 25-90% by the end of the second diet period. It is also desirable that the blood glucose concentration in the subject be reduced by 25-75% by the end of the second diet period. In a refinement, the PKA activity in the tissue or cells of interest to ensure a reduction is PKA activity of at least 15 percent. In other refinements, the PKA activity in the tissue or cells of interest to ensure a reduction is PKA activity of at least 25 percent, 30 percent, or 50 percent. PKA activity may be determined by any number of methods known to those skilled in the art. The ProFluor® PKA Assay commercially available from Promega is one assay that this useful for this purpose.

In a variation of the present embodiment, the subject is provided with a third diet for a third predetermined period of time. The third diet is to supplement the normal diet of the subject. Characteristically, the replenishing composition includes essential amino acids, minerals, and essential fats. Advantageously, the third diet will allow the subject to regain the normal weight and maximize strength. Typically, the third predetermined period of time is at least 5 days. The replenishing composition will also optionally include a number of additional components. For example, the replenishing composition may include a vegetable extract. In one refinement, such a vegetable extract provides the equivalent of 5 recommended daily servings of vegetable. Suitable sources for the vegetable extract include, but are not limited to, bokchoy, kale, lettuce, asparagus, carrot, butternut squash, alfalfa, green peas, tomato, cabbage, cauliflower, beets. The replenishing composition may also include omega-3/6 essential fatty acids, and non-essential amino acids. Examples of suitable non-essential amino acids include, but are not limited to, histidine, serine, taurine, tyrosine, cysteine, glutamine, and combinations thereof. The replenishing composition may also include a multi-mineral tablet containing iron, zinc, copper, magnesium, and calcium and may also contain a vitamin B complex including vitamin B12.

As set forth above, the third diet together with the subject's normal diet will allow the subject to regain the normal weight and maximize strength. Typically, the third predetermined period of time is at least 5 days and may continue indefinitely. In certain instances, the third predetermined period of time is from about 4 days to about 14 days. A week is estimated to be nearly optimal for this purpose. The replenishing composition will also optionally include a number of additional components. For example, the replenishing composition may include a vegetable extract. In one refinement, such a vegetable extract provides the equivalent of 5 recommended daily servings of vegetable. Suitable sources for the vegetable extract include, but are not limited to, bokchoy, kale, lettuce, asparagus, carrot, butternut squash, alfalfa, green peas, tomato, cabbage, cauliflower, beets. The replenishing composition may also include omega-3/6 essential fatty acids, and non-essential amino acids. Examples of suitable non-essential amino acids include, but are not limited to, histidine, serine, taurine, tyrosine, cysteine, glutamine, and combinations thereof. Additional details of the third diet are the same as those set forth above.

In another embodiment, a method of alleviating a symptom of Alzheimer's Disease is provided. The method includes a step of administering an amino acid specific diet having certain amino acids for a first time period. Although the first time period may be for any desired time period, in a refinement, the first time period is from about 5 days to 14 day with 7 days being typical. In a variation, the amino acid specific diet substantially excludes the following amino acids isoleucine, leucine, lysine, methionine, phenylalanine, threonine, tryptophan, valine, and arginine. In this context, "substantially excludes" means that the total of the excluded amino acids is less than, increasing order of preference, 5 weight percent, 3 weight percent, 1 weight percent, and 0.5 weight percent of the total weight of the subject's diet. Instead, the amino acid specific diet provides one or more of the following amino acids as a source of nitrogen: alanine, aspartic acid, cysteine, glutamic acid, glycine, histidine, proline, serine, and tyrosine. Tables 2 to 4 provide characteristics of an amino acid specific diet for a mouse which is also a protein restricted as set forth below. A typical mouse diet provides about 19 kcal per day. For other mammals such as humans, the protein restricted (PR) diet is scaled to provide the requisite calories. For example, a typical caloric intake for adults in the United States is about 2200 calories per day. Table 5 provides the kilocalories per day from each source for human subjects while Table 6 provides the grams per day from each source for humans.

TABLE 2

| | Normal Diet | PR diet |
|---|---|---|
| | Ingredients (g/kg) | |
| Corn Starch | 397.49 | 397.49 |
| Maltodextrin | 132 | 149.88 |
| Sucrose | 100 | 100 |
| Soybean Oil | 70 | 72 |
| Cellulose | 50 | 50 |
| Mineral | 35 | 35 |
| Vitamin | 10 | 10 |
| Choline Bitartarate | 2.5 | 2.5 |
| Tert-butylhydroquinone | 0.01 | .01 |
| | Macronutrients (g/kg) | |
| Carbohydrate | 601 | 617 |
| Nitrogen Source | 177 | 183 |
| Fat | 72 | 72 |
| | Caloric density (kcal/g) | |
| | 3.7600 | 3.7673 |

TABLE 3

Kilocalories in 1 kg of mouse from each food source.

| | NORMAL DIET | PR |
|---|---|---|
| Carbohydrate | 2404 | 2468 |
| Nitrogen Source | 708 | 732 |
| Fat | 648 | 648 |
| calculated | 3760 | 3848 |

TABLE 4

Percent calories from each source (mouse).

| | NORMAL DIET | PR |
|---|---|---|
| Carbohydrate | 63.94 | 64.14 |
| Nitrogen Source | 18.83 | 19.02 |
| Fat | 17.23 | 16.84 |

TABLE 5

Calories per day from each source (Humans).

| | NORMAL DIET | PR |
|---|---|---|
| Carbohydrate | 1406.60 | 1411.02 |
| Nitrogen Source | 414.26 | 418.50 |
| Fat | 379.15 | 370.48 |
| Total (kcal) | 2200.00 | 2200.00 |

TABLE 6

Grams per day from each source (Humans).

| | NORMAL DIET | PR |
|---|---|---|
| Carbohydrate | 351.65 | 352.75 |
| Nitrogen Source | 103.56 | 104.63 |
| Fat | 42.13 | 41.16 |
| Total (g) | 497.34 | 498.54 |

In a refinement, a kilogram of the amino acid specific diet for a mouse includes from about 2 g to 20 g alanine, 10 g to 30 g aspartic acid, 2 g to 20 g cysteine, 40 g to 80 g glutamic acid, 2 g to 20 g glycine, 2 g to 20 g histidine, 15 g to 50 g proline, 5 g to 30 g serine, and 5 to 30 g tyrosine. For human subjects, these ranges are multiplied by a factor (i.e., about 0.572) to provide the composition of the dietary formulation per day for human subjects. For example, the daily amounts of the specified amino acids for humans (2200 Calorie/day diet) in the amino acid specific diet are about 2 to 12 g alanine, 5 g to 30 g aspartic acid, 1 g to 7 g cysteine, 18 g to 73 g glutamic acid, 2 g to 9 g glycine, 2 g to 10 g histidine, 9 g to 37 g proline, 5 g to 21 g serine, and 5 to 21 g tyrosine. In another refinement, the amino acid specific diet includes from about 160 to about 240 g of the specified amino acids per kilogram of the diet. Therefore, for humans the amino acid specific diet provides from about 80 to 160 g of the specified amino acids per day using a factor (0.572) to convert the per kilogram of diet value to a value representative of a human diet of about 2200 Calories/day. In another variation, the amino acid specific diet includes at least 6 amino acids selected from the group consisting of alanine, aspartic acid, cysteine, glutamic acid, glycine, histidine, proline, serine, and tyrosine in the amounts set forth above. In still another variation, the amino acid specific diet provides the amounts of amino acids in grams per Kg of human body weight per day set forth in Table 7. In particular, the amino acid specific diet provided the following grams per Kg of human body weight per day 0.06 g alanine, 0.14 g aspartic acid, 0.04 g cysteine, 0.45 g glutamic acid, 0.05 g glycine, 0.06 g histidine, 0.23 g proline, 0.13 serine, and 0.13 g tyrosine. In another refinement, each of these amino acids is within a range of plus or minus 30 percent of the specified value.

TABLE 7

Human levels. Grams of each amino acid selected for the dementia protecting diet per Kg of human body weight per day.
Formulation grams/kg Body Weight

| AA | NORMAL DIET | PR | Factor |
|---|---|---|---|
| Ala | 0.07 | 0.06 | 0.81 |
| Asp | 0.13 | 0.14 | 1.09 |
| Cys | 0.02 | 0.04 | 2.05 |

TABLE 7-continued

Human levels. Grams of each amino acid selected for the dementia protecting diet per Kg of human body weight per day.
Formulation grams/kg Body Weight

| AA | NORMAL DIET | PR | Factor |
|---|---|---|---|
| Glu | 0.20 | 0.45 | 2.23 |
| Gly | 0.06 | 0.05 | 0.94 |
| His | 0.04 | 0.06 | 1.68 |
| Pro | 0.10 | 0.23 | 2.25 |
| Ser | 0.09 | 0.13 | 1.35 |
| Tyr | 0.06 | 0.13 | 2.19 |
| Total | 0.78 | 1.30 | |

In another embodiment, another method for alleviating a symptom of Alzheimer's Disease is provided. The method includes a step of administering a protein restricted (PR) diet to a subject for a first time period. In a variation, the PR diet includes a dietary supplement of specific amino acids. In a refinement, the first time period is from about 5 days to 14 day with 7 days being typical. Moreover, the low protein diet provides the subject with from 70 to 100 percent of the subject's normal caloric intake. The PR diet includes substantially only amino acids as a source of nitrogen. For example, the protein restricted diet derives less than 10 percent of its calories from proteins. In another refinement, the protein restricted diet derives less than 5 percent of its calories from proteins. In another refinement, the protein restricted diet derives zero percent of its calories from proteins. In particular, the protein restricted diet substantially excludes the following amino acids isoleucine, leucine, lysine, methionine, phenylalanine, tryptophan, valine, and arginine. In this context, "substantially excludes" means that the total of the excluded amino acids is less than, increasing order of preference, 5 weight percent, 3 weight percent, 1 weight percent, and 0.5 weight percent. Instead, the protein restricted diet provides one or more of the following amino acids as a source of nitrogen: alanine, aspartic acid, cysteine, glutamic acid, glycine, histidine, proline, serine, and tyrosine. Tables 2 to 4 provide characteristics a protein restricted diet including the dietary supplement for the mouse studies that are set forth below. A typical mouse diet provides about 19 kcal per day. For other mammals such as humans, the PR diet is scaled to provide the requisite calories. For example, a typical caloric intake for adults in the United States is about 2200 kcalories per day. Table 5 provides the kilocalories per day from each source for human subjects while Table 6 provides the grams per day from each source for humans.

In a refinement, the amino acids in a kilogram of the PR diet for a mouse are provided in Table 8. In a refinement, a kilogram of the PR diet for a mouse includes from about 2 g to 20 g alanine, 10 g to 30 g aspartic acid, 2 g to 20 g cysteine, 40 g to 80 g glutamic acid, 2 g to 20 g glycine, 2 g to 20 g histidine, 15 g to 50 g proline, 5 g to 30 g serine, and 5 to 30 g tyrosine. For human subjects, these ranges are multiplied by a factor (i.e., about 0.572) to provide the daily requirements for these amino acids per day for human subjects. For example, the daily amounts of the specified amino acids for humans (2200 Calorie/day diet) in the PR diet are about 2 to 12 g alanine, 5 g to 30 g aspartic acid, 1 g to 7 g cysteine, 18 g to 73 g glutamic acid, 2 g to 9 g glycine, 2 g to 10 g histidine, 9 g to 37 g proline, 5 g to 21 g serine, and 5 to 21 g tyrosine. In another refinement, the protein restricted diet includes from about 160 to about 240 g of the specified amino acids per kilogram of the diet. Therefore, for humans the PR diet provides from about 80 to 160 g of the specified amino acids per day using a factor (0.572) to convert the per kilogram of diet value to a value representative of a human diet of about 2200 Calories/day. In another variation, the protein restricted diet includes at least 6 amino acids selected from the group consisting of alanine, aspartic acid, cysteine, glutamic acid, glycine, histidine, proline, serine, and tyrosine in the amounts set forth above. Table 8 provides an example of the amino acid content in the protein restricted diet for a mouse diet. Table 8 also provides a factor which is the ratio of a specified amino acid in the protein restricted diet to that of the control (normal diet). These ratios are equally applicable to other mammals such as human subjects. In still another variation, the PR diet provides the amounts of amino acids in grams per Kg of human body weight per day set forth in table 8. In particular, the PK diet provided the following grams per Kg of human body weight per day 0.06 g alanine, 0.14 g aspartic acid, 0.04 g cysteine, 0.45 g glutamic acid, 0.05 g glycine, 0.06 g histidine, 0.23 g proline, 0.13 serine, and 0.13 g tyrosine. In another refinement, each of these amino acids is within a range of plus or minus 30 percent of the specified value.

TABLE 8

Mouse data providing the amount of amino acid per kilogram of diet for the normal diet (the control) and for the experimental diet (PR). The factor is the ratio of PR to Control.
g/kg diet

| AA | NORMAL DIET | PR | Factor |
|---|---|---|---|
| Ala | 10.00 | 8.30 | 0.83 |
| Arg | 12.00 | 0.00 | 0.00 |
| Asp | 18.00 | 20.10 | 1.12 |
| Cys | 3.00 | 6.30 | 2.10 |
| Glu | 28.00 | 63.90 | 2.28 |
| Gly | 8.00 | 7.70 | 0.96 |
| His | 5.00 | 8.60 | 1.72 |
| Ile | 8.00 | 0.00 | 0.00 |
| Leu | 17.00 | 0.00 | 0.00 |
| Lys | 10.00 | 0.00 | 0.00 |
| Met | 4.00 | 0.00 | 0.00 |
| Phe | 9.00 | 0.00 | 0.00 |
| Pro | 14.00 | 32.30 | 2.31 |
| Ser | 13.00 | 17.90 | 1.38 |
| Thr | 8.00 | 0.00 | 0.00 |
| Trp | 3.00 | 0.00 | 0.00 |
| Tyr | 8.00 | 17.90 | 2.24 |
| Val | 9.00 | 0.00 | 0.00 |
| Total | 187 | 183 | |

In some variations, the methods set forth above further include a step of administering a normal diet (i.e., a control diet) to a subject for a second time period which follows the first period of time. The normal diet provides the subject with a normal caloric intake without any restrictions regarding protein. Moreover, no amino acid is explicitly excluded from the normal diet. Typically, the second time period is from 5 day to 28 days or more. In a variation, the subject is provided alternating protein restricted diets plus amino acid supplement and normal diets for 1 or more iterations through the protein restricted diet and the normal diet. Table 2 provides an example of the amino acid content in a normal diet. Tables 2 to 4 provide characteristics a normal diet for the mouse studies that are set forth below. For other mammals such as humans, the diet is scaled to provide the requisite calories. For example, atypical caloric intake for adults in the United States is about 2200 calories per day therefore the mouse data is multiplied by a factor (0.585) to provide data relevant to human subjects. Table 5 provides the kilocalories per day from each source for the normal diet for human subjects while Table 6 provides the grams per day for each source for the normal diet for human subjects.

In another embodiment, a dietary supplement to be combined with a subject's diet is provided. In a variation, the subject's diet has low (e.g. less than 5, 3, 1, or 0.5 weight percent) or zero percent proteins. Therefore in this variation, the dietary supplement plus the subject's diet form the PR diet set forth above. In another variation, the subject diet is the subject's normal diet (e.g., 2200 Calories/day for humans) or any diet to which addition of the specified amino acids is desired. The dietary supplement includes sufficient amounts of the specified amino acids to meet the dietary requirements set forth above. In particular, the dietary supplement includes alanine, aspartic acid, cysteine, glutamic acid, glycine, histidine, proline, serine, and tyrosine while substantially excluding isoleucine, leucine, lysine, methionine, phenylalanine, threonine, tryptophan, valine, and arginine. In a refinement, the dietary supplement includes sufficient amounts of the specified amino acids to provide these amino acids in the amounts set forth above. Table 8 provides the ranges of the amino acid ratios to cysteine in the dietary supplement. In a variation, the dietary supplement includes sufficient amount of amino acids for one or more cycles through the first time period. Typically, the dietary supplement includes instructions for carrying out the dietary protocol set forth above.

The following examples illustrate the various embodiments of the present invention. Those skilled in the art will recognize many variations that are within the spirit of the present invention and scope of the claims.

Dietary and/or calorie restriction (CR) promotes the self-renewal of intestinal stem cells and neural regeneration, reduces the decline of HSC number during aging and preserves their long-term regenerative capacity (1-4). However, the effects of either CR or fasting on immunodeficiency and the stem cell-based regeneration of the hematopoietic system were previously unknown. Also, CR is a chronic intervention which cannot be separated from weight loss and which causes moderate effects on IGF-I and glucose levels (5). By contrast, we show that fasting cycles, which allow mice to regain and maintain normal weight, promote major increases in pluripotent CD45⁻ MSC/EPC and multipotent adult HSPCs, accompanied with the regeneration of multiple systems, including brain, liver and blood, even under conditions that cause its severe depletion. These results suggest that cycles of complete food deprivation may serve as the trigger for either the stem cell self-renewal or dedifferentiation/reprogramming in a hierarchical fashion.

Based on the evidence from animal and human studies, lifestyles that incorporate various forms of fasting during adult life promote health while simultaneously reducing the risk of many chronic diseases, particularly for those who are overweight and sedentary. Notably, various fasting approaches remain to be a challenge e.g. due to major interventions into the subject's lifestyle and eating habits, low compliance and the side-effects of malnutrition. As such, low calorie fasting-mimicking diets (FMD) that induce fasting-like effects in subjects present an alternative to fasting. In addition, diets, rather than fasting, allow providing micronutrient nourishment, preferably as much as possible through natural food sources. We here show examples that repeated cycles of a FMD promote health span, adult neurogenesis, cognitive performance and tissue maintenance as well as tissue regeneration in subjects.

FIG. 1 provides Table 9 which illustrates the effects on body composition in rodent and human subjects. In 16.5 months old female BALB/c mice one cycle of FMD significantly reduced the bodyweight by 18% compared to ad lib fed controls. After re-feeding, no significant difference in weight remained, indicating that all mice recovered from the dietary regime after completion of the first cycle. The decrease in weight can be attributed to the relatively low calorie intake during the FMD cycle which was reduced by ~80% when considering all 4 days of the cycle. No difference in calorie intake was observed between diet and control groups, since mice compensated after FMD feeding by a slight over-consumption during re-feeding; thus normalizing the calorie intake. Repeated feeding cycles of the fasting mimicking diet separated the bodyweight of the two groups. While mice in the control group increased their bodyweight for ten feeding cycles, mice in the FMD group maintained a bodyweight that was close to their weight before the onset of the FMD regime for approximately 12 feeding cycles before a slow decrease in weight became apparent. Therefore long-term effects of the FMD regimen on total body fat as well as the subcategorized fat deposits (subcutaneous and visceral) were evaluated by X-ray computed tomography (CT) scans. At 28 months of age and after completion of 23 FMD cycles, total and visceral body fat, which is closely related to pathologies associated with obesity, were reduced in the FMD-fed mice. Only a minor effect on subcutaneous fat deposits was measurable. In human subjects, after one and three cycles of a fasting-mimicking diet, body weight (as % compared to the baseline values prior to the start of the FMD) was significantly reduced and has thus similar effects as seen in the preclinical experiments. The relative percentage of trunk fat for human subjects was evaluated upon the completion of three cycles of FMD by "Dual-energy X-ray absorptiometry" (DEXA) in human subjects.

FIG. 2 provides Table 10 which illustrates the FMD diet achieving a reduction in cancer incidence, delay the onset of cancer-related death and/or affect biomarkers associated with health- and lifespan in subjects. Upon autopsy, neoplasms were the most prominent alteration found in subjects although with reduced incidence rate in FMD fed subjects. Competing risk regression analysis showed a significant reduction (p=0.02) in neoplasia-related deaths for subjects in the FMD cohort. When considering the neoplasia incidence, it also became apparent that subjects in the FMD cohort succumbed to neoplasms later in life. Glucose and IGF-1, both shown to promote tumor development and progression, were significantly reduced during the FMD regimen. IGFBP-1, which binds and reduces the bioavailability of IGF-1, was increased; thereby further reducing IGF-1 signaling. Similarly to the preclinical data, IGF-1 was reduced after the first and third FMD cycle. IGFBP-1 levels were increased.

FIG. 3 provides Table 11 which provides nutritional formulations and methods to reduce inflammation in various tissues and organs. Inflammation plays a diverse role in the development of many age-related diseases such as atherosclerosis, cancer, obesity, diabetes, congestive heart failure, digestive system diseases, and Alzheimer's disease (6). Compared to ad lib fed control animals, subjects maintained on the FMD diet starting at 16.5 months of age had a significantly reduced incidence of inflamed tissues detected at necroscopsy. Inflamed tissues included among others the liver and reproductive tract of female subjects (not shown). One of several C57B1/6 strain (both genders) specific background diseases is the appearance of focal alopecia that often progresses to severe ulcerating dermatitis. Subjects fed with the FMD diet displayed a 50% reduction in dermatitis incidence over their lifespan compared to the ad lib fed control subjects (10.3% vs. 19.6%, respectively).

FIG. 4 provides Table 12 in which subjects fed with the FMD diet showed a delayed loss of aging-related bone mineral density. Bone mineral density (BMD) declines with age and low BMD is one of the most important risk factors for fractures. Bone mineral density [in mg Hydroxyapatite (HA)/cm$^3$] of the femoral bone was analyzed by X-ray computed tomography (CT)-scans in control-fed mice at 12 and 28 months of age, as well as 7 days after the re-feeding of subjects in the FMD cohort in vivo at 28 month of age (FMD-refed). After 12 months of bi-monthly feeding the FMD substitution diet, the levels of hydroxyapatite/cm$^2$ in the femur of FMD-fed subjects were higher (p<0.05) compared to those in subjects fed the standard diet, indicating reduced senile osteoporosis in this group.

FIG. 5 provides Table 13 which provides nutritional formulations and methods for liver regeneration. In comparison to 20-22.5 months old mice from ad lib fed control, subjects fed with the experimental FMD diet starting at 16.5 months of age had significantly reduced liver weight and lose about 35% of the original liver mass at the end of the FMD regimen. Alanine aminotransferase (ALT) level, a clinical diagnostic marker for the evaluation of hepatocellular injury and liver health, was elevated at the end of the FMD regimen but returned to normal levels within 7 days of refeeding. The increase in ALT is consistent with the observation that the FMD diet causes extensive structural alterations and autophagy of hepatocytes (Table 13 B, asterisks). 24 hours after refeeding, the liver weight returns to, and even exceeds (+10%), normal weight thereby indicating the repopulation of loss liver mass by means of newly generated cells. Liver H&E staining of subjects in the control (Table 13 A) and FMD group 24 hours after refeeding demonstrates the infiltration of unorganized cells around the vein (Table 13 B, arrow) indicating liver regeneration and repopulation with hepatocytes immediately after refeeding.

Figure 6:
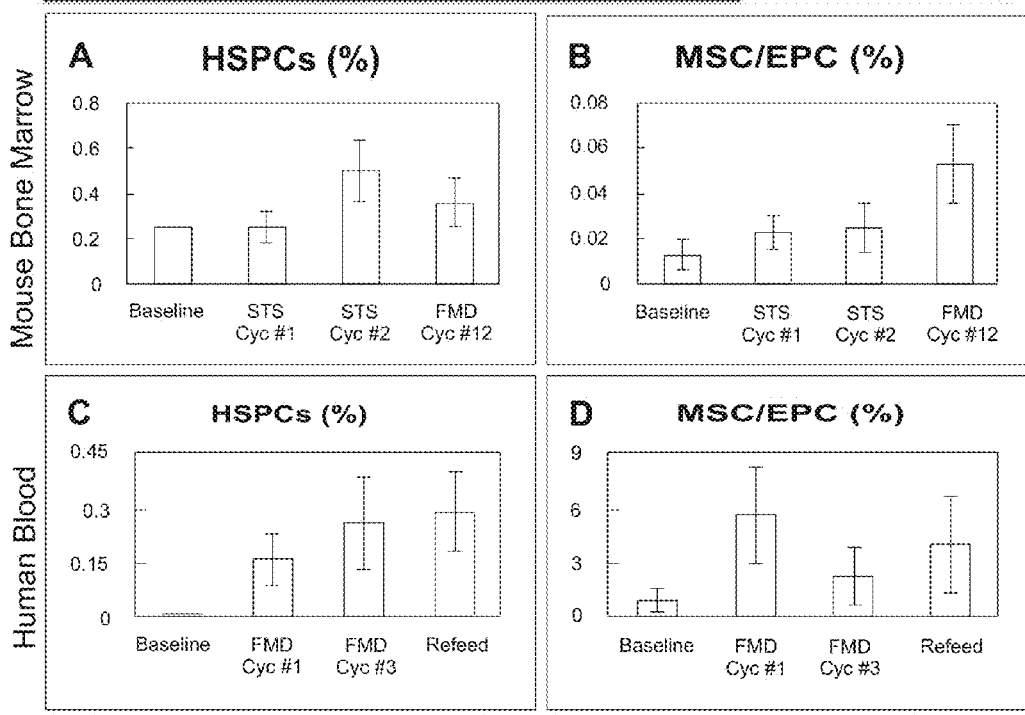
FIG. 6 provides Table 14 and plots showing cycles of short-term starvation (STS) or a fasting mimicking diet stimulate stem/progenitor cells in mice and human subjects. The frequency of hematopoietic stem/progenitor cells (HSPCs, A) and non-hematopoietic mesenchymal and endothelial stem/progenitor cells (MSC/EPC, B) residing in the bone marrow increases after repeated cycles of STS or FMD in mice. HSPCs (Lin-Sca-1+C-kit+) are multipotent precursor cells constituting all lineages of blood cells. MSC/EPC (Lin-Sca-1+CD45−) are multipotent precursor cells that can differentiate into specific connective tissues. Similarly, the frequency of HSPCs (C, Lin-CD184+CD45+) and MSC/EPC (D, Lin-CD184+CD45−) cells circulating in human peripheral blood after cycles of FMD increases. Data in tables were presented as mean±SD and that in figures were presented as mean±SEM.

FIG. 6 provides results for nutritional formulations and methods that increase stem/progenitor cells. In mice, hematopoietic stem/progenitor cells (HSPCs) began to increase in the bone marrow after two cycles of short-term starvation (STS, Table 14 A). The induction of mesenchymal and endothelial stem/progenitor cells (MSC/EPCs) could also be observed in mice after 48 hours of short-term starvation (Table 14 B); 12 cycles of FMD resulted in similar effects (Table 14). In human subjects, HSPCs (Table 14 C) and MSC/EPCs (Table 14 D) began to increase after the completion of one FMD cycle and the effects remained after refeeding.

FIG. 7 provides results for nutritional formulations and methods that promote hematopoietic regeneration. In mice, multiple cycles of cyclophosphamide caused white blood cell (WBC) deficiency and lymphoid/myeloid (L/M) bias (Table 15). Cycles of fasting accelerated the recovery of WBCs and rebuilt the homeostasis of lymphoid- or myeloid-lineages (Table 15). In human subjects receiving immunosuppressive chemotherapy, similar pro-regenerative effects were observed in WBC and L/M after two cycles of fasting (Table 15).

FIG. 8 provides results for nutritional formulation and methods that alleviates age-dependent myeloid-bias. The homeostasis of blood lineages becomes disturbed during aging and biased towards myeloid lineages (Table 16). In both mice and human subjects, cycles of FMD prevent the deviation from a lineage-balance and reverse the degenerative effect in middle-aged subjects (Table 16).

Figure 9:
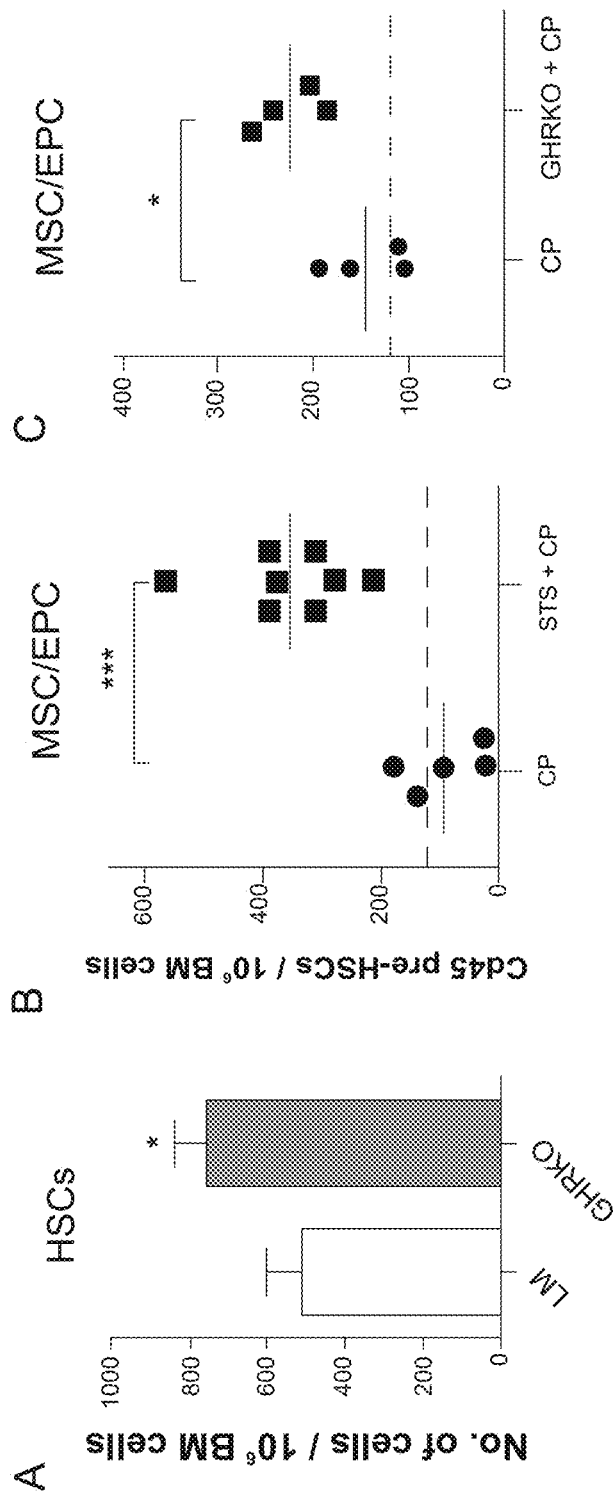
FIG. 9 illustrates increased number of hematopoietic stem cells (HSPCs) and frequency of non-hematopoietic mesenchymal and endothelial stem/progenitor cells (MSC/EPCs) in growth hormone receptor knockout (GHRKO) mice and by short-term starvation. (A) Hematopoietic stem cells (HSCs, Lin-Sca-1+C-kit+) in wild type (littermate, LM) and growth hormone receptor knockout (GHRKO) mice with GHR/IGF-1 deficiency. (B) 6 cycles of cyclophosphamide (CP) chemotherapy treatment had no effect on the MSC/EPC (Lin-Sca-1+CD45−) frequency in mice (dashed line indicates level in untreated animals). When combined with STS, the MSC/EPC (Lin-Sca-1+CD45−) frequency was significantly elevated. (C) Similarly, GHRKO mice had an elevated MSC/EPC frequency when treated with CP compared to their wild type littermates. This suggests that GHR/IGF-1 deficiency can mimic STS effects to stimulate bone marrow derived stem/progenitor cells.
Figure 10:
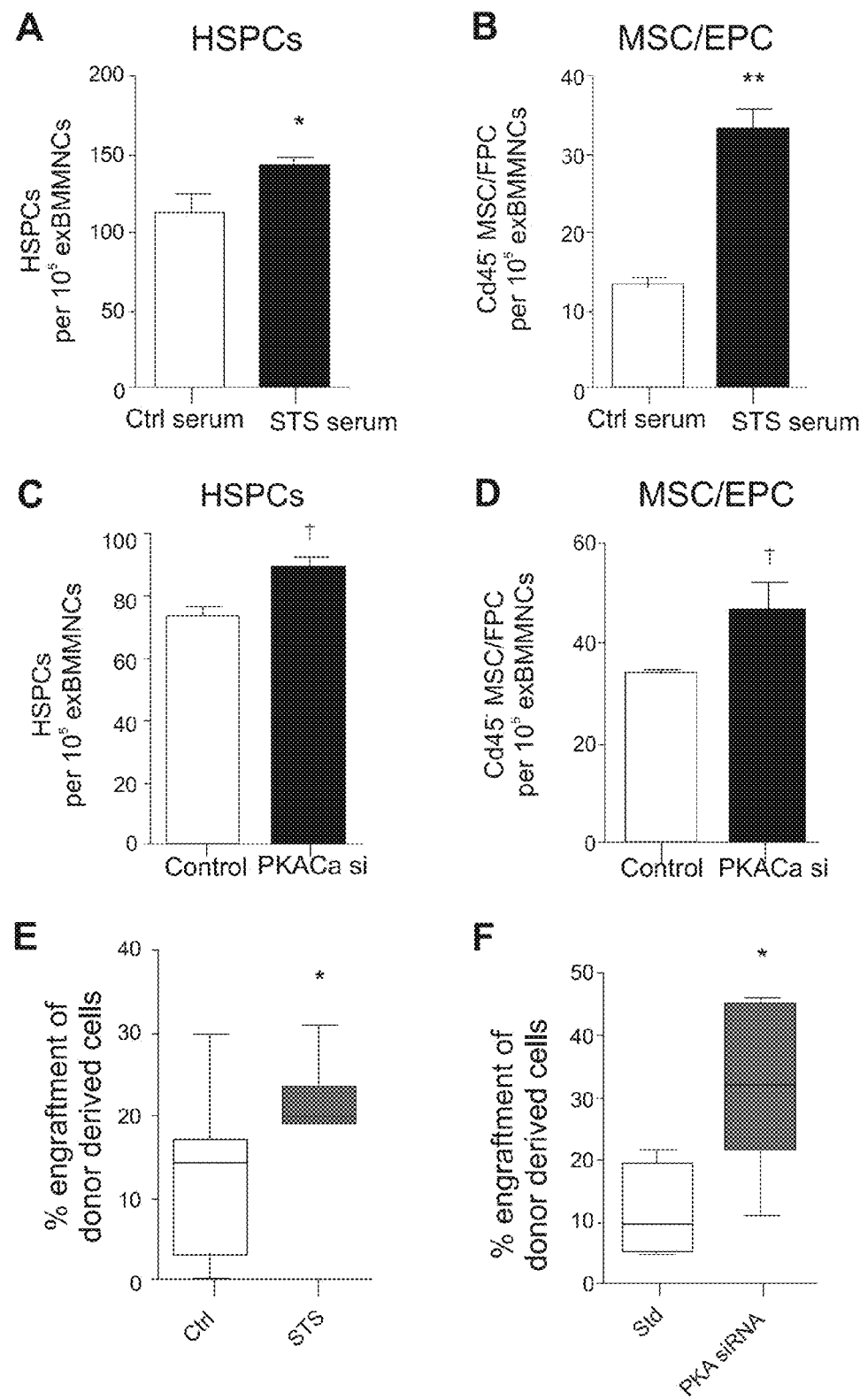
FIG. 10 illustrates the inhibition of PKA signaling mimics short-term starvation to increase bone marrow-derived stem/progenitor cells and stimulate hematopoietic reconstitution. (A) Hematopoietic stem cells (HSPCs. Lin-Sca-1+C-kit+) and (B) MSC/EPC (Lin-Sca-1+CD45−) in the explanted bone marrow cells were incubated in standard culture medium supplemented with 10% serum derived from either control or STS (48 hr) mice for 24 hours. Serum from fasted mice significantly increased the number of HSPCs and MSC/EPCs. (C and D) Treatment with PKACα siRNA resulted in a similar increase and indicates that the reduction in PKA signaling mimics fasting and stimulates bone marrow-derived stem/progenitor cells. (E and F) A competitive repopulation assay was performed to test the blood reconstitution capacity of HSPCs in vivo. Bone marrow cells collected from mice fed ad libitum (E, Ctrl) and 48 hr-fasted mice (E, STS) were transplanted into immuno-compromised recipient mice. The blood cells regenerated by donor HSPCs in ratio to that of the competitor cells was measured as the % of engraftment of donor derived cells. Similar to that of bone marrow cells from fasted mice (E), reconstitution capacity of bone marrow cells treated with PKA siRNA was significantly improved (F).
Figure 11:
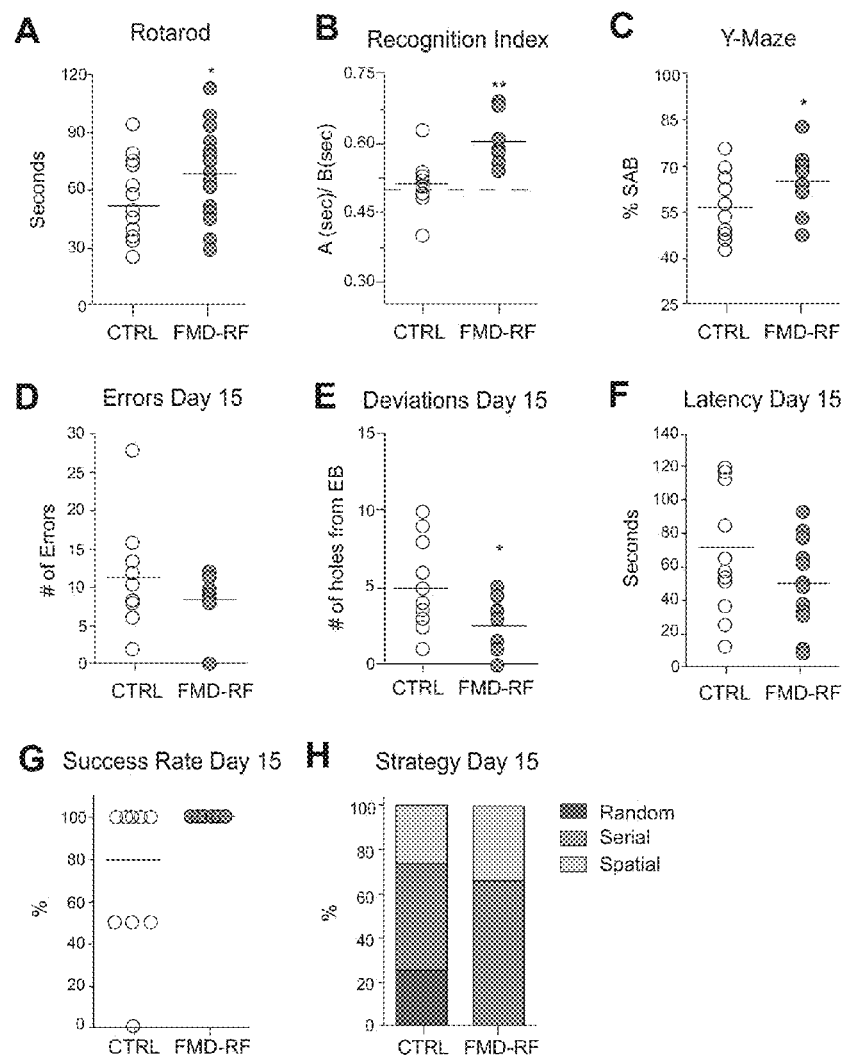
FIG. 11 provides Table 17 and plots showing effects of a fasting mimicking diet on the brain and cognitive functions. The proliferative index and adult neurogenesis in mice was evaluated based on bromodeoxyuridine (BrdU) incorporation that were started 4 days prior to the 12th cycle of the FMD diet and compared to age-matched ad lib fed controls (23 months). BrdU-positive cells are elevated in the sub-granular zone. DCX+ staining was performed to measure immature neurons in the dentate gyrus. In the FMD group, 17.6% of the BrdU retaining cells were also positive for DCX compared to 3.1T in controls, indicating that the FMD group had an increase in neural precursor cells that were committed to the neuronal lineage. All data were presented as mean±SEM. *p<0.05 compared to ad lib fed mice. Adult neurogenesis has been implicated in motor coordination skills, short-term recognition and long-term spatial recognition performance in aged mice. To test the motor coordination and motor skill learning, mice from the control and FMD cohort were tested with the accelerating rotarod (A). The best score (in seconds) out of 6 trial sessions was significantly improved for mice in the FMD cohort compared to ad lib fed mice at 23 month of age. Spatial recognition and short-term memory were evaluated with the novel object recognition test (B) and Y-maze (C). The novel object recognition behavior test evaluates the context-dependent memory and is calculated as a recognition index defined as the ratio of time (in seconds) spent between a familiar object and a novel object. During the adjusting phase, two identical objects are placed inside a rectangular cage and the time spent exploring both objects was recorded. After this adjustment period, one object was replaced with a novel object and the time spent exploring both objects was recorded (B). Mice in the FMD cohort performed significantly better in this test, indicating better object-related short-term memory. (C) Working memory function was investigated based on the spontaneous alternation behavior (SAB) in an Y-maze. FMD fed mice performed in this test significantly better than the ad lib fed mice. (D-H) Spatial learning was tested with the Barnes Maze at 23 month of age for animals in the control and FMD groups. The number of errors (D, defined as nose pokes and head deflections over any false target hole), deviations from the escape box (E, how many holes away from the escape box was the first error), latency (F, the time it took the mouse to enter the escape box), and success rate (G, 100%, finding an escape box within 2 minutes or 0%, not finding the escape box within 2 minutes) were recorded. The memory retention was assessed by testing each mouse on day 15 and measurements were averaged from two tests to obtain the value for each mouse. (H) Search strategies were classified as random (localized hole searches separated by crossings through the maze center), serial (systematic hole searches in a clockwise or counter-clockwise direction) or spatial (navigating directly to the escape box with both error and deviation scores of no more than 3). Mice in the FMD-fed cohort displayed superior search strategies and better retention of their escape box at day 15, thus demonstrating improved cognitive abilities in the motor learning and hippocampus-dependent short- and long-term memory. The bar in A-H represents the mean. *p<0.05; **p<0.01, compared to ad lib fed mice.

FIGS. 9 and 10 illustrate that methods that mimic fasting to stimulate stem/progenitor cells by dampening GHR/IGF-1 or PKA signaling. Similar to that caused by fasting, the targeted disruption of the growth hormone receptor gene (GHRKO) causes a significant reduction in circulating IGF-1 and the induction of HSPCs and MSC/EPC in mice (FIG. 9). PKA siRNA treatment that inhibits PKA activity also caused a similar induction in stem/progenitor cells ex vivo. The regenerative capacity of the increase in regenerative cells was evident in immuno-compromised recipient mice in vivo (FIG. 10).

FIGS. 11-14 provide experiment results for nutritional formulations and methods that induce adult neurogenesis and improve cognitive performance (Table 17). The proliferative index and adult neurogenesis in subjects was evaluated based on bromodeoxyuridine (BrdU) incorporation that was started 4 days prior to the 12th cycle of the FMD diet and compared to age-matched ad lib fed control subjects (23 months). BrdU-positive cells are elevated in the sub-granular zone. DCX+ staining was performed to measure immature neurons in the dentate gyrus. In the FMD cohort, 17.6% of the BrdU retaining cells were also positive for DCX compared to 3.1% in controls, indicating that the subjects in the FMD group had an increase in neural precursor cells that were committed to the neuronal lineage. Adult neurogenesis has been implicated in motor coordination skills, short-term recognition and long-term spatial recognition performance in aged mice. Subjects maintained on the FMD were tested for long-term spatial learning and memory (Barnes maze), short-term memory (novel object recognition) and working memory (Y-maze), as well as coordination and balance (rotarod) and compared to subjects fed with normal rodent chow. All behavior tests were done between 10 and 12 diet cycles (5-6 months on the FMD diet) at the age of 23-24 months. To prevent starvation-induced hyper-activity or unusual movement, FMD subjects were exposed to the behavior tests not earlier than 3 days after re-feeding, which is the approximate time that it took subjects to regain normal bodyweight. To test the motor coordination and motor skill learning, subjects from the control and FMD cohort were tested with the accelerating rotarod (Table 17A). The best score (in seconds) out of 6 trial sessions was significantly improved for subjects in the FMD cohort compared to ad lib fed subjects at 23 month of age. Spatial recognition and short-term memory were evaluated with the novel object recognition test (Table 17 B) and Y-maze (Table 17 C). The novel object recognition behavior test evaluates the context-dependent memory and is calculated as a recognition index defined as the ratio of time (in seconds) spent between a familiar object and a novel object. During the adjusting phase, two identical objects are placed inside a rectangular cage and the time spent exploring both objects was recorded. After this adjustment period, one object was replaced with a novel object and the time spent exploring both objects was recorded (Table 17B). Subjects in the FMD cohort performed significantly better in this test, indicating better object-related short-term memory. Working memory function was investigated based on the spontaneous alternation behavior (SAB) in a Y-maze (Table 17C). FMD fed subjects performed in this test significantly better than the ad lib fed subjects. Spatial learning was tested with the Barnes Maze at 23 month of age for subjects in the control and FMD groups (Table 17D-H). The number of errors (Table 17D, defined as nose pokes and head deflections over any false target hole), deviations from the escape box (Table 17E, how many holes away from the escape box was the first error), latency (Table 17F, the time it took the mouse to enter the escape box), and success rate (Table 17G, 100%, finding an escape box within 2 minutes or 0%, not finding the escape box within 2 minutes) were recorded. The memory retention was assessed by testing each subject on day 15 and measurements were averaged from two tests to obtain the value for each subject. Search strategies were classified as random (localized hole searches separated by crossings through the maze center), serial (systematic hole searches in a clockwise or counter-clockwise direction) or spatial (navigating directly to the escape box with both error and deviation scores of no more than 3) (Table 17H). Subjects in the FMD-fed cohort displayed superior search strategies and better retention of their escape box at day 15, thus demonstrating improved cognitive abilities in the motor learning and hippocampus-dependent short- and long-term memory.

PRC regimen does not cause a chronic low weight state nor an overall decrease in calorie intake. Differently from control animals fed with a normal diet, after seven days of PR diet both 3xTg-AD and WT mice lost between 13 and 17% of the initial body weight, which was fully recovered during the following seven days of re-feeding with the normal diet (FIG. 15B, repeated measures ANOVA followed by Newman-Keuls test: $p<0.001$, control regimens compared with PRC regimens). A similar body weight profile was maintained by mice subjected to PCR regimen during the whole 18 weeks of dietary treatment (FIG. 15C, repeated measures ANOVA followed by Newman-Keuls test: $p<0.001$, control regimens compared with PRC regimens). Also, we found a significant difference between WT and 3xTg-AD groups, with 3xTg-AD rodents gradually and slightly losing weight at week 6-7 (FIG. 15C, repeated measures ANOVA followed by Newman-Keuls test: $p<0.05$, 3xTg-AD control vs. WT control and 3xTg-AD PRC vs. WT PRC). Considering the gradual body weight drop in the 3xTg-AD control group, the age-dependent weight loss of 3xTg-AD PRC mice on the PR diet appears to be mostly dependent on the mutations and not the diet. Taken together, these data indicate that PRC regimen was not associated with a chronic underweight in both WT and 3xTg-AD mice although they suggest that longer periods of normal diet re-feeding may be required to allow weight maintenance after long-term cycles of protein restriction.

Figure 21:
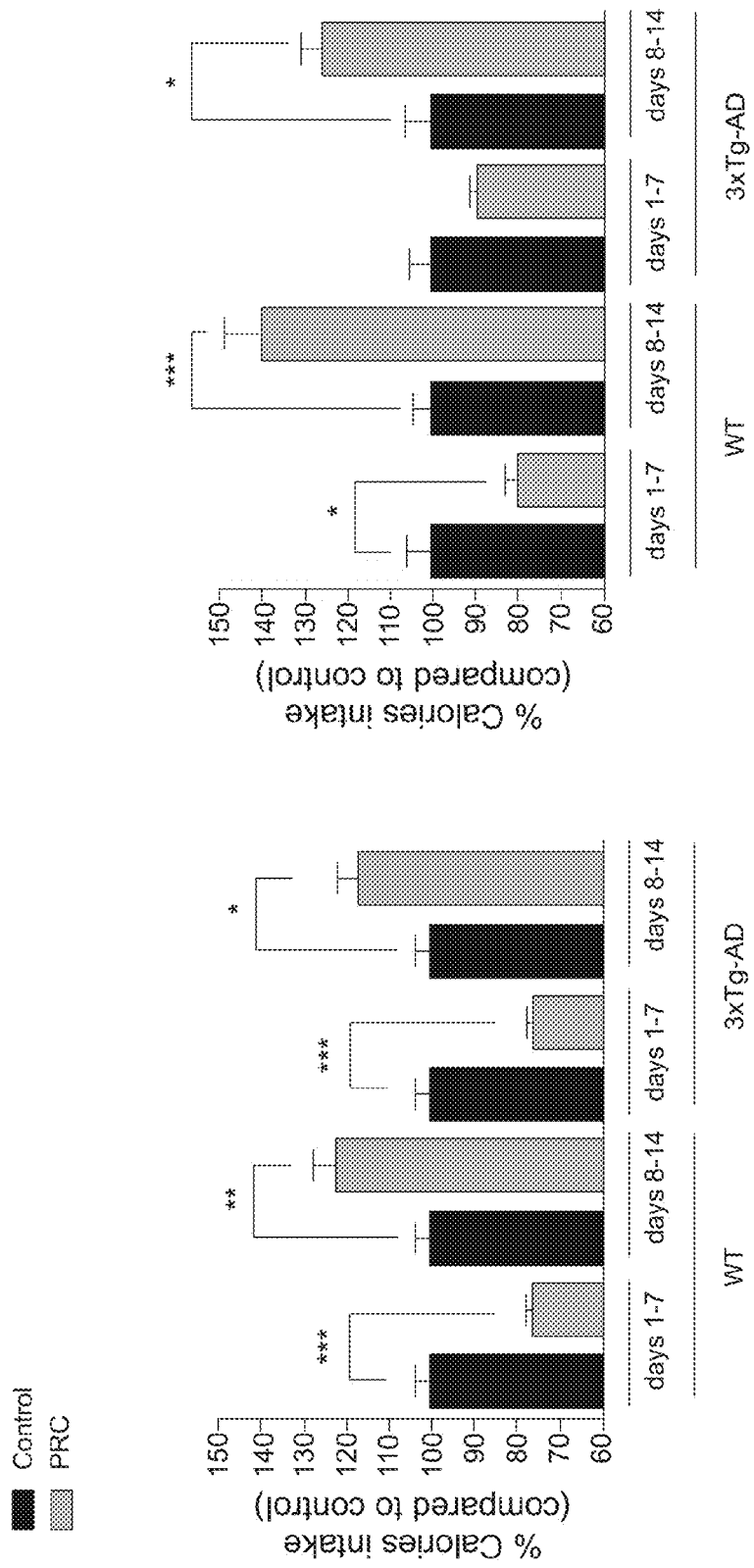
FIG. 21. Food intake was measured and used to calculate calories intake. Calories intake normalized for grams of body weight was scored daily at the beginning (weeks 1 and 2, A) and at the end of the dietary treatment (weeks 17-18, B) and was expressed as percentage calculated for the first week (days 1-7, PR diet) or the second week (days 8-14, re-feeding with normal diet) of diet cycle compared to control diets values scored during the same periods (*=p<0.05, =p<0.01, *=p<0.001)

Next, in order to investigate a possible impact of CR on the diet regimen, we monitored the calories intake at the beginning of the treatment (weeks 1 and 2) and at the end (weeks 17 and 18). At the beginning of the treatment (weeks 1 and 2), during the initial seven days of PR diet (days 1-7), average calorie intake was reduced by 24.3% in WT and 24.2% in 3xTg-AD mice (FIG. 21A, t-test: F=2.46 and 3.79 respectively, $p<0.001$). Diet lacking essential AA presents low palatability and most animals, including rodents, reduce their food intake after ingesting food lacking essential AA (Gietzen et al. 2007). However, during the re-feeding (days 8-14 of the PR cycle) average caloric intake was increased by 22.5% in WT and 17.2% in 3xTg-AD mice (FIG. 21A, t-test: F=1.53 and $p<0.01$ for WT, F=1.62 and $p<0.05$ for 3xTg-AD). A similar caloric intake profile was detected at the end of the treatment (weeks 17 and 18). Average caloric intake was decreased by 20.3% in WT and 10.5% in 3xTg-AD mice during the PR diet feeding (FIG. 21B, t-test: F=3.57 and $p<0.05$ for WT, F=27.78 and $p>0.05$ for 3xTg-AD). Again, the re-feeding period was coupled to a significant increase of caloric consumption (FIG. 21B, 40.1% in WT and 25.3% in 3xTg-AD t-test: F=3.47 and $p<0.001$ for WT, F=1.50 and $p<0.05$ for 3xTg-AD).

Figure 15:
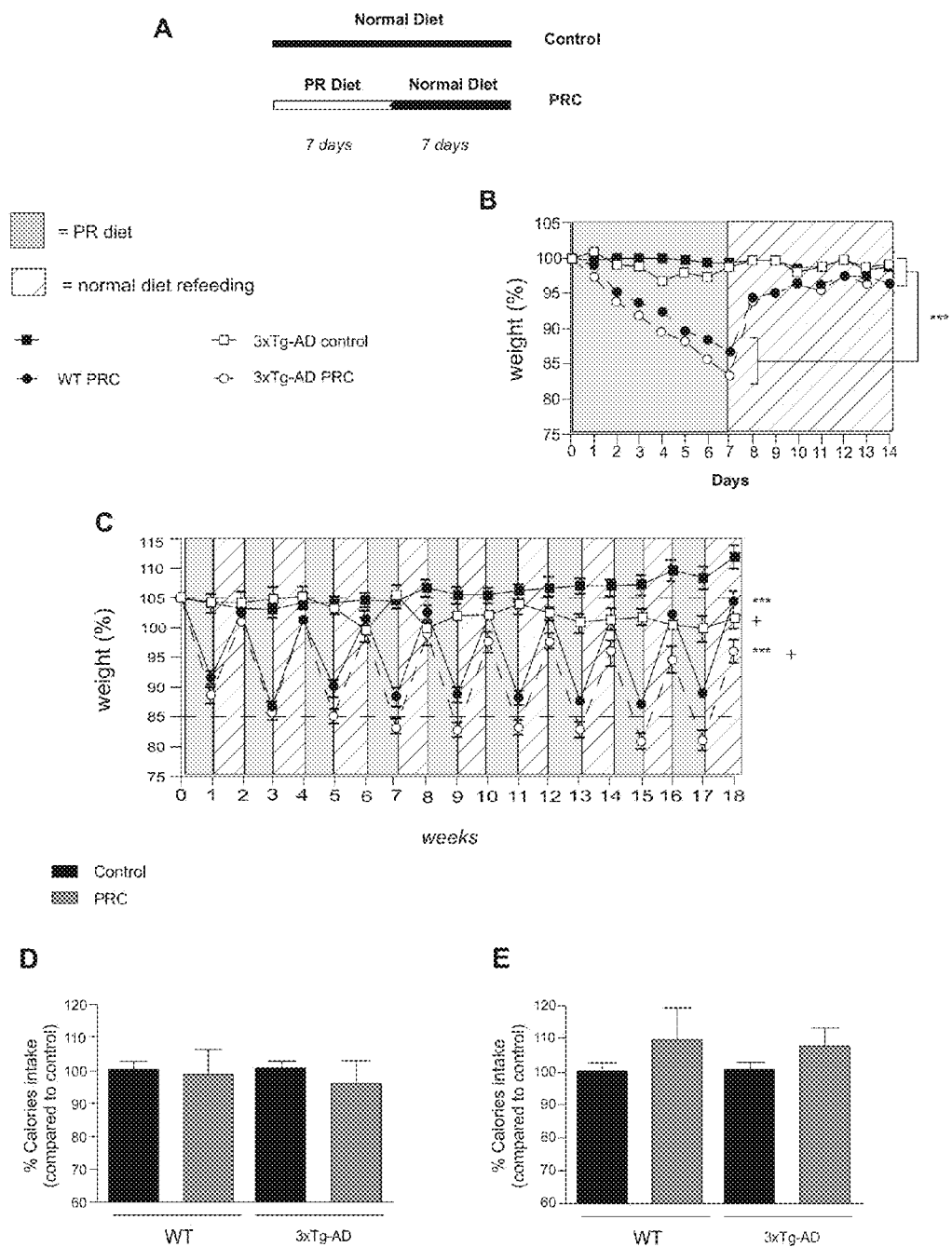
FIG. 15 provides body weight and calories intake profiles. (A) Diagram showing the Control and PRC dietary regimens used in the study. (B, C) Mouse body weights were measured and plotted as percentage of the initial weight scored at day zero (13-15 animals per group). The mice were weighed daily the first two weeks (B) and weekly for the remaining 16 weeks (C). (B) During the first two weeks of dietary intervention WT and 3×Tg-AD mice subjected to PRC regimen showed a significantly different body weight profile when compared with corresponding controls (*=p<0.001). (C) The different body weight profile between WT and 3×Tg-AD PRC groups and corresponding controls was maintained over the whole 18 weeks of dietary treatment (*=p<0.001). Moreover, we found a significant difference between body weight profiles of 3×Tg-AD control and PRC groups and corresponding WT animals (+=p<0.05, 3×Tg-AD control vs. WT control and 3×Tg-AD PRC vs. WT PRC). (D, E) Calories intake normalized for grams of body weight was scored daily at the beginning (weeks 1 and 2, D) and at the end of the dietary treatment (weeks 17-18, E) and was expressed as percentage calculated for the combined two weeks of PR diet and normal diet re-feeding.

The average caloric intake calculated by combining the values for the periods of both PR and normal diet re-feeding was similar to the average for the control regimen for both the first and the final weeks of the treatment (FIGS. 15D and 15E, t-test, $p>0.05$). We concluded that the PRC regimen was associated with a modest but unavoidable CR only during the PR diet phase (albeit with diminishing effect over the long-term), ranging between 19 and 17% for WT and 25.6 and 13% for 3xTg-AD, counterbalanced by an increase of calories intake during the following normal diet re-feeding period. The caloric intake profile of PRC intervention was different not only from CR regimen, but also from intermittent fasting (IR) (or every other day feeding—EODF—), another dietary restriction consisting in food deprivation for 24 h every other day and characterized by a 20-30% caloric intake reduction over time and beneficial effects similar to CR (Martin et al. 2006).

Figure 16:
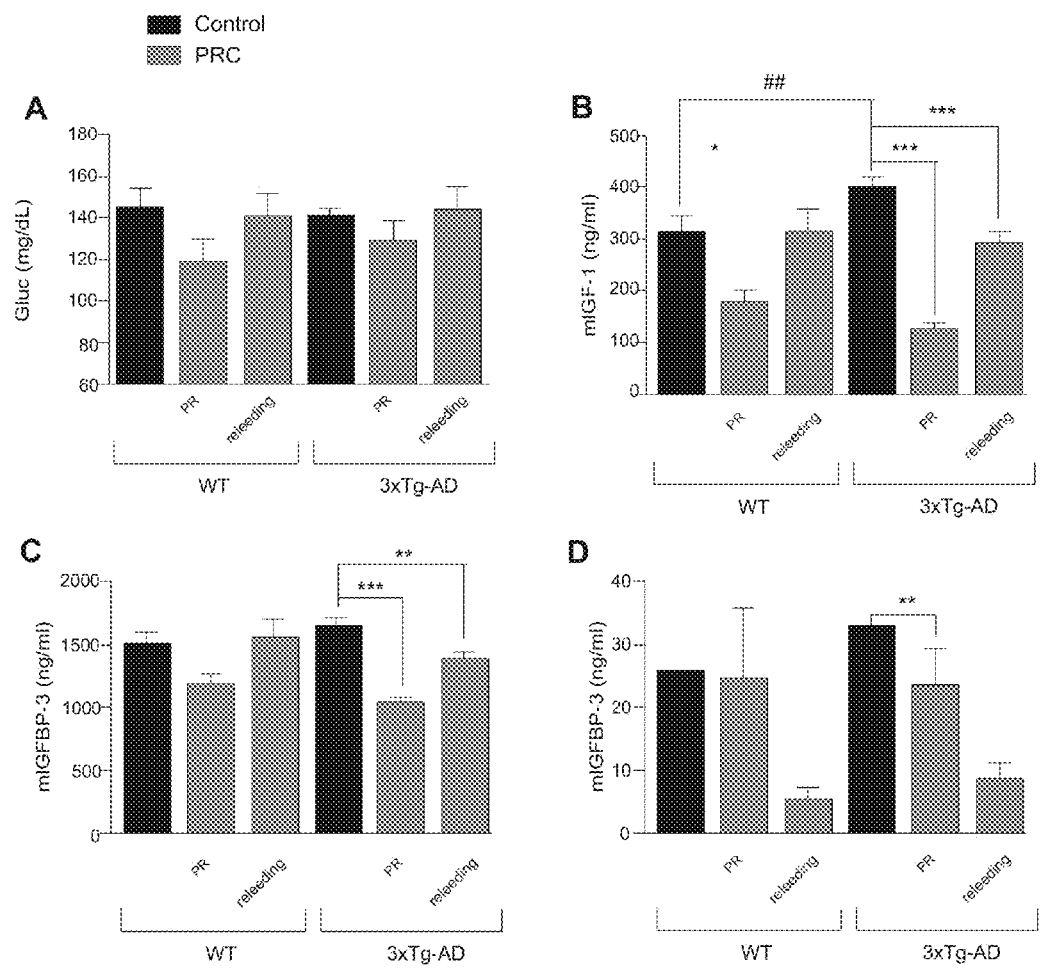
FIG. 16 illustrates that the PRC regimen does not modify blood glucose levels but modulate circulating IGF-1 and IGFBPs. (A) Blood glucose levels are expressed as concentration (mg/dL). No significant difference was detected between the experimental groups (6-13 samples per group). (B-D) Mouse Serum IGF-1 and IGFBP-1/3 levels are expressed as concentration (ng/mL) (3-7 samples per group). (B) WT mice sacrificed at the end of PR diet cycle displayed significantly lower IGF-1 levels when compared with corresponding control group (*=p<0.05). 3×Tg-AD mice showed a significant reduction in IGF-1 levels not only during the PR diet cycle but also during the normal diet re-feeding (*=p<0.001). We detect a significant difference between WT control and 3×Tg-AD control groups (##=p<0.01). (C) 3×Tg-AD mice showed a significant reduction in IGFBP-3 levels not only when fed with the PR diet (*=p<0.001) but also during the re-feeding cycle (=p<0.01). (D) We determined a significant increase in IGFBP-1 levels at the end of the PR cycle in 3×Tg-AD mice (=p<0.01)

PRC regimen does not cause a significant reduction of blood glucose levels. Blood glucose levels undergo remarkable changes during food restriction. For example, prolonged 20-40% CR in rodents can cause blood glucose reduction between 20 and 40% (Lee & Longo 2011). PRC regimen, however, did not promote a significant change in blood glucose levels, but caused a trend for glucose concentration reduction (17% in WT and 8% in 3xTg-AD mice) only at the end of the PR diet-feeding period (FIG. 16A). These data support our conclusion that the PRC effects are not due to CR.

PRC regimen reduces circulating IGF-1 levels by 30-70%, IGFBP-3 by 20-40% and increases IGFBP-1 by 3-8 folds in 3xTg-AD mice. Approximately 95% of the IGF-1 that acts on the brain has been shown to be derived from the liver (Yamamoto & Murphy 1995). Although IGF-1, its receptor and binding proteins are also present and locally produced in the brain, IGF-1 is actively transported across the blood-brain barrier, and therefore changes in circulating IGF-1 can lead to changes in IGF-1 input to the brain (Carro et al. 2000). The bioavailability and bioactivity of IGF-1 is regulated by IGF binding proteins (IGFBPs), a family of six proteins acting as carriers for IGFs (Jones & Clemmons 1995). Among the different binding proteins, IGFBP-3 and IGFBP-1 play a prominent role in IGF-1 bioavailability.

IGFBP-3 is quantitatively the most represented IGFBP, binding more than 80% of the circulating IGF-1 and protecting it from rapid degradation or elimination from the serum (Jones & Clemmons 1995).

Differently from the other IGFBPs, IGFBP-1 inhibits IGF-1 action by binding to IGF-1 itself and preventing its binding to IGF receptors (Jones & Clemmons 1995).

IGF-1 measurement revealed that 3xTg-AD had higher circulating levels of the hormone compared to WT (FIG. 16B, t-test: WT vs. 3xTg-AD, $p<0.05$). In 3xTg-AD mice IGF-1 levels were reduced by PRC regimen not only during the PR diet period (FIG. 16B, 70% reduction, 3xTg-AD control vs. 3xTg-AD PRC at the end of PR diet cycle, $p<0.001$) but also during the normal diet re-feeding (FIG. 16B, 28% reduction, 3xTg-AD control vs. 3xTg-AD PRC at the end of normal diet re-feeding cycle, $p<0.001$). A similar but weaker effect was detected in WT mice at the end of PR diet (FIG. 16B, 44% reduction, WT control vs. WT PRC at the end of PR diet, $p<0.05$). Circulating levels of IGFBP-3 were significantly decreased by the PRC regimen at the end of both PR diet and re-feeding cycles in 3xTg-AD mice (FIG. 16C, 37% reduction, 3xTg-AD control vs. 3xTg-AD PRC at the end of PR cycle, $p<0.001$; 17% reduction, 3xTg-AD control vs. 3xTg-AD PRC at the end of normal diet re-feeding, $p<0.01$). In WT mice, although we noticed a trend for a reduction during PR diet feeding, PRC intervention failed to cause significant changes in IGFBP-3 levels. Finally, in 3×Tg-AD mice PRC regimen promoted a significant increase of circulating IGFBP-1 levels at the end of PR cycle (FIG. 16D, 8-fold increase, 3×Tg-AD control vs. 3×Tg-AD PRC at the end of PR cycle, p<0.01). Albeit we observed a trend for an increase of IGFBP-1 during the PR diet, PRC regimen did not cause a significant modulation of its serum levels in WT mice.

Taken together, these results clearly indicate that 18-19 weeks of PRC regimen promoted a strong modulation of IGF-1 and IGFBPs whose final effect was a reduction of circulating levels of IGF-1. The effect was greater in 3×Tg-AD mice.

Figure 17:
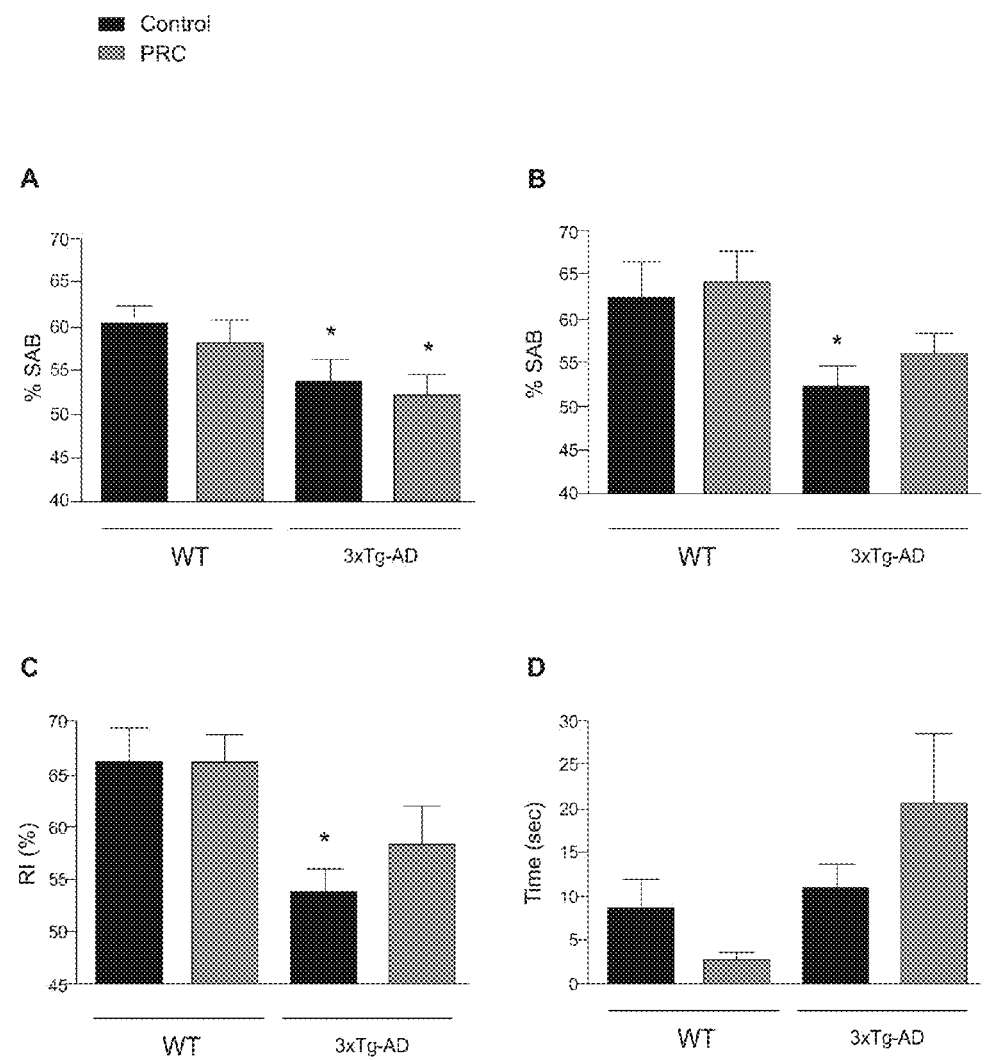
FIG. 17 illustrates that PRC regimen alleviates age-dependent behavioral changes in 3×Tg-AD mice. (A and B) Shown is SAB (spontaneous alternation behaviour) percentage, obtained testing the mice with the Y-maze test at 8-9 months of age, before any dietary treatment (A), or at 12.5-13-5 months of age, after 18 weeks of PRC regimen (B). (A) 3×Tg-AD mice already showed working memory impairment performing significantly worse than WT control group (*=p<0.05, 13-14 mice per group). (B) Only 3×Tg- AD control group performed worse than WT groups (*=p<0.05, compared with WT groups, 13-14 mice per group). (C) NOR test was used to calculate RI (recognition index). RI scored for 3×Tg-AD control animals was significantly lower than values calculated for WT groups (*=p<0.05, compared with WT groups, 12-14 mice per group). (D) EPM test was used to score the time spent by the rodents in open arms. No significant difference was detected between the experimental groups (13-14 mice per group)

PRC regimen alleviates age-dependent working memory deficits in 3×Tg-AD mice. In order to determine whether the PRC regimen is associated with improved cognitive performances, we performed the Y-maze (hippocampus dependent working memory) in both 3×Tg-AD and WT mice. The mice were tested before the initiation of the dietary intervention (age 8-9 months) and every month of the treatment. In agreement with the literature (Rosario et al. 2006), 8-9 month old 3×Tg-AD male mice showed cognitive impairment detectable with Y-maze when compared with age-matched WT (FIG. 17A One-way ANOVA: F=3.46, p<0.05 3×Tg-AD groups vs. WT control). At the age of 12.5-13.5 months 3×Tg-AD control mice still exhibited a significant working memory deficit in comparison with WT mice, whereas 3×Tg-AD mice subjected to 18 weeks of PRC regimen did not, indicating a protection effect provided by the diet (FIG. 17B, One-way ANOVA: F=3.46, p<0.05 3×Tg-AD control vs. WT control). Interestingly, after 12 weeks of treatment, the 3×Tg-AD PRC mice still displayed a significant memory deficit compared to WT, suggesting that the dietary intervention may require a latency period before becoming effective (FIG. 22A, One-way ANOVA: F=2.41, p<0.05 3×Tg-AD groups vs WT control). We did not find significant differences in the number of arm entries among the WT and 3×Tg-AD groups, suggesting that diets do not interfere with activity levels of the rodents (FIG. 23A, One-way ANOVA: F=4.23).

PRC regimen alleviates short term spatial memory deficits in 3×Tg-AD mice. The described mice were tested for short term spatial memory using the Novel Object Recognition (NOR) test. NOR test was performed once at the end of the treatment (age 12.5-13-5 months of age). The test relies on the natural rodent behavior to preferentially explore novel objects and has been used to study working spatial memory in 3×Tg-AD mice (Gulinello et al. 2009). On trial 1 of the test the rodents were allowed to explore a box containing two identical objects and the time spent exploring them was recorded. As expected, no significant preference between the two objects was detected in the different experimental groups (FIG. 23B, p>0.05, object A vs. object B, t-test). At the end of the trial the mice were returned to their home cages for three minutes, then placed again into the box where one of the objects was replaced with a novel one (trial two) and the time spent exploring the objects was recorded again in order to calculate RI values. 3×Tg-AD control mice showed a significantly lower RI compared to WT, whereas 3×Tg-AD animals on PRC regimen did not (FIG. 17C, One-way ANOVA: F=2.43, p<0.05 3×Tg-AD control vs. WT control). These results indicate that PCR can alleviate the spatial memory deficits caused by the 3×Tg-AD mutations in mice.

PRC regimen does not affect anxiety in the studied mice. To function properly, the CNS requires the AA found in the diet, including Tryptophan, Phenylalanine, Tyrosine, Histidine, Glutamine and Arginine, as substrates for the synthesis of various neurotransmitters and neuromodulators and the availability of some of them can play an important role in mood regulation (Young 19%).

To analyze the impact of the diet on anxiety, we tested WT and 3×Tg-AD mice on the Elevated Plus Maze (EPM), a test used to analyze behavioral modifications caused by proteins undernutrition (Young 1996). The test was performed before the treatment (age 8-9 months) and after 18 weeks of dietary intervention (age 12.5-13.5) and the time spent in the open arms scored. More time spent in the open arms reflects a lower level of anxiety.

Figure 18:
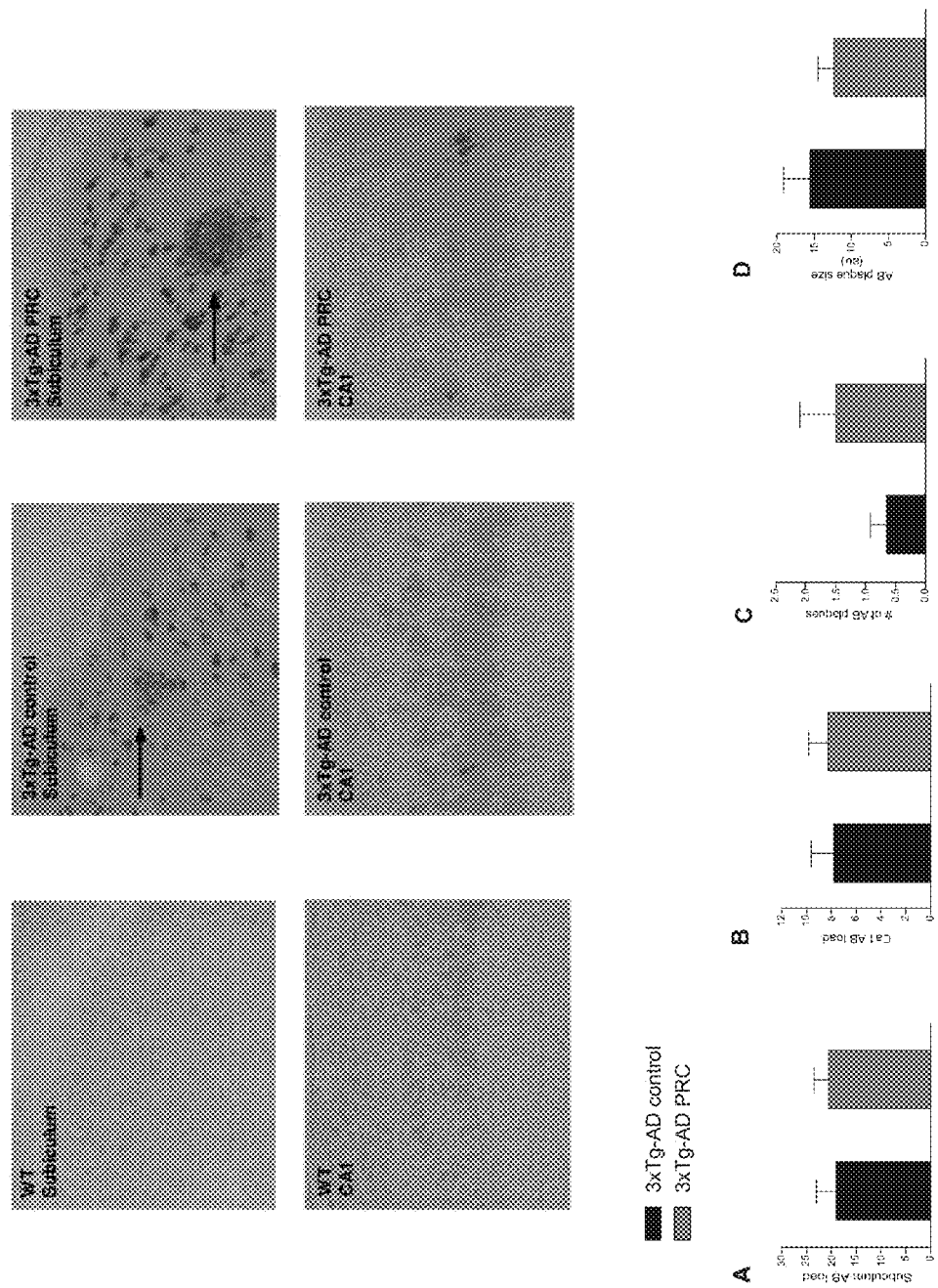
FIG. 18 illustrates that PRC regimen does not slow down Aβ accumulation in 3×Tg-AD mice hippocampus. Representative images showing Aβ immunoreactivity in subiculum or CA1 hippocampus regions of 12.5-13.5 month old WT control, 3×Tg-AD control and 3×Tg-AD PRC mice are shown. Aβ plaques are indicated by arrows. Quantification of Aβ accumulation by load values in subiculum and hippocampus CA1 regions is showed in (A) and (B) respectively. Number and size of Aβ plaques are shown in (C) and (D). (10-12 (A, B, C) and 5-7 (D) samples per group)
Figure 22:
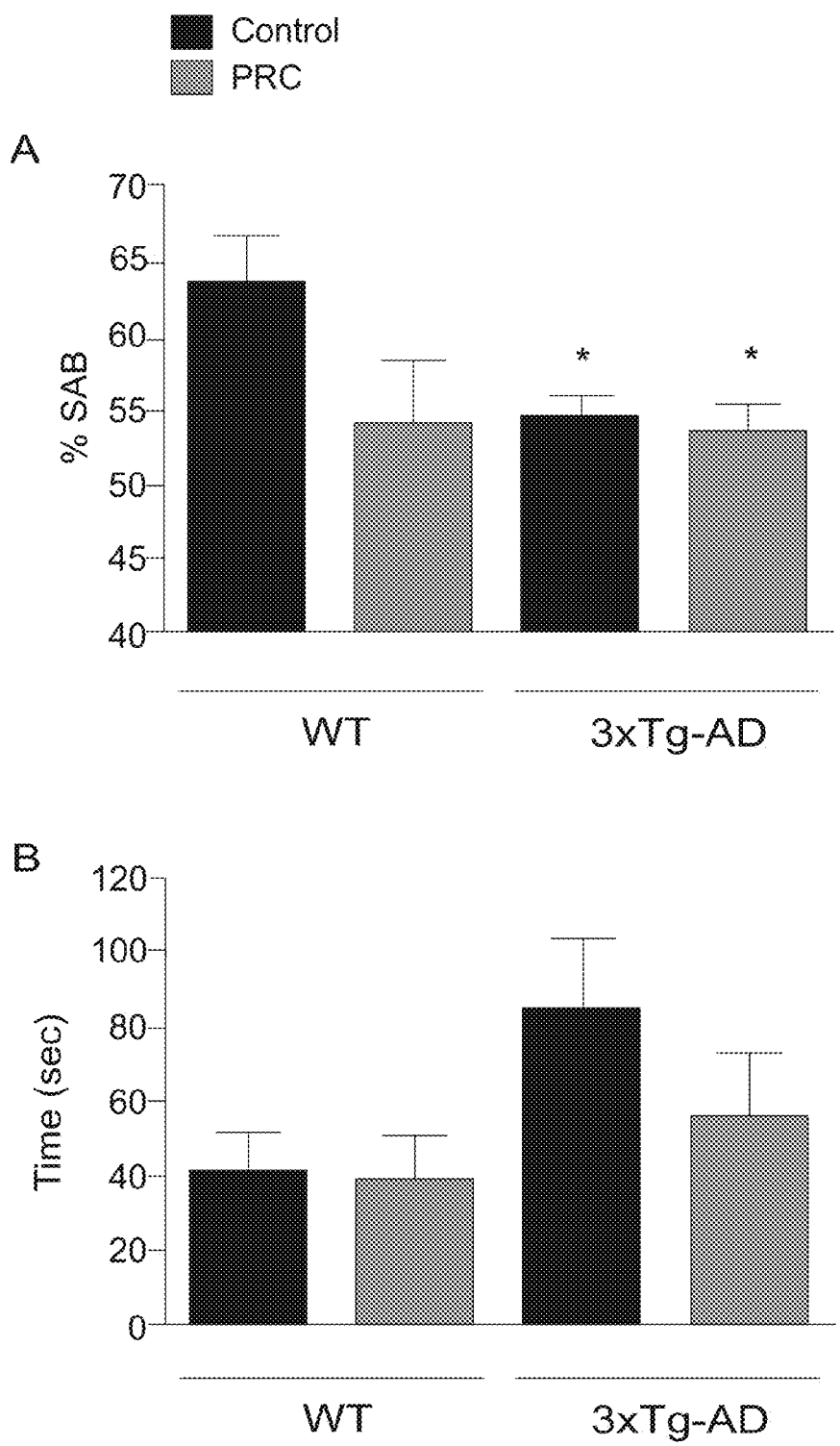
FIG. 22. (A) Shown is SAB (spontaneous alternation behaviour), obtained testing the mice with Y-maze after 12 weeks of PRC regimen. 3×Tg-AD groups performed worse than WT control group (*=p<0.05. 13-14 mice per group). (B) Shown is the time spent in open arms scored testing the mice with EPM at 8-9 months of age, before any dietary treatment. We did not detect significant difference in the scored parameter (13-14 mice per group)
Figure 23:
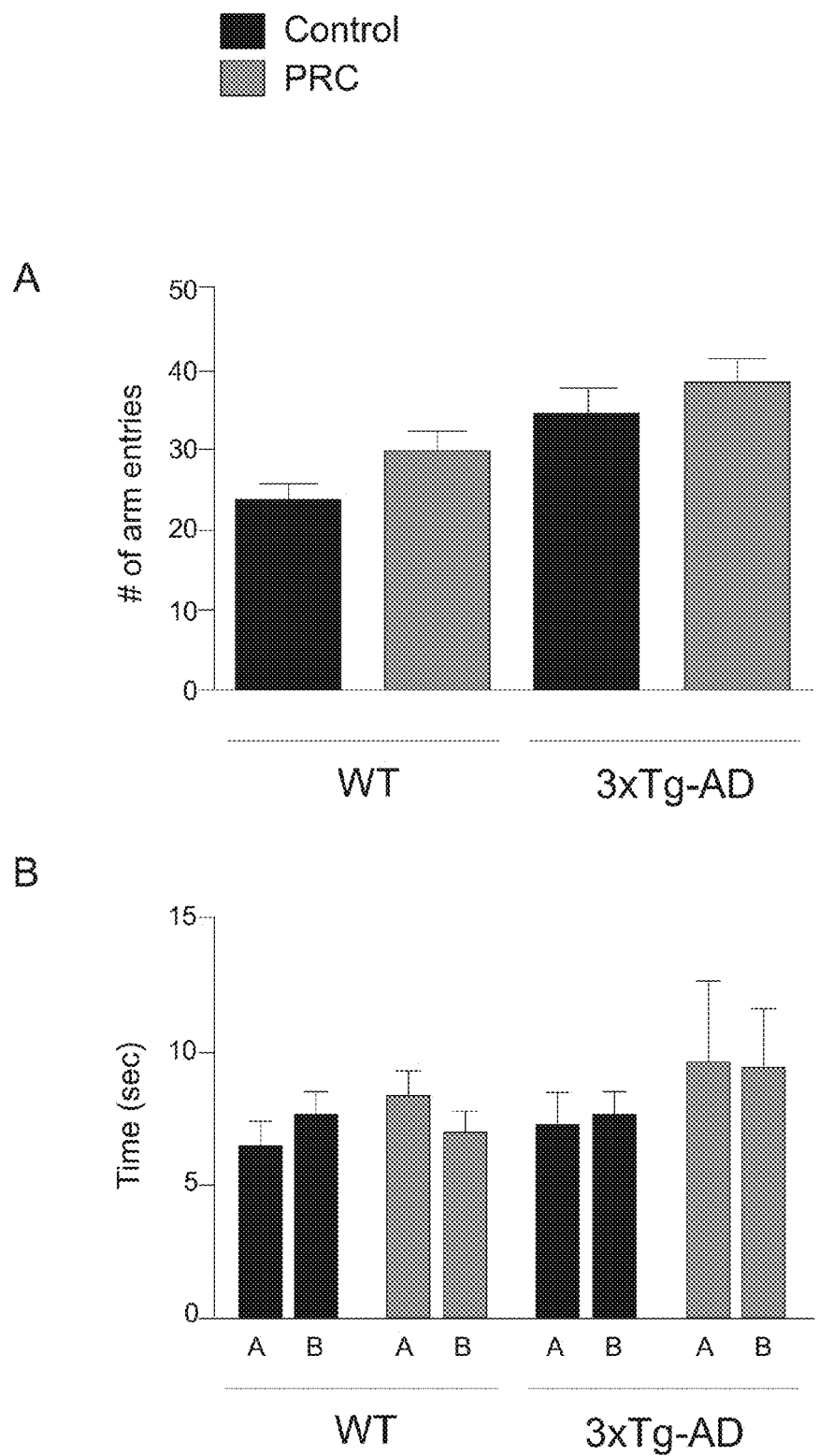
FIG. 23. After 18 weeks of diet intervention the mice were tested on Y-maze and NOR tests. (A) Shown is the number of arm entries scored during the Y-maze task. We did not detect significant difference among WT and 3×Tg-AD groups (13-14 mice per group). (B) On trial 1 of NOR test the rodents were allowed to explore a box containing two identical objects (object A and object B) and the time spent exploring them was recorded. No significant difference was found in the time the animals dedicated to explore the different objects (t-test: time object A vs. time object B, 12-14 mice per group).

Before the diet intervention no significant difference was detected in the scored parameter among the experimental groups in both 3×Tg-AD and WT (FIG. 22B, t-test, F=1.65, p>0.05 control vs. PRC). After 18 weeks of diet treatment we noticed a reduction in the time the rodents spent in the open arms that indicates an increased level of anxiety. The large difference between the scored parameter at the baseline and at the end of the dietary intervention is common to all the experimental groups and may be the result of the mice manipulation. However we still did not detect any significant difference in the time spent in the open arms (FIG. 17D, t-test, F=2.45, p>0.05 control vs. PRC). Although we cannot completely rule out possible side effects on mood regulation caused by protein restriction, these results show that the diet intervention does not cause significant anxiety level change in the treated mice. PRC regimen does not reduce Aβ accumulation in the 3×Tg-AD mice hippocampus. To determine whether the PRC regimen was coupled with a decrease in Aβ accumulation in the brain of aged 3×Tg-AD mice, brain sections were immunostained using a specific antibody against Aβ. We did not find any significant difference in Aβ IR between control and PRC regimens neither in the subiculum (FIG. 18A, t-test: F=2.60, p=0.76) nor in the CA1 (FIG. 18B, t-test: F=1.73, p=0.87) hippocampus regions. Moreover, there was no difference in the number (FIG. 18C, t-test: F=4.09, p=0.17) or the size of Aβ plaques between the control and PCR diet groups (FIG. 18D, t-test: F=1.76, p=0.44).

Figure 19:
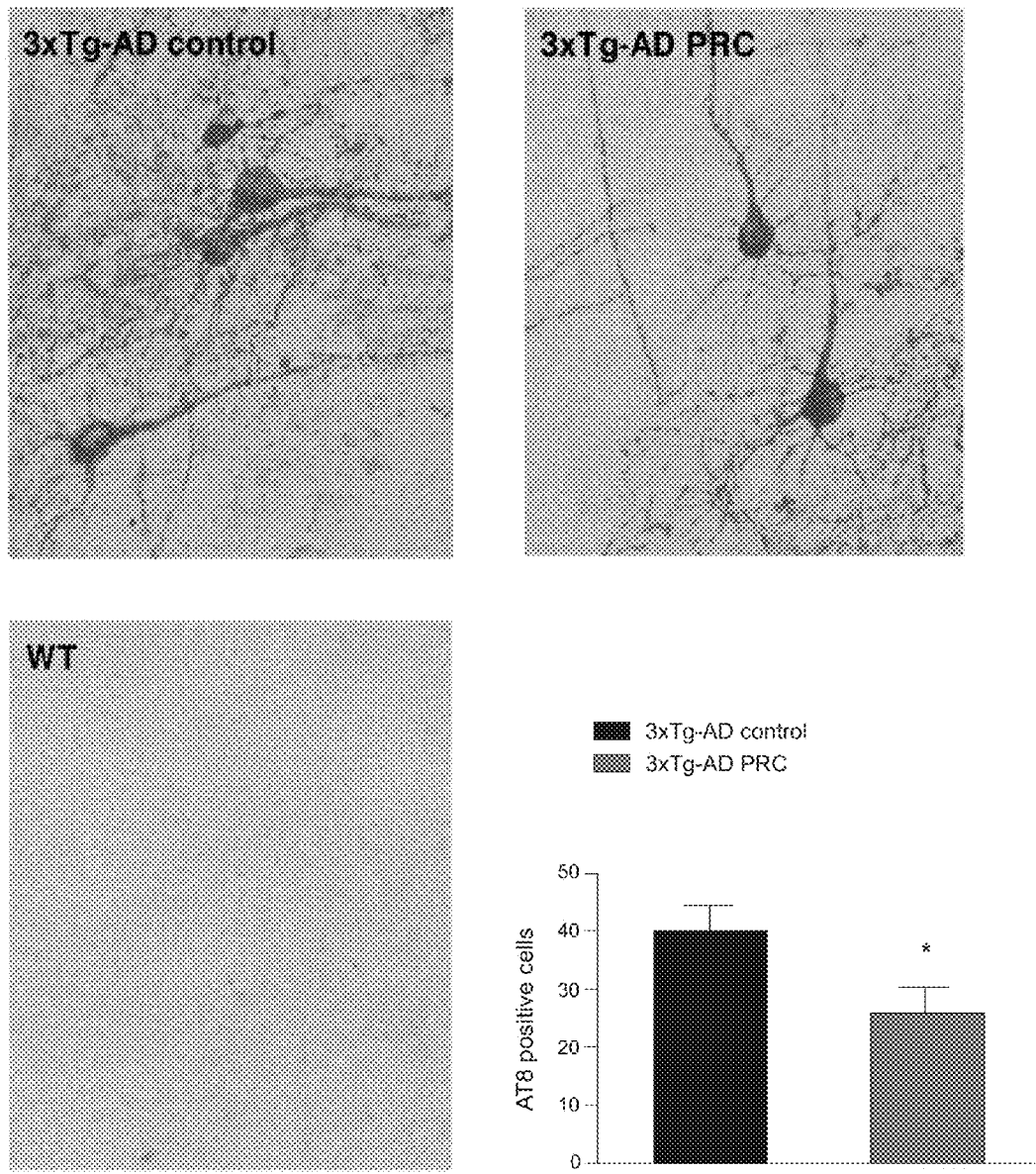
FIG. 19 illustrates that PRC regimen reduces AT8 positive neurons in 3×Tg-AD mice hippocampus. Representative images showing hippocampus sections immunostained with AT8 antibody, which recognizes abnormally phosphorylated tau, of 12.5-13.5 month old 3×Tg-AD control, 3×Tg-AD PRC and WT control mice are shown. Quantification of numbers of AT8-immunoreactive cells is shown (*=p<0.05, 3×Tg-AD PRC vs 3×Tg-AD Control, 10-12 samples per group)

PRC regimen reduces tau phosphorylation in 3×Tg-AD mice hippocampus. In addition to Aβ accumulation 3×Tg-AD mice develop au age-dependent accumulation of phosphorylated tau that is believed to be central in the progressive cognitive impairment observed in AD. In order to investigate the effect of PRC regimen on levels of tau phosphorylation, we quantified the number of cells immunoreactive with the AT8 antibody, which recognizes the phosphorylation of tau protein at Ser 202 and 305 that is associated with AD pathology (Goedert et al. 1995). We found that mice subjected to PRC regimen showed a significant reduction in phosphorylated tau levels compared with mice fed with the normal diet (FIG. 19, t-test: F=1.31, p<0.05). These results indicate that PRC may inhibit tau phosphorylation either independently or downstream of Aβ.

PRC regimen does not reduce microglia activation in 3×Tg-AD mice hippocampus. Next we decided to investigate whether the PRC regimen can affect brain inflammation. Neuroinflammation is a prominent feature of AD and an increase of markers of microglia activation has been reported in AD rodent models including 3×Tg-AD mice. First, we quantified the presence of activated microglia in the hippocampus of the studied mice using the microglia-specific marker CD11b. Our data confirmed a dramatic increase of the total number of CD11b-ir cells in the hippocampus of 3×Tg-AD mice compared with WT (FIG. 20A, *=p<0.001 3×Tg-AD control vs. WT control). However, the total number of CD11b-ir cells in 3×Tg-AD PRC mice did not differ from the value scored in 3×Tg-AD mice fed with normal diet (FIG. 20A, p>0.05 3×Tg-AD PRC vs. 3×Tg-AD control, *=p<0.001 3×Tg-AD PRC vs. WT control).

Figure 20:
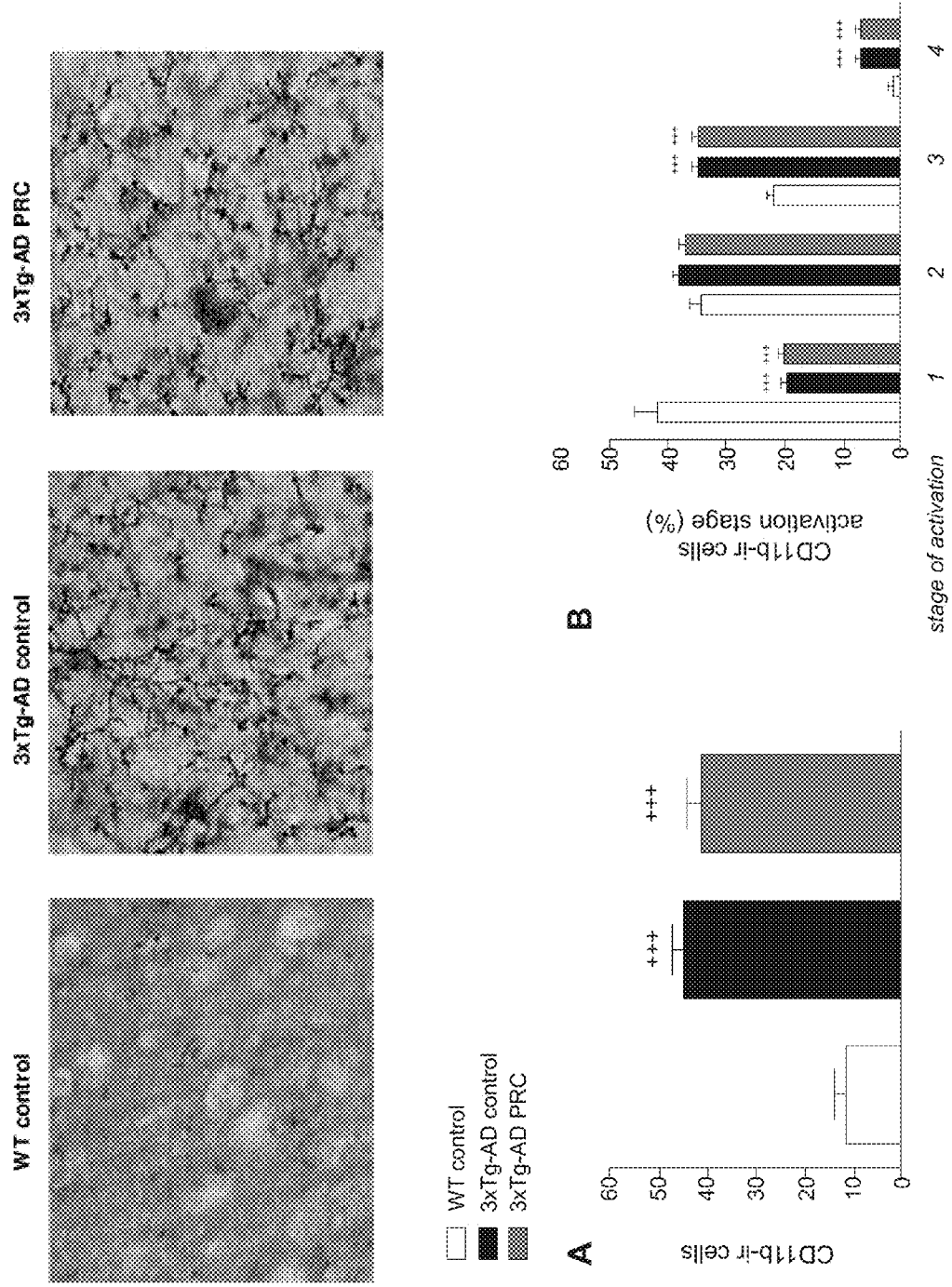
FIG. 20 illustrates that PRC regimen does not modulate total number nor activation stages of CD11b-ir cells in 3×Tg-AD mice hippocampus. Representative images showing CD11b immunoreactive (CD11b-ir) microglia in hippocampus sections of 12.5-13.5 month old WT control, 3×Tg-AD control and 3×Tg-AD PRC mice are shown. Quantification of total number of CD11b-ir cells in the described experimental groups is shown in FIG. 20A. Percentage of different microglia activation stages (from 1 to 4) is represented in FIG. 20B (For all the figures: ***=p<0.001 compared with WT, 5-10 samples per group)

Second, we quantified microglial activation based on a four-stage morphological classification ranging from resting, activated ramified, amoeboid, to phagocytic cells (Zhang et al. 2011). 3×Tg-AD control mice showed a prevalence of more activated stages when compared with WT (FIG. 20B: stage 1, 3×Tg-AD control 20% vs. WT control 42%; stage 3, 3×Tg-AD control 35% vs. WT control 22%; stage 4, 3×Tg-AD control 7% vs. WT control 1%. *=p<0.001 3×Tg-AD control vs. WT control). Again, PRC regimen did not influence microglia morphology in the hippocampus of 3×Tg-AD mice (FIG. 20B, p>0.05 3×Tg-AD PRC vs. 3×Tg-AD control, *=p<0.001 3×Tg-AD PRC vs. WT control). These data indicate that PRC do not affect tau phosphorylation and behavioural defects in 3×Tg-AD mice by altering pro-inflammatory pathways.

Discussion

Our findings provide evidence that weekly cycles of normal diet and protein restriction regulate circulating levels of IGF-1 and IGFBPs but also reduce tau phosphorylation, and alleviate age-dependent memory deficits in an animal model of AD.

Although PRC could not completely reverse the cognitive decline in the AD mouse model, the results are important in light of the fact that we started the PRC treatment on mice already showing significant cognitive impairment and AD-like pathology. 3×TgAD mice fed with normal diet displayed hampered working and spatial memory when compared to non-transgenic control mice. In contrast, 3×TgAD mice maintained on PRC regimen for 18-19 weeks did not perform significantly worse than WT mice, Moreover, it is worth noting that all the behavioural tests were performed during the normal diet re-feeding period. Assuming a connection between transient circulating hormones level and positive memory performance, we cannot exclude that we could score even better results during the PR cycle. Interestingly, two important features of AD pathology, Aβ accumulation and microglia activation, were not modified in the hippocampus of protein restricted 3×Tg-AD mice, On the other hand, we found that 3×Tg-AD subjected, to PRC regimen exhibited reduced phosphorylated tau levels when compared with 3×Tg-AD mice fed with normal diet. Evidence indicates a strong association between phosphorylated tau levels and cognitive deficits in human subjects affected by AD and mild cognitive impairment (MCI) (de Leon et al. 2006). A reduction of tau phosphorylation may alleviate memory impairment as indicated by studies conducted on AD models (Roberson et al. 2007).

The beneficial effect of reduced tau phosphorylation independently of Aβ deposition may be explained by the fact that Aβ pathology precedes tau pathology in this AD model (Oddo et al. 2003). In fact, whereas Aβ deposition is present by 6 months of age in hippocampus of 3×Tg-AD mice, it is not until approximately 12 months that AT8 immunoreactivity for phosphorylated tau is easily detectable (Oddo et al. 2003). Thus, levels of Aβ in 3×Tg-AD brains may not have been influenced by PRC intervention, as also reported in previous studies on CR (Patel et al. 2005; Wang et al. 2005; Halagappa et al. 2007; Mouton et al. 2009), because of the advanced stage of Aβ pathology at the starting of the treatment.

In 3×Tg-AD brains extraneuronal Aβ also precedes microglia activation and plays a major role in the onset of inflammation (Kitazawa et al. 2005). Therefore, the failure to detect a beneficial effect of protein restriction on microglia activation, as observed in previous studies on CR (Wang et al. 2005), may be caused by the late onset of the dietary intervention or by the effects of other components of the diet (glucose etc.) on inflammation.

The protein restriction regimen was coupled to a modulation of circulating levels of IGF-1, IGFBP-3 and IGFBP-1 that, at least in part, could be responsible for the improved outcome in AD mice.

Recently, we have published on the reduced incidence of cancer and diabetes in GHR and IGF-1 deficient subjects (Guevara-Aguirre et al. 2011), in agreement with results from dwarf GHR/IGF-1 deficient mice and Tor/Sch9 deficient yeast (Brown-Borg et al. 1996; Coschigano et al. 2000; Fabrizio et al. 2001; Fontana et al. 2010). Although the known world population of GHRDs is small (less than 400) and few of them have reached ages above 90, no cases of AD have yet been reported for GHRDs, raising the possibility that their nervous system may also be protected from aging and dementia. Thus, methods that down-regulate GHR/IGF-1 signalling should be tested for their potential to protect against aging and age-related diseases.

On the other hand, IGF-1 is critical in brain maintenance and is involved in major aspects of CNS, such as neuronal development and plasticity. Local IGF-1 availability in the brain can play a neuroprotective role in AD increasing neurogenesis and neuronal survival and modulating brain Aβ clearance (Garro et al. 2002).

Our serum IGF-1 measurement showed significantly higher levels of the circulating hormone in 3×Tg-AD mice compared to WT group. Increased circulating IGF-1 has been also observed in AD patients (Vardy et al. 2007) and may be caused by an attempt to overcome a state of resistance to IGF-1 signalling characterized by the loss of sensitivity to the hormone's action (Garro & Torres-Aleman 2004). Recently, Arnold and co-workers provided direct demonstration that AD brain is IGF-1 resistant and showed that activated forms of molecules downstream the insulin/IGF-1 signalling are dramatically elevated in AD patients brain (Talbot et al. 2012).

Although in this study we did not analyse brain IGF-1 signalling, we speculate that the chronic systemic reduction in IGF-1 levels induced by the PRC regimen may increase IGF-1 sensitivity in 3×Tg-AD brain leading to a significant beneficial effect on cognition and tau pathology. In agreement with our results, organotypic slices from hippocampi of adult Ames dwarf mice, characterized by increased IGF-1 protein levels in the hippocampus and circulating IGF-1 deficiency, are resistant to Aβ induced tau hyperphosphorylation (Schrag et al. 2008). In addition, aged Ames and GHR-KO mice show better memory performance compared to age-matched WT (Kinney et al. 2001, Sharma et al. 2010) and Ames mice exhibit increased neurogenesis following a hippocampal insults (Sharma et al. 2012), suggesting that reduction of circulating IGF-1 together with higher level of the hormone in the brain may provide additional protection and promote cognitive function via neuronal proliferation.

In conclusion, the results presented here show that PRC regimen is an intervention able to alleviate AD-like symptoms in 3×Tg-AD mice possibly by modulating tau phosphorylation. Notably, the diet intervention is not coupled to CR and does not cause apparent side effects in 3×Tg-AD mice. These findings, combined to the fact that the dietary intervention was effective on mice already showing significant AD-like symptoms, raise the possibility that PRC, more than CR intervention, could be clinically translatable into a long-term treatment for patients affected by early-moderate AD. Treatment conditions applicable to patients should be established by determining the length of time required to have similar changes in IGF-1 and IGFBP-1 in humans as it is achieved by 1 week protein restriction in mice. In the future more studies are needed to further investigate the safety of this promising treatment and to elucidate its mechanism of action.

Experimental Procedures

Diet Composition

The following experimental diets have been used:
Normal diet (Harlan Teklad LM-485, Indianapolis, Ind., USA).
Protein Restriction (PR) Diet (diet lacking 9 AA: Isoleucine, Leucine, Lysine, Methionine, Phenylalanine, Threonine, Tryptophan, Valine, Arginine) (Teklad, Indianapolis, Ind., USA).

Differently from the normal diet, PR diet does not contain proteins and the nitrogen sources are represented only by free AA. The two diets are similar in nitrogen content, thus similar in caloric density (Table 2). In order to maintain equivalent nitrogen content in normal and PR diets, we balanced the lack of designated AA by increasing the quantity of the remaining ones (Table 7).

Essential AA cannot be synthesized de novo by mammals and therefore must be supplied through the diet. Long-term essential AA depletion can cause severe health problems and eventually lead to death. Regimen of alternating normal and PR diets was chosen to overcome chronological depletion of essential AA. The following dietary regimens were used (FIG. 15A): Control (normal diet), Protein Restriction Cycles (PRC) (7 days of PR diet followed by 7 days of normal diet re-feeding)

Mice and Experimental Design

3×Tg-AD and corresponding wild-type (WT) (C57BL/6/129S) mice were used in this study. 3×Tg-AD mice overexpress three human genes harbouring mutations linked to AD (presenelin-1, APP) and frontotemporal dementia (tau), that result in the development of both Aβ plaques, hyperphosphorylated tau tangles as well as the age-dependent Alzheimer-like cognitive impairment (Oddo et al. 2003). Colonies of the described mice were bred and maintained at the University of Southern California in accordance with National Institutes of Health guidelines on use of laboratory animals and an approved protocol by the University of Southern California (Los Angeles, Calif.) Institutional Animal Care and Use Committee. Male 3×Tg-AD and WT mice were single caged (in order to monitor the food intake) few days before the beginning of the diet regimen. At the age of 8-9 months (at this age cognitive deficits, such as working memory impairment, are detectable in 3×Tg-AD mice FIG. 22A and (Rosario et al. 2006)) 3×Tg-AD and WT animals were divided in two groups (12-14 mice per group) and assigned to the dietary regimens described above.

Mice were randomly assigned to dietary groups based on body weight (mean body weight of 29.6 g for 3×Tg-AD, 32.4 g for WT). The rodents were maintained on 12 h light/dark cycles and provided ad libitum access to water and the described diets. Food was refreshed according with dietary regimen every 2 or 3 days (day 0, 2 and 4 of 7 days diet cycle). The animals were subjected to the alternate regimen for 18 or 19 weeks.

During the different dietary regimes body weights were measured weekly. Furthermore, mice weight and food intake were measured every day at the beginning of dietary treatment, on week 1 and 2, and at the end, on week 17 and 18. Mice subjected to the different diet regimens that failed to regain weight during the re-feeding period or showed signs of discomfort were removed from the study (one 3×Tg-AD mouse from Control group and one from PRC group were excluded).

Before the start of the treatment and every 4 weeks during the dietary regimen, the mice were tested with Y-maze (hippocampus dependent working memory) and Elevated Plus Maze (anxiety detection). At the end of the dietary intervention, the animals were tested also with Object Recognition Test (short term spatial memory). In order to minimize any possible abnormal behaviour caused by difference in diet compositions, the behavioral tests were performed during the normal diet re-feeding period.

At the end of diet treatment the mice were sacrificed under isoflurane anesthesia and blood and brains collected. Blood was collected by tail-snip for glucose measurement and by heart puncture for hormones analysis. All the serum obtained was kept at −80° C. until assayed. The brain was divided in two: one hemisphere was dissected, frozen and stored at −80° C., the other was immersion-fixed in fresh 4% paraformaldehyde/0.1 M PBS for 48 hours and then stored at 4° C. in 0.1 M PBS/0.2% sodium azide.

Glucose Measurement

Glucose levels were measured before the sacrifice on blood collected by tail-snip using a Precision Xtra blood glucose monitoring system (Abbott, Abbott Park, Ill., USA).

IGF-1, IGFBP-3 and IGFBP-1 Measurement

Mouse serum IGF-1 and IGFBP-3 levels were measured by in-house mIGF-1 and mIGFBP-3 ELISAs, as previously described (Hwang et al. 2008). The IGF-1 assay has a sensitivity of 0.1 ng/ml and no cross reactivity with IGF-2. The intra-assay and inter-assay coefficients of variations (CV) were <10% in the range from 1 to 10 ng/ml. The mouse IGFBP-3 assay has a sensitivity of 0.2 ng/ml. The CVs of intra-assay and inter-assay were <6% and <8%, respectively, in the range of 1 to 6 ng/mL. Mouse IGFBP-1 serum levels were measured by in-house ELISA assays using recombinant mouse proteins and antibodies from R&D Systems (MAB 1240 as capture antibody and BAF 1240 as detection antibody, R&D Systems, Minneapolis, Minn., USA). The assay has a sensitivity of 0.1 ng/ml and the CVs of in intra- and inter-assay were <10%, respectively.

Behavioural Tests:

Y-maz:

12-14 mice per group were tested for working memory using a Y-maze_(arms 21 cm (long) by 4 cm (wide) with 40-cm walls). The mice were tested before the dietary intervention, at the age of 8-9 months, and every month of treatment till the age of 12.5-13.5 months. The test started by placing the rodent in one of the arms of the maze. The mouse was allowed to explore freely the environment for 8 minutes and the total numbers of arm entries and arm choices were recorded. An arm choice was defined as both forepaws and hindpaws fully entering the arm. Spontaneous alternation behaviour (SAB) score was calculated as the proportion of alternations (an arm choice differing from the previous two choices) to the total number of alternation opportunities (Carroll et al. 2010; Rosario et al. 2006).

Novel Object Recognition (NOR) Test 12-14 mice per group were tested for short-term spatial memory using the Novel Object Recognition (NOR) test. The mice were tested once at the end of dietary treatment at the age of 12.5-13.5 months. The maze consists in an opaque plastic box measuring 61 cm (length)×36 cm (width)×30 cm (height). The test is based on the protocol described by Gulinello and co-workers (Gulinello et al. 2009). Briefly, on the first day of the test (habituation day) the mice were placed into the box and allowed to explore the field for 5 minutes. Twenty-four hours later (test day) habituated mice were placed again into the box at the presence of two identical, non-toxic objects and let to freely explore them for 5 minutes (trial 1). The time spent exploring the objects was recorded, considering exploration any physical contact with an object and/or approach with obvious orientation to it within 5 cm. At the end of trial 1 the animals were returned to the home cage. After 3 minutes the mice were returned to the testing field where one of the familiar objects was replaced by a novel object. The mice were allowed to explore the arena for 5 minutes and time exploring the objects monitored again. Recognition index (RI) was calculated as time the animals spent exploring the novel object to the total time spent exploring both the objects.

Elevated Plus Maze (EPM):

12-14 mice per group were tested for anxiety using an Elevated Plus Maze (EPM). The mice were tested before the dietary intervention, at the age of 8-9 months, and every month of treatment until the age of 12.5-13.5 months. The EPM has the shape of a cross formed by two alternate open and two alternate closed arms extending from a central platform, each arm measuring 30 cm length, 5 cm width and 15 cm height (Carroll et al. 2010). The test is based on rodent exploratory behavior, balanced by natural rodent aversion against open space. The avoidance of elevated open arms is an indication of the intensity of anxiety. During the test the mouse was placed onto the center field and allowed to freely explore the maze for 5 minutes, and the time spent in the open arms, corresponding to lower anxiety levels, was measured.

Immunohistochemistry 8-10 fixed hemibrains per group were sectioned (40 µm) exhaustively in the horizontal plane using a vibratome Leica V1000S (Leica) and then processed for immunohistochemistry. Every seventh section (10 per brain) was immunostained with antibodies directed against Aβ (71-5800 Aβ, Zymed Laboratories, San Francisco, Calif., USA), hyperphosphorylated tau (AT8, Pierce, Rockford, Ill., USA) or CD11b (MCA711, Serotec, Kidlington, UK) using ABC Vector Elite and DAB kits (Vector Laboratories, Burlingame, Calif., USA). For all the experiments the immunoreactivity quantification was assessed by two observers blind to sample identity and the values were averaged.

Aβ:

To enhance Aβ immunoreactivity (IR), sections were rinsed for 5 min in 99% formic acid. Aβ IR was calculated as load values. Briefly, selected fields of non-overlapping immunolabeled sections of hippocampus (two fields for subiculum and three for CA1—Cornu Ammonis area 1—) were captured and digitized using a video capture system coupled to a microscope. Using NIH Scion image 1.62C software images were converted into binary/negative data and the positive pixels (equivalent to IR area) quantified (Carroll et al. 2010). Also, Aβ plaques were defined as extracellular Aβ-immunoreactive deposits exhibiting a spherical shape and morphology distinct from intraneuronal Aβ IR (Rosario et al. 2006). For quantification combined hippocampal CA1 and subiculum regions from the sections defined above were examined under light microscopy and the total number of extracellular plaques was counted. The area of each plaque was quantified using ImageJ software.

Tau

AT8-immunoreactive neurons were defined as cells showing strong AT8 immunolabeling over most of the cell surface. The positive cells were been counted within the combined hippocampal CA1 and subiculum regions (Carroll et al. 2010).

CD11b:

CD11b-immunoreactive (ir) positive microglia cells were defined as cells covered by CD11b immunostaining over the cell body and processes. CD11b-ir cells were been counted in two adjacent non-overlapping immunolabeled sections (five sections in total) of the combined hippocampal subiculum and CA1 regions. Moreover, the stage of cells activation was identified by their morphology. Briefly, we defined four stages of microglia activation (Zhang et al. 2011):

Stage 1: Resting microglia. Rod-shaped soma with many long thin ramified processes.

Stage 2: Activated ramified microglia. Elongated cell body, the processes are thicker.

Stage 3: Amoeboid microglia showing a marked cellular hypertrophy and short and thick processes Stage 4: Phagocytic cells. Round cells, processes are not detectable.

CD11b-ir cells in the different activation stages were counted and plotted as percentage of the total ir cell number.

Statistical Analysis

Body weight and calories intake changes over the time were analyzed by repeated measures ANOVA followed by Newman-Keuls test. Raw behavioral data were analyzed by One-way ANOVA followed by between-group comparisons using the Fisher's least significant difference test. T-test was used when suitable. All the data represent mean values+/− SEM.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES CITED ABOVE

C. Lee, V. D. Longo, *Oncogene* 30, 3305 (2011).
M. Holzenberger et al., *Nature* 421, 182 (2003).
L. Fontana, L. Partridge, V. D. Longo, *Science* 328, 321 (2010).
J. Guevara-Aguirre et al., *Sci Transl Med* 3, (2011).
V. D. Longo, L. M. Ellerby, D. E. Bredesen, J. S. Valentine, E. B. Gralla, *J Cell Biol* 137, 1581 (1997).
C. Lee et al., *Cancer Research* 70, 1564 (2010).
L. Raffaghello et al., *P Natl Acad Sci USA* 105, 8215 (2008).
F. M. Safdie et al., *Aging* 1, 988 (2009).
C. M. van Tilburg et al., *Brit J Haematol* 152, 201 (2011).
P. Mauch et al., *International Journal of Radiation Oncology*, Biology, Physics 31, 1319 (1995).
M. D. Williams et al., *Crit Care* 8, 8291 (2004).
C. L. Mackall et al., *Blood* 84, 2221 (1994).
K. P. Sanghera et al., *Molecular and Cellular Neurosciences* 47, 145 (2011).
A. E. Kofman, M. R. McGraw, C. J. Payne, *Aging* 4, 279 (2012).
K. Ito et al., *Nat Med* 12, 446 (2006).
J. Ratajczak et al., *Leukemia* 25, 729 (2011).
M. Z. Ratajczak, E. K. Zuba-Surma, B. Machalinski, J. Ratajczak, M. Kucia, *Stem Cell Rev* 4, 89 (2008).

M. Z. Ratajczak, D. M. Shin, J. Ratajczak, M. Kucia, A. Bartke, *Aging-US* 2, 875 (2010).

M. Kucia et al., *Leukemia* 20, 857 (2006).

J. Ratajczak et al., *Leukemia* 25, 1278 (2011).

J. Ratajczak et al., *Exp Hematol* 39, 225 (2011).

K. Matsumoto et al., Plos One 4, (2009).

S. Rybtsov et al., J Exp Med 208, 1305 (2011).

P. Bedford, M. R. Berger, G. Eisenbrand, D. Schmahl, *Journal of Cancer Research and Clinical Oncology* 108, 141 (1984).

T. Yahata et al., *Blood* 118, 2941 (2011).

G. B. Adams et al., *Nature Biotechnology* 25, 238 (2007).

M. J. Kucia et al., *Stem Cells* 26, 2083 (2008).

K. A. Al-Regaiey, M. M. Masternak, M. Bonkowski, L. Sun, A. Bartke, *Endocrinology* 146, 851 (2005).

L. S. Kirschner, Z. Yin, G. N. Jones, E. Mahoney, *Endocrine-related cancer* 16, 773 (2009).

C. Lee et al., *Sci Transl Med* 4, 124ra27 (2012).

S. Y. Kim, D. J. Volsky, *BMC Bioinformatics* 6, (2005).

P. Fabrizio, F. Pozza, S. D. Pletcher, C. M. Gendron, V. D. Longo, *Science* 292, 288 (2001).

J. Rinaldi et al., *Structure* 18, 1471 (2010).

J. Kuret, K. E. Johnson, C. Nicolette, M. J. Zoller, *Journal of Biological Chemistry* 263, 9149 (1988).

P. Fabrizio et al., *Genetics* 163, 35 (2003).

G. A. Gonzalez, M. R. Montminy, *Cell* 59, 675 (1989).

P. De Coppi et al., *Nature Biotechnology* 25, 100 (2007).

A. Ditadi et al., *Blood* 113, 3953 (2009).

K. Yamamizu et al., *Stem Cells* 30, 687 (2012).

S. Faherty, A. Fitzgerald, M. Keohan, L. R. Quinlan, *In Vitro Cell Dev-An* 43, 37 (2007).

V. D. Longo, C. E. Finch, *Science* 299, 1342 (2003).

S. Zaman, S. I. Lippman, X. Zhao, J. R. Broach, *Annu Rev Genet* 42, 27 (2008).

M. Wei et al., *Plos Genet* 5, (2009).

C. Kenyon, *Cell* 105, 165 (2001).

A. B. Salmon et al., *Am J Physiol-Endoc M* 289, E23 (2005).

F. J. Ramos et al., *Sci Transl Med* 4, 144ra103 (2012).

N. G. Kolosova et al., *The American Journal of Pathology* 181, 472 (2012).

L. Bondolfi, F. Ermini, J. M. Long, D. K. Ingram, M. Jucker, *Neurobiol Aging* 25, 333 (2004).

R. P. Ertl, J. Chen, C. M. Astle, T. M. Duffy, D. E. Harrison, *Blood* 111, 1709 (2008).

J. C. Chen, C. M. Astle, D. E. Harrison, *Exp Hematol* 31, 1097 (2003).

V. A. Rafalski, A. Brunet, *Prog Neurobiol* 93, 182 (2011).

T. A. Rando, H. Y. Chang, *Cell* 148, 46 (2012).

K. T. Nimeth et al., *Dev Dyn* 230, 91 (2004).

F. A. Vieira et al., *BMC Genomics* 12, 490 (2011).

O. H. Yilmaz et al., *Nature* 486, 490 (2012).

Q. S. Pang, *Blood* 118, 2932 (2011).

Bokov A F, Garg N, Ikeno Y, Thakur S, Musi N, DeFronzo R A, Zhang N, Erickson R C, Gelfond J, Hubbard G B, Adamo M L, Richardson A (2011). *PLoS One.* 6, e26891.

Brown-Borg H M, Borg K E, Meliska C J, Bartke A (1996), *Nature.* 384, 33.

Carro E, Nunez A, Busiguina S, Torres-Aleman I (2000), *J Neurosci.* 20, 2926-2933.

Carro E, Torres-Aleman I (2004), *Expert Rev Neurother.* 4, 79-86.

Carro E, Trejo J L, Gomez-Isla T, LeRoith D, Torres-Aleman I (2002), *Nat Med.* 8, 1390-1397.

Carroll J C, Rosario E R, Villamagna A, Pike C J (2010), *Endocrinology.* 151, 2713-2722.

Cohen E, Paulsson J F, Blinder P, Burstyn-Cohen T, Du D, Estepa G, Adame A, Pham H M, Holzenberger M, Kelly J W, Masliah E, Dillin A (2009), *Cell.* 139, 1157-1169.

Coschigano K T, Clemmons D, Bellush L L, Kopchick J J (2000), *Endocrinology.* 141, 2608-2613.

de Leon M J, DeSanti S, Zinkowski R, Mehta P D, Pratico D, Segal S, Rusinek H, Li J, Tsui W, Saint Louis L A, Clark C M, Tarshish C, Li Y, Lair L, Javier E, Rich K, Lesbre P, Mosconi L, Reisberg B, Sadowski M, DeBernadis J F, Kerkman D J, Hampel H, Wahlund L O, Davies P (2006), *Neurobiol Aging.* 27, 394-401.

Fabrizio P, Pozza F, Pletcher S D, Gendron C M, Longo V D (2001, (*Science.* 292, 288-290.

Fontan-Lozano A, Lopez-Lluch G, Delgado-Garcia J M, Navas P, Carrion A M (2008), *Mol Neurobiol.* 38, 167-177.

Fontana L, Partridge L, Longo V D (2010), *Science.* 328, 321-326.

Fontana L, Weiss E P, Villareal D T, Klein S, Holloszy J O (2008), *Aging Cell.* 7, 681-687.

Gietzen D W, Hao S, Anthony T G (2007), *Annu Rev Nutr.* 27, 63-78.

Goedert M, Jakes R, Vanmechelen E (1995), *Neurosci Lett.* 189, 167-169.

Guevara-Aguirre J, Balasubramanian P, Guevara-Aguirre M, Wei M, Madia F, Cheng C W, Hwang D, Martin-Montalvo A, Saavedra J, Ingles S, de Cabo R, Cohen P, Longo V D (2011), *Sci Transl Med.* 3, 70ra13.

Gulinello M, Gertner M, Mendoza G, Schoenfeld B P, Oddo S, LaFerla F, Choi C H, McBride S M, Faber D S (2009), *Behav Brain Res.* 196, 220-227.

Halagappa V K, Guo Z, Pearson M, Matsuoka Y, Cutler R G, Laferla F M, Mattson M P (2007), *Neurobiol Dis.* 26, 212-220.

Hwang D L, Lee P D, Cohen P (2008), *Growth Horm IGF Res.* 18, 65-74.

Ikeno Y, Hubbard G B, Lee S, Cortez L A, Lew C M, Webb C R, Berryman D E, List E O, Kopchick J J, Bartke A (2009). *J Gerontol A Biol Sci Med Sci.* 64, 522-529.

Jones J I, Clemmons D R (1995), *Endocr Rev.* 16, 3-34.

Kenyon C (2005), *Cell.* 120, 449-460.

Ketelslegers J M, Maiter D, Maes M, Underwood L E, Thissen J P (1995), *Metabolism.* 44, 50-57.\

Kinney B A, Coschigano K T, Kopchick J J, Steger R W, Bartke A (2001), *Physiol Behav.* 72, 653-660

Kitazawa M, Oddo S, Yamasaki T R, Green K N, LaFerla F M (2005), *J Neurosci.* 25, 8843-8853.

Lee C, Longo V D (2011), *Oncogene.* 30, 3305-3316.

Luchsinger J A, Tang M X, Shea S, Mayeux R (2002), *Arch Neurol.* 59, 1258-1263.

Martin B, Mattson M P, Maudsley S (2006), *Ageing Res Rev.* 5, 332-353.

Masternak M M, Panici J A, Bonkowski M S, Hughes L F, Bartke A (2009). Insulin sensitivity as a key mediator of growth hormone actions on longevity. *J Gerontol A Biol Sci Med Sci.* 64, 516-521.

Mattson M P (2005), *Annu Rev Nutr.* 25, 237-260.

Mouton P R, Chachich M E, Quigley C, Spangler E, Ingram D K (2009), *Neurosci Lett.* 464, 184-187.

Oddo S, Caccamo A, Kitazawa M, Tseng B P, LaFerla F M (2003), *Neurobiol Aging.* 24, 1063-1070.

Parrella E, Longo V D (2010), *Scientific World Journal.* 10, 161-177.

Patel N V, Gordon M N, Connor K E, Good R A, Engelman R W, Mason J, Morgan D G, Morgan T E, Finch C E (2005), *Neurobiol Aging.* 26, 995-1000.

Roberson E D, Scearce-Levie K, Palop J J, Yan F, Cheng I H, Wu T, Gerstein H, Yu G Q, Mucke L (2007), *Science.* 316, 750-754.

Rosario E R, Carroll J C, Oddo S, LaFerla F M, Pike C J (2006), *J Neurosci.* 26, 13384-13389.

Schrag M, Sharma S, Brown-Borg H, Ghribi O (2008), *Hippocampus.* 18, 239-244. Sharma S, Darland D, Lei S, Rakoczy S, Brown-Borg H M (2012), *Age* (Dordr). 34, 609-620.

Sharma S, Haselton J, Rakoczy S, Branshaw S, Brown-Borg H M (2010). *Mech Ageing Dev.* 131, 422-435.

Sonntag W E, Lynch C D, Cefalu W T, Ingram R L, Bennett S A, Thornton P L, Khan A S (1999). Pleiotropic effects of growth hormone and insulin-like growth factor (IGF)-1 on biological aging: inferences from moderate caloric-restricted animals. *J Gerontol A Biol Sci Med Sci.* 54, B521-538.

Suh Y, Atzmon G, Cho M O, Hwang D, Liu B, Leahy D J, Barzilai N, Cohen P (2008), *Proc Natl Acad Sci USA.* 105, 3438-3442.

Talbot K, Wang H Y, Kazi H, Han L Y, Bakshi K P, Stucky A, Fuino R L, Kawaguchi K R, Samoyedny A J, Wilson R S, Arvanitakis Z, Schneider J A, Wolf B A, Bennett D A, Trojanowski J Q, Arnold S E (2012), *J Clin Invest.* 122, 1316-1338.

Thissen J P, Ketelslegers J M, Underwood L E (1994), *Endocr Rev.* 15, 80-101.

Vardy E R, Rice P J, Bowie P C, Holmes J D, Grant P J, Hooper N M (2007), *J Alzheimers Dis.* 12, 285-290.

Wang J, Ho L, Qin W, Rocher A B, Seror I, Humala N, Maniar K, Dolios G, Wang R, Hof P R, Pasinetti G M (2005), *FASEB J.* 19, 659-661.

Wu P, Shen Q, Dong S, Xu Z, Tsien J Z, Hu Y (2008), *Neurobiol Aging.* 29, 1502-1511.

Yamamoto H, Murphy L J (1995), *J Endocrinol.* 146, 141-148.

Young S N (1996), *Neurosci Biobehav Rev.* 20, 313-323.

Zhang S, Wang X J, Tian L P, Pan J, Lu G Q, Zhang Y J, Ding J Q, Chen S D (2011)m, *J Neuroinflammation.* 8, 154.

L. Bondolfi, F. Ermini, J. M. Long, D. K. Ingram, M. Jucker, *Neurobiol Aging* 25, 333 (2004).

R. P. Ertl, J. Chen, C. M. Astle, T. M. Duffy, D. E. Harrison, *Blood* 111, 1709 (2008).

J. C. Chen, C. M. Astle, D. E. Harrison, *Exp Hematol* 31, 1097 (2003).

O. H. Yilmaz et al., *Nature* 486, 490 (2012).

C. Lee, V. D. Longo, *Oncogene* 30, 3305 (2011).

A. Bartke, L. Y. Sun, V. Longo, *Physiol Rev.* 93, 571-98 (2013).

What is claimed is:

1. A method for improving age-dependent working memory deficits and short term spatial memory, the method comprising:
   administering an amino acid specific diet supplement for a time period of about 5 days to 14 days, the amino acid specific diet supplement comprising the following amino acids as a source of nitrogen: alanine, aspartic acid, cysteine, glutamic acid, glycine, histidine, proline, serine, and tyrosine while substantially excluding isoleucine, leucine, lysine, methionine, phenylalanine, threonine, tryptophan, valine, and arginine such that isoleucine, leucine, lysine, methionine, phenylalanine, threonine, tryptophan, valine, and arginine which in combination are administered in an amount that is less than 5% of a total weight of a subject's diet.

2. The method of claim 1 wherein isoleucine, leucine, lysine, methionine, phenylalanine, threonine, tryptophan, valine, and arginine in combination are present in an amount that is less than 3% of a total weight of a subject's diet.

* * * * *

UNITED STATES PATENT AND TRADEMARK OFFICE
CERTIFICATE OF CORRECTION

| | |
|---|---|
| PATENT NO. | : 10,015,980 B2 |
| APPLICATION NO. | : 14/060494 |
| DATED | : July 10, 2018 |
| INVENTOR(S) | : Valter D. Longo et al. |

It is certified that error appears in the above-identified patent and that said Letters Patent is hereby corrected as shown below:

In the Specification

Column 1, Line 18:
Delete:
"The invention was made with Government support under Contract Nos. PO1AG034906, P01 AG 034906-01, and PO1AG020642. The Government has certain rights to the invention."
And insert:
--This invention was made with government support under Grant Nos. AG034906 and AG020642, awarded by the National Institutes of Health. The government has certain rights in the invention.--

Signed and Sealed this
Twenty-fourth Day of October, 2023

Katherine Kelly Vidal
*Director of the United States Patent and Trademark Office*